(12) United States Patent
Utecht et al.

(10) Patent No.: US 8,252,771 B2
(45) Date of Patent: Aug. 28, 2012

(54) BIOMATERIALS AND A METHOD FOR MAKING AND USING SAME

(75) Inventors: Ronald E. Utecht, Volga, SD (US);
Kaia L. Kloster, Hudson, SD (US);
Therese M. Downey, Sioux Falls, SD (US); Barbara R. Haberer, Hartford, SD (US); Patrick D. Youso, Brookings, SD (US); James N. Chang, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 1139 days.

(21) Appl. No.: 12/023,977

(22) Filed: Jan. 31, 2008

(65) Prior Publication Data

US 2008/0207561 A1    Aug. 28, 2008

Related U.S. Application Data

(60) Provisional application No. 60/887,559, filed on Jan. 31, 2007.

(51) Int. Cl.
*A61K 31/722* (2006.01)
*A61K 31/70* (2006.01)
*A61K 47/48* (2006.01)

(52) U.S. Cl. ............... 514/55; 514/23; 536/20; 536/124

(58) Field of Classification Search .................... 514/55, 514/23; 536/20, 124
See application file for complete search history.

(56) References Cited

U.S. PATENT DOCUMENTS

| | | | |
|---|---|---|---|
| 5,496,872 | A | 3/1996 | Constancis et al. |
| 5,773,033 | A | 6/1998 | Cochrum |
| 6,200,595 | B1 | 3/2001 | Motoyashiki et al. |
| 6,310,188 | B1 | 10/2001 | Mukherjee |
| 6,329,337 | B1 | 12/2001 | Morita et al. |
| 6,875,796 | B2 | 4/2005 | Stedronsky |
| 6,991,652 | B2 | 1/2006 | Burg |
| 7,514,399 | B2 | 4/2009 | Utecht et al. |
| 2008/0200948 | A1 | 8/2008 | Utecht et al. |

FOREIGN PATENT DOCUMENTS

| | | | |
|---|---|---|---|
| WO | WO 97/06782 | * | 2/1997 |
| WO | 2005-044309 | | 5/2005 |
| WO | 2005-113608 | | 12/2005 |

OTHER PUBLICATIONS

Cantor (Expert Opinion on Investigational Drugs (2001) 10(4) 721-731).*
U.S. Appl. No. 10/982,197, filed Nov. 5, 2004, Utecht et al.
Domard (Int. J. Biol. Macromol. 1987, vol. 9, 98-104).
Park, J.H.; Cho, Y.W.; Chung, H.; Kwon, I.C.; Jeong, S.Y. "Synthesis and Characterization of Sugar-Bearing Chitosan Derivatives: Aqueous Solubility and Biodegradability" Biomacromolecules 2003, 4, 1087-1091.

* cited by examiner

*Primary Examiner* — Shaojia Anna Jiang
*Assistant Examiner* — Michael C Henry
(74) *Attorney, Agent, or Firm* — Louis V. Wollenberger; Joel B. German; Debra D. Condino

(57) ABSTRACT

A biomaterial is disclosed having unique properties that make it useful in ocular drug delivery applications, where the drugs selected from the group consisting of a prostaglandin, a prostamide, a non-steroidal anti-inflammatory drug (NSAID), and a corticosteroid, and mixtures, derivatives, salts and esters thereof.

3 Claims, 25 Drawing Sheets

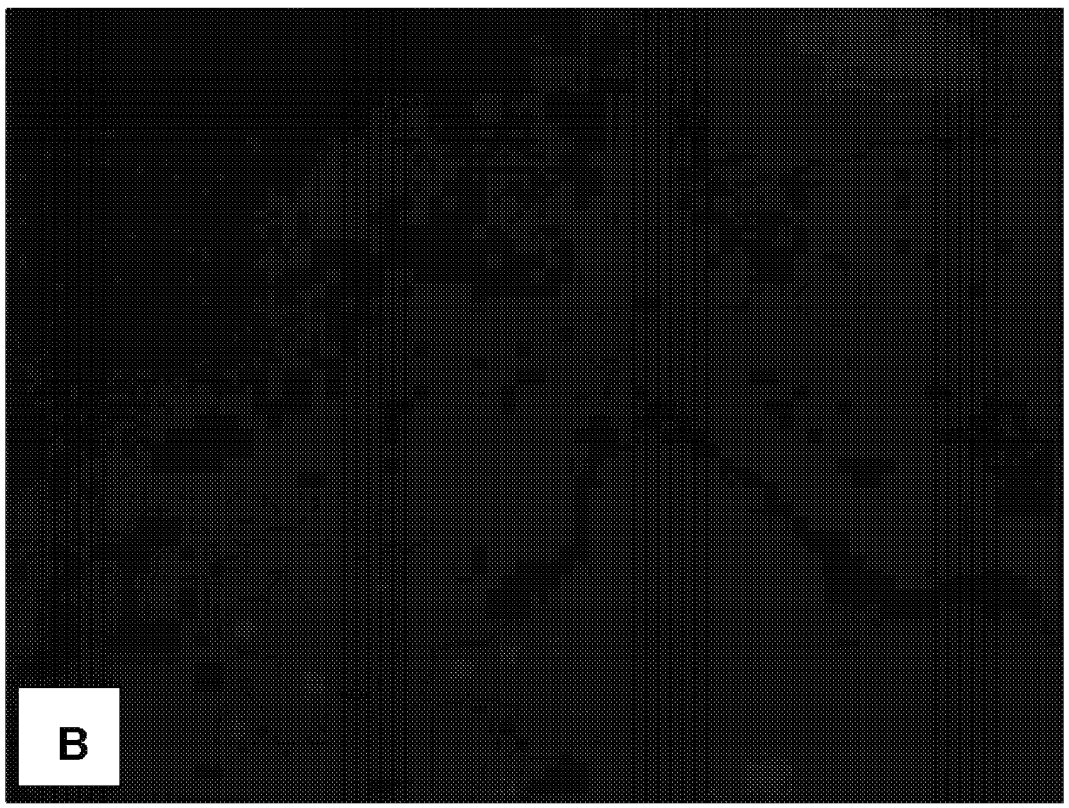
FIG. 14A&B

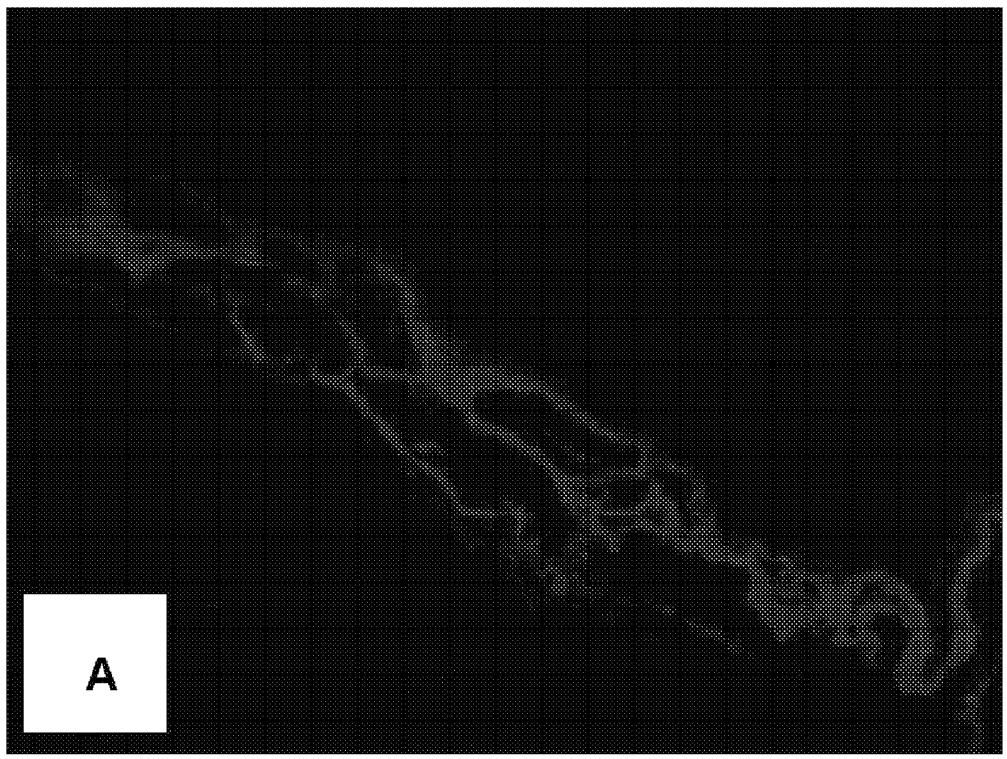
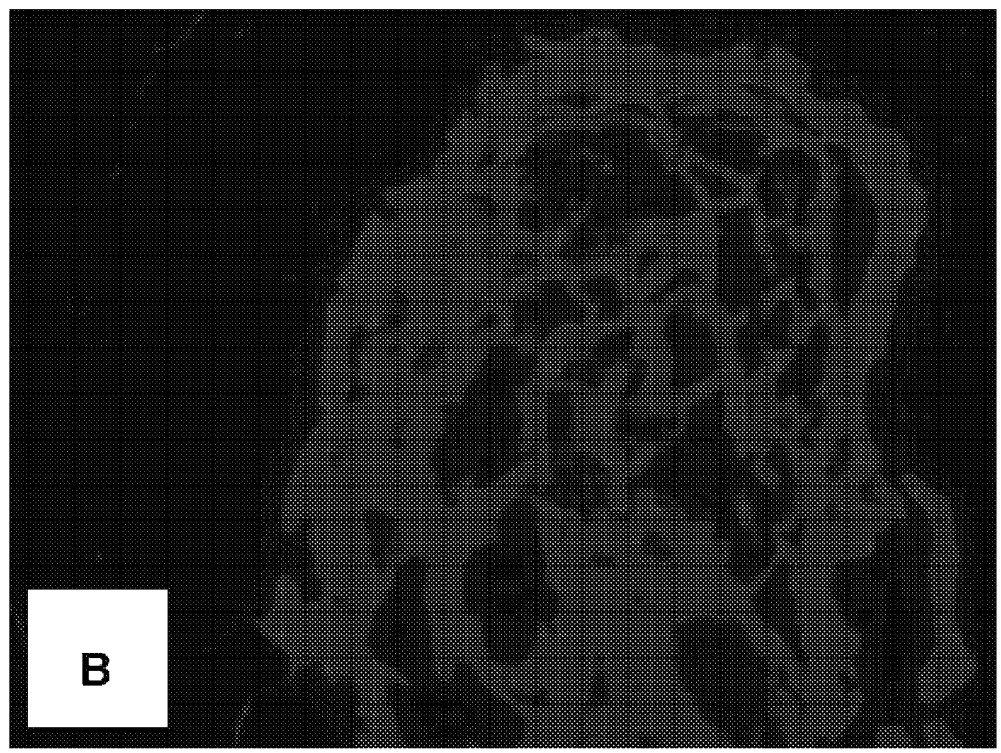
FIG. 19A&B

Periocular Injections
29-day results
CONTROL – SALINE INJECTION
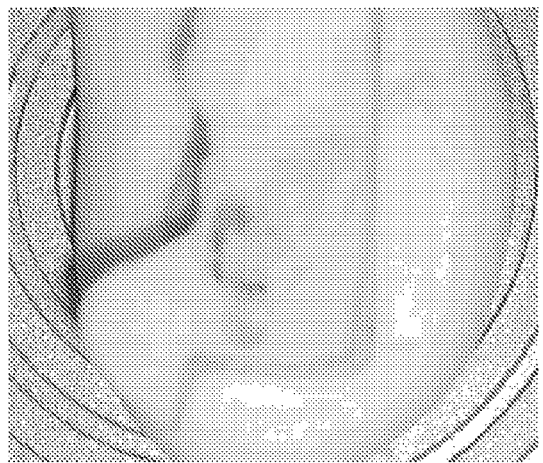 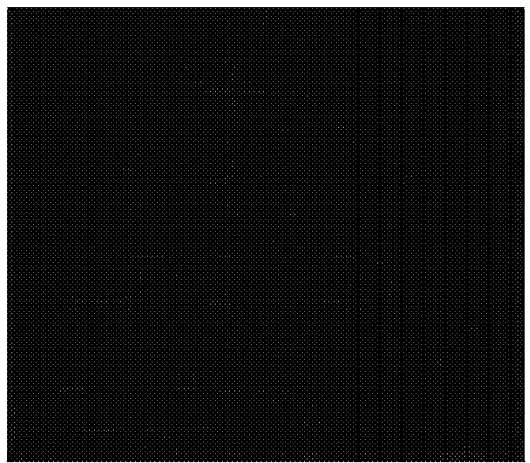
Frozen block after cryosectioning      Calc fluor staining
FIG. 20A
EXPERIMENTAL FORMULATION
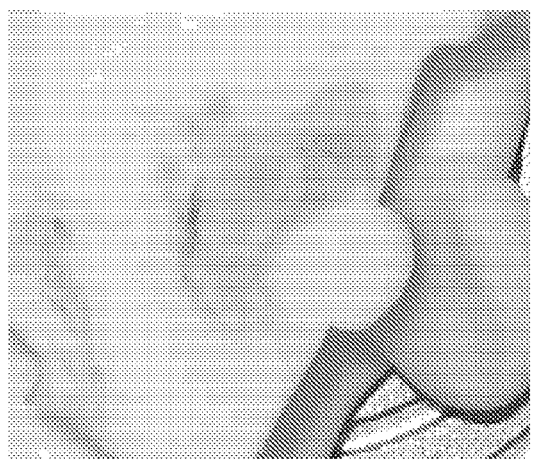 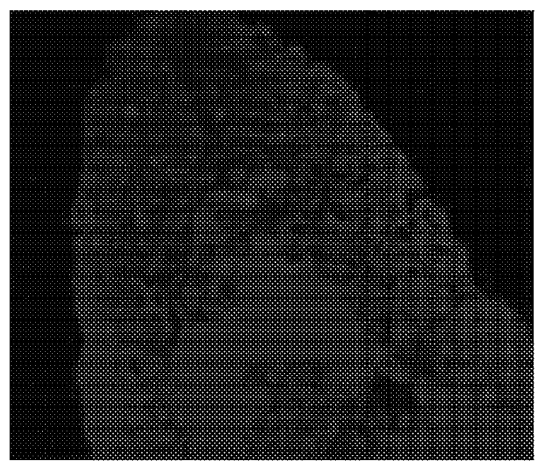
Frozen block after cryosectioning      Calc fluor staining
FIG. 20B

BIOMATERIALS AND A METHOD FOR MAKING AND USING SAME

RELATED APPLICATION

This application claims priority to and the benefit of U.S. patent application Ser. No. 12/023,963, filed 31 Jan. 2008, which claims priority to and the benefit of U.S. Provisional Patent Application Ser. No. 60/887,559, filed 31 Jan. 2007, incorporated herein by reference.

BACKGROUND OF THE INVENTION

1. Field of the Invention

The present invention relates to novel biomaterials including treated chitosan compositions, modified chitosan compositions, modified and treated chitosan compositions, or mixtures or combinations thereof and to methods for making and using same.

More particularly, the present invention relates to novel biomaterials including treated chitosans, modified chitosans, modified and treated chitosans or mixtures or combinations thereof, where at least one chitosan has one or more physical, chemical, and/or performance properties or characteristics that distinguish the treated chitosan, the modified chitosan, or the modified and treated chitosan over similar compositions including corresponding untreated chitosan. The present invention also relates to adhesive compositions or systems including a chitosan composition of this invention, drug delivery compositions or systems including a chitosan composition of this invention, filler or bulking compositions or systems including a chitosan composition of this invention, and to methods for making and using the same.

2. Description of the Related Art

Competitive Adhesive Technologies

The search for an effective tissue adhesive has resulted in many products, all of which suffer from deficiencies.

The most common tissue adhesives currently on the market are fibrin sealant based products. In this system the components of the natural clotting factors, fibrinogen and thrombin, react mimicking the final stage of the body's natural clotting mechanism. The resulting fibrin clot or film adheres to tissues to stop bleeding and improve the wound healing. The bond strengths of these products are not sufficient to hold tissues in approximation without the use of mechanical closures such as staples or sutures.

Cyanoacrylate products have been used to close skin breaks in the United States. When applied to tissue, the cyanoacrylate monomer undergoes an exothermic hydroxylation reaction that results in polymerization of the adhesive. The biological alkyl chains can be modified to modulate the physiological response. The shorter-chain derivatives (methyl and ethyl) tend to have a higher degree of tissue toxicity than the longer-chain derivatives (2-octyl). Inflammation, tissue necrosis, granulation formation, and wound breakdown can occur when cyanoacrylates are implanted subcutaneously. The process causing the histological toxicity is thought to be related to the by-products of degradation, cyanoacetate and formaldehyde. The cured polymer is brittle and presents a barrier to tissue regrowth. The addition of plasticizers can provide a more flexible bonding substrate.

Natural proteins such as collagen and albumin can be cross-linked with aldehyde cross-linking agents producing a biologically based adhesive. Concerns such as the toxicity associated with the aldehyde component, complexity of use and irreproducible results have limited the acceptance by physicians. This type of adhesive was first approved with a humanitarian device exemption (HDE) but has seen some expansion of use both on and off label. The product is glutaraldehyde crosslinked bovine serum albumin (BSA). The presence of glutaraldehyde prohibits its contact with neural tissues, as it can cause acute nerve injury. This class of adhesive has also been shown to impair aortic growth and to cause anastomotic strictures, thereby precluding its use in children. In addition, the adhesive has a very rapid curing time causing frequent blockage in the dual chamber delivery syringe and resulting in inconsistent bonding efficacy. These associated difficulties or complications limit its effectiveness.

Natural proteins secreted by such organisms as mussels, or synthetic analogues, have been used as tissue adhesives. These technologies require the use of primers and polymerizing agents that are typically toxic, severely compromising their potential biocompatibility and safety. Synthetic polymers have been developed that center around engineered proteins that resemble collagen and elastin. Impressive bond strengths have been realized, see, e.g., U.S. Pat. No. 6,875,796, with materials that would appear to be biocompatible. In order to achieve these bond strengths, tissues are primed with materials, such as chloroform, that would not be compatible with tissues. In addition the matrix is strengthened through the addition of incompatible crosslinkers, dopes, and primers, such as glutaraldehyde, formaldehyde, 1,6-diisocyanatohexane, 4-isocyanatomethylphenyl-3-isocyantopropanate, resorcinol, Eosin Y and Eosin B. Similarly, a proposed class of dendritic materials also requires the added complexity and potential toxicity issues involved with the use of biologically incompatible primers.

Polyethylene glycol (PEG) products are on the market but their strength is fairly low, even with photopolymerization, and most products require mixing prior to use. Surgeon acceptance has apparently been slow even with the relative biological safety of the products.

Competitive Local Drug Delivery Technologies

Local drug delivery technology can be grouped by function. Sustained release technology seeks to deliver the active pharmaceutical over an extended time. Polymeric materials that physically entrap the drug may provide a means for providing passive delivery over a period of time. In addition, the polymeric materials can supply enhanced characteristics such as stability or solubility enhancement. The polymer matrix may be degraded, retrieved or left in place in the case of many implantable devices, at the end of the drug delivery cycle.

To increase the specificity of the local drug delivery, targeted delivery technologies seek to enhance the movement and/or release of the pharmaceutical agent(s) through the use of focused RF or ultrasound.

Enhanced absorption/transport technologies seek to increase the absorption of the drug by increasing the uptake by target tissues. This has been found to be especially effective when used in a mucosal environment.

In the above technologies, the drug is passively released or released on an external trigger, not as a response to metabolic state or excretion of metabolic products by cells comprising the tissues.

Competitive Filler or Bulking Technologies

Dermal fillers are typically produced from bovine collagen, hyaluronic acid, poly-lactic acid, or calcium hydroxylapatite. Dermal fillers are used to reduce or eliminate wrinkles, raise scar depressions, enhance lips or replace soft-tissue volume loss. Injection of fillers is usually accomplished using a small needle, the dermal filler is injected into each wrinkle or scar that requires treatment. Some initial discomfort and bruising is experienced but such side effects generally subside quite quickly. Side effects are uncommon but can include allergic reactions, ulceration, reactivation of herpes infection, bacterial infection, localized bruising, and granuloma formation. Movement or "beading" of the material is sometimes seen giving an unpleasing aesthetic result. The benefits resulting from the increase in volume generally lasts for three to six months for the biologically derived fillers, somewhat longer with the synthetic materials. Improvements in the longevity and performance of the filler materials, as well as a decrease in adverse side effects, are currently being sought by the industry.

Chitosan History

Chitosan is a cationic polysaccharide derived from the partial deacetylation of chitin from the exoskeleton of crustaceans, including shrimp, lobster, and crabs. Its chemical nature is best described as a deacylated-(1,4)-N-acetyl-D-glucosamine polymer. The adhesive nature of chitosan has been known for some time. However, to date, no adhesive product based on chitosan has been produced. This is due in large measure to the difficulties in handling chitosan and delivering it in a form that quickly bonds to tissue without associated problems due to high acid concentrations. According to a search on the USPTO database, only 14 patents have been filed with an abstract or claims containing chitosan and adhesive. Most of these patents are for the paper industry. U.S. Pat. No. 5,773,033 disclosed fibrinogen/chitosan hemostatic agents, but not for use in tissue bonding. U.S. Pat. No. 6,329,337 entitled "Adhesive for Biological Tissue" disclosed a glue agent produced from a recombinant human plasma protein and bifunctional or multifunctional aldehydes. Chitosan was used in the agent to enhance the viscosity of the solution or as a crosslinking reagent with bifunctional or multifunctional aldehydes. U.S. Pat. No. 5,496,872 disclosed chitosan in a fairly exhaustive list of potential reagents, but relies on thiols, carboxylic acids and radicals to bond. U.S. Pat. No. 6,200,595 disclosed a combination of polycationic substrates, including chitosan, along with polyanionic substrates to be used as a potential medical adhesive. Reported bond strengths in this patent did not exceed 70 g-f/cm$^2$. Additionally, this invention requires mixing of two components immediately prior to use. U.S. Pat. No. 6,991, 652 disclosed the use of chitosan as one in a list of many potential materials to be used as a matrix for cellular growth.

A survey of the literature revealed that dialysis of chitosan has been used as a purification step and as a means for introducing coadditives. For example, U.S. Pat. No. 6,310,188 utilizes dialysis of chitosan to remove low molecular weight compounds.

Although a number of systems have been considered for use in the arena of tissue adhesives, the currently available systems suffer from deficiencies including toxicity, insufficient strength, or difficulty in use. Thus, there is a need in the art for additional compositions that are safe and effective tissue adhesives that can be provided in a sterile and easy-to-use form. Such highly adherent compositions would also offer significant advantages in drug delivery. There is also a need in the art for compositions that remain highly hydrated offering novel fillers, bulking compositions, or reconstructive compositions for use in cosmetic and reconstructive surgical procedures.

DEFINITIONS OF THE INVENTION

The term "about" means that the parameter is within ±10% of the desired value.

The term "substantially uniform" means that a composition evidences less than a 10% difference in properties throughout the composition.

A biological agent is a compound or collection of compounds that imparts a desired property to a member of the animal or plant kingdoms, including microorganisms and higher order organisms up to and including mammals such as humans and the advanced plants or causes a desired effect on a member of the animal or plant kingdoms, including microorganisms and higher order organisms up to and including mammals such as humans and the advanced plants. A biological agent can be active from the outset for the desired effect or can be made active either via metabolism or external activation by an activating agent. In the Suitable Reagent section, a list or articulation of biological agents is given; these agents include all the biocides, pharmaceuticals, nutraceuticals, or any other compound that directly or indirectly can bring about a desired biological effect, whether that be death (biocides), treatments (pharmaceuticals), preventatives (nutraceuticals, vitamins, etc.) or the like.

A pharmaceutical composition is a formulation which contains at least one active ingredient (for example a topically applied therapeutic agent). In certain embodiments the composition may also contain one or more excipients, buffers, carriers, stabilizers, preservatives and/or bulking agents, and is suitable for administration to a patient to achieve a desired effect or result. The pharmaceutical compositions disclosed herein can have diagnostic, therapeutic, cosmetic and/or research utility in various species, such as for example in human patients or subjects.

An ocular condition can include a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. The anterior segment of the human eye is the front third of the eye (those portions of the eye in front of the vitreous humour) including the iris, cornea, ciliary body and lens. The posterior segment of the eye then contains the vitreous humour, retina, choroids and the optic nerve.

An anterior ocular condition is a disease, ailment or condition which affects or which involves an anterior (i.e. front of the eye) ocular region or site, such as a periocular muscle, an eye lid or an eyeball tissue or fluid which is located anterior to the posterior wall of the lens capsule or ciliary muscles. Thus, an anterior ocular condition primarily affects or involves, the conjunctiva, the cornea, the anterior chamber, the iris, the posterior chamber (behind the retina but in front of the posterior wall of the lens capsule), the lens or the lens capsule and blood vessels and nerves which vascularize or innervate an anterior ocular region or site.

A posterior ocular (also referred to herein synonymously as a "posterior segment") condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

SUMMARY OF THE INVENTION

The present invention provides biomaterials including treated chitosans, modified chitosans, modified and treated chitosans, or mixtures or combinations thereof. The treated chitosans are prepared by dialyzing the chitosan against water and various salts and/or anionic solutions. In these embodiments, the treated chitosans have structural conformations that are identifiably and reproducibly altered from untreated chitosan. The resulting treated chitosans exhibit changes in chemical, physical and/or performance properties or characteristics relative to untreated chitosan. Modified chitosans include chitosan that have undergone chemical modifications through covalent attachments of one or more functional groups to the chitosan molecules. Modified chitosans also include chitosans that have been non-covalently associated with one or more distinct chemical modifiers, either atomic structures or molecular structures. Modified chitosans can also include chitosans that have coadditions of any number of distinct chemical modifiers, either atomic structures or molecular structures. Modified chitosans can also include a combination or mixture of the three above-identified classes of modified chitosans. Chemical modifiers are generally selected to impart a desired behavior, property or characteristic to the chitosan for a given application. The compositions of the present invention can be formulated into a number of physical forms including, but not limited to, liquids, hydrogels, solids, thin films, particles, shaped structures, and nanoparticles.

The unique biomaterials of this invention have demonstrated feasibility for use as novel adhesive compositions or systems, as a novel means for local drug delivery, and as novel filling or bulking materials. Formulations of this invention have significant advantage over competitive technologies. These advantages include for example: safety and efficacy; ready-to-use, sterile formulations; formulations having an adjustable viscosity; formulations with rapidly adjustable pH and reserve acidity amenable to physiological applications; formulations that are easily and quickly manufactured from affordable base materials, etc.

The present invention also provides novel drug delivery systems.

The present invention also provides novel filling or bulking materials.

The present invention provides a composition including a treated chitosan, a modified chitosan, a modified and treated chitosan or mixtures thereof and a biological agent, where the biological agent can be a bioactive agent such as a pharmaceutically active agent, and where the biological agent is released into a site of an organism from the plant kingdom or animal kingdom including a human when the composition is administered to the organism.

The present invention provides a composition including a treated chitosan, a modified chitosan, a modified and treated chitosan or mixtures thereof, where at least one chitosan includes a bioactive agent such as a pharmaceutically active agent covalently bonded to at least one of the chitosans either directly or through a linker moiety, where the agent is released into or onto a site of an organism from the plant kingdom or animal kingdom including a human when the composition is administered to the organism over time depending on hydrolytic cleavage, enzymatic cleavage or a combination of hydrolytic cleavage and enzymatic cleavage of the agent.

The present invention provides an adhesive composition including a treated chitosan, a modified chitosan, a modified and treated chitosan or mixtures thereof, where the composition is tailored for non-living systems or for living systems. Optionally, the adhesive composition can include additives such as fillers, anti-oxidants, adhesive augmenting agents, or other agents added to the adhesive to modify or render the adhesive suitable for a particular purpose.

The present invention provides a process for making an adhesive composition of this invention including mixing a treated chitosan, a modified chitosan, a modified and treated chitosan or mixtures thereof with an additive package for a time, at a temperature and a pressure sufficient to form a substantially uniform adhesive composition, where the additive package is adapted to render the adhesive composition suitable for its intended purpose. Although in most of the procedures set forth herein, pressure was not independently measured or controlled so that the pressure was the dictated by temperature and volume or was simply atmospheric, the process is amenable to being performed at both subatmospheric pressure and at pressures greater than atmospheric.

The present invention provides a process for making a biological agent delivery composition including mixing a treated chitosan, a modified chitosan, a modified and treated chitosan or mixtures thereof with an effective amount of one biological agent or a plurality of biological agents under conditions to prepare a substantially uniform delivery composition, where the biological agent(s) is(are) biocides, pharmaceuticals, nutraceuticals, or the like.

The present invention provides a process for making a drug delivery composition including contacting a chitosan composition including a treated chitosan, a modified chitosan, modified and treated chitosan or a mixture or combination thereof with a pharmaceutically effective amount of one pharmaceutical agent or a plurality of pharmaceutical agents under conditions to form covalent linkages between the chitosan composition and the pharmaceutical agent or agents to form an extended release drug delivery composition. In certain embodiments, the composition is substantially uniform, while in other embodiments the composition can be non-uniform depending on the application and the desired effect.

The pharmaceutical agent or agents can be directly attached to moieties on the chitosan or can be attached to the moieties on the chitosan through linkers or linking groups to form covalent linkages between the pharmaceutical agent or agents to the chitosan. In certain embodiments, the covalent linkages are cleavable via hydrolysis, via enzymatic activity, via photolysis, or via a combination of hydrolysis, photolysis, and enzymatic activity. In other embodiments, the covalent linkages are not cleavable via hydrolysis, via enzymatic activity, via photolysis, or via a combination of hydrolysis, photolysis, and enzymatic activity.

The present invention provides a process for making a drug delivery composition including contacting a chitosan composition including a treated chitosan, a modified chitosan, modified and treated chitosan or a mixture or combination thereof with a pharmaceutically effective amount of one pharmaceutical agent or a plurality of pharmaceutical agents under conditions to prepare a substantially uniform drug delivery composition. Each modified chitosan include groups covalently bonded to sites or moieties on the chitosan that are capable of reacting with moieties on the pharmaceutical agents to from covalent linkages, where the covalent linkages are cleavable via hydrolysis, via photolysis, via enzymatic activity, or via a combination of hydrolysis, photolysis and enzymatic activity.

The present invention also provides in vitro tissue constructs for studying tissue adhesive properties, chitosan composition retention properties, and bioactive agent including pharmaceutical agent release properties. In one embodiment, the construct comprises a tissue culture having coated on a surface thereof a chitosan composition comprising a treated chitosan, a modified chitosan, a modified and treated chitosan, or a mixture thereof. In other embodiments, the construct comprises a first tissue culture, and a second tissue culture, and interposed therebetween composition comprising treated chitosan, a modified chitosan a modified and treated chitosan, or a mixture thereof. In other embodiments, the construct comprising a tissue culture and a patch material and interposed therebetween a composition comprising a treated chitosan, a modified chitosan, a modified and treated chitosan, or a mixture thereof. In all these constructs, the chitosan compositions and drug delivery systems based thereon can include pharmaceutical agents, excipients, buffers, adjuvants, carriers, stabilizers, preservatives and/or bulking agents suitable for administration (i.e. compatible to the eye) to a patient to achieve a desired effect or result.

BRIEF DESCRIPTION OF THE DRAWINGS

The invention can be better understood with reference to the following detailed descriptions together with the appended illustrative drawings in which like elements are numbered the same.

FIG. 14 depicts evidence of the retention of the material of Example 1 on the corneal surface of a rabbit eye two hours post-application, using calcofluor staining to positively identify the chitosan-based composition (A) compared to control (B) in vivo study.

FIG. 19 depicts residual presence of two compositions of this invention in the periocular space 29 days after injection—compound A: The material of Example 1 at 10 mg/mL concentration; compound B: An alternate formulation at 70 mg/mL concentration. Calcofluor staining was used to positively identify the chitosan-based composition—in vivo study.

FIG. 20 depicts residual presence of the material of Example 25, which included covalently bound bimatoprost, in the periocular space 29 days after injection, using calcofluor staining to positively identify the chitosan-based composition—in vivo study.

DETAILED DESCRIPTION OF THE PREFERRED EMBODIMENTS

Figure 1:
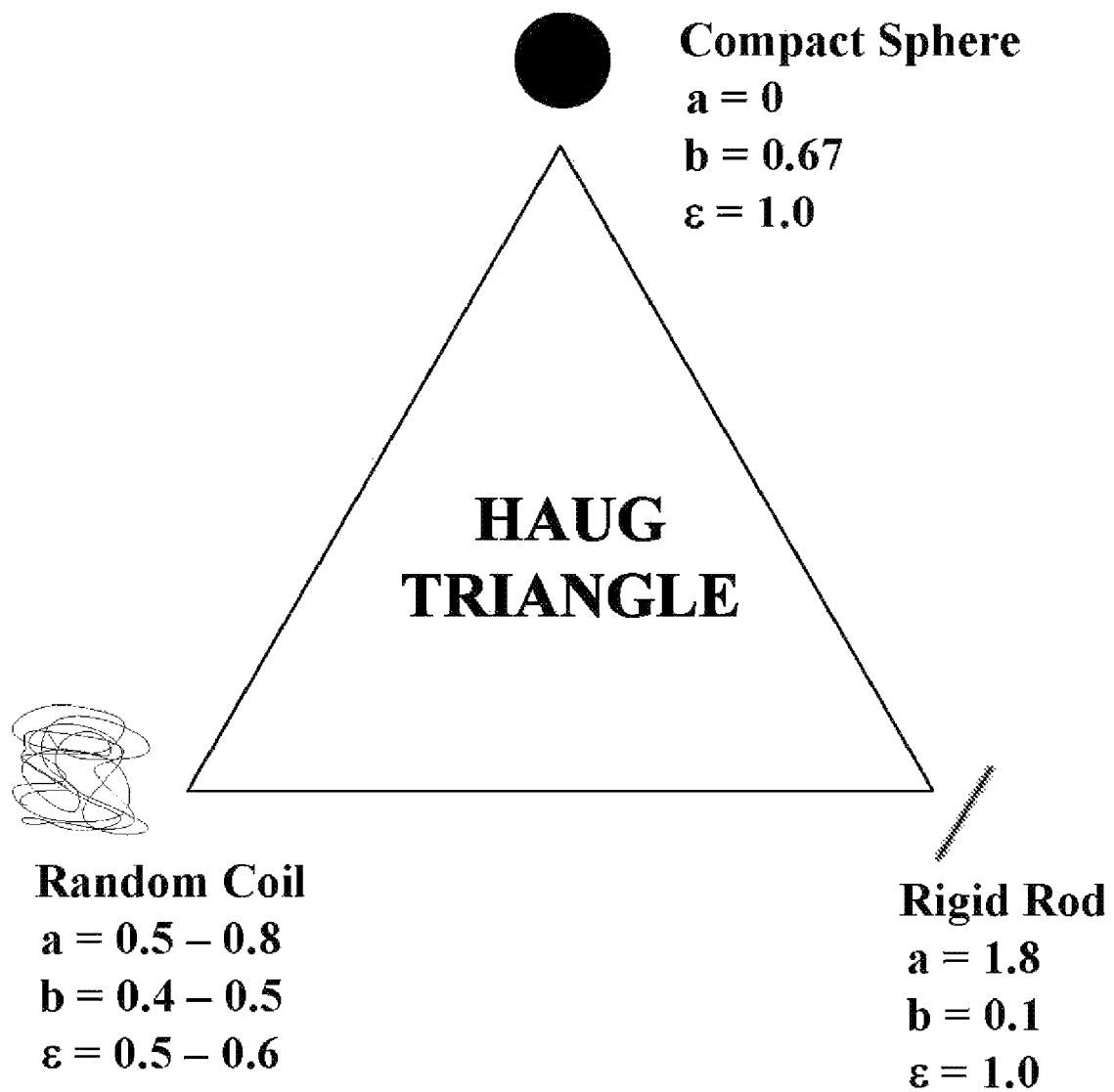
FIG. 1 depicts the Haug triangle of macromolecular conformations, showing a compact sphere at the top vertex of the triangle, random coils at the left hand vertex and rigid rod at the right hand vertex.

The inventors have found that chitosan can be subjected to certain treatments and/or modifications that are capable of producing a chitosan material having altered physical, chemical, and/or performance properties or characteristics. The inventors have also found that formulations including these treated chitosans, modified chitosans, or modified and treated chitosans have altered, tailored, and improved properties and/or characteristics of corresponding untreated chitosan formulations. The inventors have also found that these treated chitosans, modified chitosans, or modified and treated chitosans are ideally well suited for use as bioadhesive compositions, and/or drug delivery compositions or systems, and/or general purpose adhesive compositions or systems, and/or filler or bulking compositions or systems, etc. The inventors have found that the compositions of the present invention show different or improved properties over competing technologies. The inventors have found that the adhesive properties of the compositions of this invention allow the materials to reside on or in a target tissue or organ for an extended period of time without detrimental consequences to the tissue or organ. The inventors have also found that the use of cleavable or non-cleavable linkers attached to the compositions of this invention, provides a means to deliver a biological agent. The cleavable linkers can result in release of the biological agent in situ, the release being caused by hydrolytic, photolytic, enzymatic or a combination of hydrolytic, photolytic and enzymatic activity. The biological agent may be a biocide, a pharmaceutical, a nutraceutical, etc. and may be released via hydrolysis, via photolysis, via enzymatic activity or a combination of hydrolysis, photolysis and enzymatic activity. In the case of enzymatic release, the enzymes can be constitutive or inducible or the release enzyme can be incorporated into the composition itself.

Treated Chitosans

The present invention broadly relates to novel biomaterials including a chitosan composition comprising treated chitosan, modified chitosan, modified and treated chitosan or mixtures thereof. The treatment includes at least dialysis designed to cause a conformational and/or functional change of chitosan. The modification includes at least (i) a covalent modification of the chitosan with one or a plurality of chemical modifier or entities, (ii) a non-covalent association of the chitosan with one or a plurality of chemical entities, (iii) a coaddition of the chitosan with one or a plurality of chemical entities or (iv) mixtures or combinations thereof. The chemical entities or modifiers can be atomic structures such as atomic clusters, quantum dots, or other nano-atomic structures or molecules, molecular structures, or collections of molecules.

The present invention also broadly relates to novel adhesive compositions or systems including an effective amount of a treated chitosan, modified chitosan, modified and treated chitosan or mixtures or combinations thereof, where the adhesive compositions have different or improved adhesive properties relative to an adhesive composition including an equivalent amount of a corresponding untreated chitosan. The term mixture here means that the components have been mixed together, while the term combination means that the components are combined into discrete sections within the composition such as layers, strips, etc.

The present invention also broadly relates to novel drug delivery compositions or systems including an effective amount of a treated chitosan, a modified chitosan, modified and treated chitosan or mixtures or combinations thereof, where the compositions have different or improved drug delivery properties relative to a drug delivery composition including an equivalent amount of a corresponding untreated chitosan.

The present invention also broadly relates to novel drug delivery compositions or systems including a chitosan composition comprising a treated chitosan, modified chitosan, modified and treated chitosan or mixtures or combinations thereof and an effective amount of one biological agent such as a pharmaceutical agent or a plurality of biological agents, where the effective amount is sufficient to invoke a desired therapeutic effect and where the systems have different or improved drug delivery properties relative to a drug delivery composition or system including an equivalent amount of a corresponding untreated chitosan. The compositions of this invention including the chitosan matrix are capable of increasing a tissue drug concentration compared to a composition in the absence of the chitosan matrix at an equivalent drug concentration in the composition. Thus, the compositions of this invention afford a lower pharmaceutically effective amount of the drug compared to the composition in the absence of the chitosan matrix. In certain embodiments, the drug delivery compositions of this invention achieve a lower pharmaceutically effective amount than comparable compositions in the absence of the chitosan compositions. In certain embodiments, the lower pharmaceutically effective amount is at least 10% less than an amount of the drug in a comparable composition in the absence of the chitosan matrix. In other embodiments, the lower pharmaceutically effective amount is at least 20% less than an amount of the drug in a comparable composition in the absence of the chitosan matrix. In other embodiments, the lower pharmaceutically effective amount is at least 30% less than an amount of the drug in a comparable composition in the absence of the chitosan matrix. In other embodiments, the lower pharmaceutically effective amount is at least 40% less than an amount of the drug in a comparable composition in the absence of the chitosan matrix. In other embodiments, the lower pharmaceutically effective amount is at least 50% less than an amount of the drug in a comparable composition in the absence of the chitosan matrix. In other embodiments, the lower pharmaceutically effective amount is at least 60% less than an amount of the drug in a comparable composition in the absence of the chitosan matrix. In other embodiments, the lower pharmaceutically effective amount is at least 70% less than an amount of the drug in a comparable composition in the absence of the chitosan matrix. In other embodiments, the lower pharmaceutically effective amount is at least 80% less than an amount of the drug in a comparable composition in the absence of the chitosan matrix. In other embodiments, the lower pharmaceutically effective amount is at least 90% less than an amount of the drug in a comparable composition in the absence of the chitosan matrix. In other embodiments, the lower pharmaceutically effective amount is at least 95% less than an amount of the drug in a comparable composition in the absence of the chitosan matrix.

The present invention also broadly relates to novel drug delivery compositions or systems including a treated chitosan, a modified chitosan, modified and treated chitosan or mixtures or combinations thereof, where at least one chitosan includes an effective amount of one biological agent such as a pharmaceutical agent or a plurality of biological agents via labile linkages covalently bonded to sites or moieties in the chitosan, where the effective amount is sufficient to invoke a desired therapeutic effect, where the linkages are hydrolytically and/or enzymatically labile releasing the biological agent over a designed time period at a designed rate and where the compositions have different or improved drug delivery properties relative to a drug delivery system including an equivalent amount of a corresponding untreated chitosan.

The present invention also broadly relates to a method including the step of applying an effective amount of an adhesive composition including a treated chitosan, a modified chitosan, modified and treated chitosan or mixtures or combination thereof to a site of a first substrate. After application, the site is contacted with a site of a second substrate, where the contacting is for a time, at a temperature, at a pressure and at a humidity sufficient to allow the adhesive composition to bond the substrate sites together with a force greater than an adhesive system prepared with a corresponding untreated chitosan. The substrates can be living tissue and/or non-living substrates.

The present invention also broadly relates to a method including the step of applying an effective amount of an adhesive composition including a treated chitosan, a modified chitosan, modified and treated chitosan or mixtures or combinations thereof to a site of a substrate, where the contacting is sufficient to allow the adhesive composition to bond the substrate with a force greater than an adhesive system prepared with a corresponding untreated chitosan. The substrate can be living tissue and/or non-living substrates.

The present invention also broadly relates to a method for treating chitosan including dissolving raw chitosan (untreated chitosan) in an aqueous acid solution for a time and at a temperature sufficient to facilitate complete chitosan dissolution. Next, the dissolved chitosan is precipitated with a base. The acid dissolution and base precipitation can be performed more than once. The precipitated chitosan is then separated from the supernatant via centrifugation or other similar process for separating solid and liquid components. The chitosan is then placed in dialysis tubes and dissolved using an acid solution. After dissolution in the dialysis tubes, the chitosan is dialyzed against a solution which causes substantially reversible changes to the chitosan as evidenced by changes in certain physical, chemical and performance properties or characteristics compared to a corresponding untreated chitosan. The chitosan can be chemically modified prior to or after the dialysis steps.

The present invention also broadly relates to a method for treating chitosan including dissolving raw chitosan in an aqueous acid solution for a time and at a temperatures sufficient to facilitate complete chitosan dissolution. After the chitosan is dissolved, a base is added slowly to the dissolved chitosan to precipitate the chitosan, where the base addition raises a pH of the solution to a value between about pH 9 and pH 10. After base treatment, the chitosan is re-solubilized in an aqueous acid solution and then re-precipitated via the addition of a base. The re-precipitated chitosan is then separated from the solution by centrifugation. Next, the precipitated chitosan is dialyzed in an acid solution for a time and at a temperature sufficient to dissolve the chitosan and then dialyzed against a buffered salt solution, which changes certain physical and/or chemical properties of the chitosan. The resulting treated chitosan can then be freeze dried. Typically prior to the first base addition, the chitosan can be chemically modified. However, chemical modification can also be performed after base addition and even after re-constitution from a freeze dried material. Additionally, coadditions or the incorporation of other materials or components can be made at various steps in the treatment method.

In all of the compositions of this invention, the compositions can also include excipients, adjuvants, preservatives, buffers, vehicles, and/or any other component to result in a formulation of a composition of this inventions with desired characteristics for a desired end use.

The present invention also relates to a composition including a treated chitosan, a modified chitosan, a modified and treated chitosan or a mixture or combination thereof, where each chitosan exhibits changes in one or more chemical, physical and/or performance properties or characteristics relative to a corresponding untreated chitosan. In certain embodiments, the composition also includes a solvent, where the treated chitosan, the modified chitosan, the modified and treated chitosan or the mixture thereof is present in a concentration between about 0.1 mg/mL and about 100 mg/mL and the solvent is present in an amount between about 90 and about 99.99 v/v percent. In other embodiments, the solvent is water and each chitosan is in the form of a hydrogel. In other embodiments, the composition also includes an effective amount of a biological agent. In other embodiments, the composition also includes an effective amount of a biological agent and the solvent is water and each chitosan is in the form of a hydrogel. In certain embodiments, the concentration of the treated chitosan, the modified chitosan, the modified and treated chitosan or the mixture thereof is between about 1 mg/mL and about 50 mg/mL and the solvent is present in an amount between about 95 and about 99.9 v/v percent. In other embodiments, the concentration of the treated chitosan, the modified chitosan, the modified and treated chitosan or the mixture thereof is between about 3 mg/mL and about 30 mg/mL, and the solvent is present in an amount between about 97 and about 99.7 v/v percent. In other embodiments, each modified chitosan includes a functionalizing effective amount of one functional group or a plurality of functional groups covalently bonded to amine or alcohol moieties of the chitosan, where the functionalizing effective amount is between about 0.01% and about 100% of the amine or alcohol moieties of the chitosan and where the functional group or groups are the same or different in each modified chitosan. In other embodiments, the functionalizing effective amount is between about 0.1% and about 10% of the amine or alcohol moieties of the chitosan. In other embodiments, the functionalizing effective amount is between about 0.5% and about 2% of the amine or alcohol moieties of the chitosan. In other embodiments, the functional groups are selected from the group consisting of hydrophobic functional groups, hydrophilic functional groups, ionic functional groups and mixtures thereof. In certain embodiments, the hydrophobic functional groups are selected from the group consisting of alkyl groups, alkenyl groups, aryalkyl groups, alkaryl groups, and mixtures thereof having between 1 and 100 carbon atoms, where one or more of carbon atoms of the groups are replace by a hetero atom and/or hetero atom moieties selected from the group consisting of boron atoms, nitrogen atoms, oxygen atoms, sulfur atoms, silicon atoms, germanium, ester moiety, amide moiety, urea moiety, urethane moiety, and mixtures or combinations thereof and where one or more of the hydrogen atoms are replaced by a hetero atom and/or hetero atom moieties selected from the group consisting of halogen atoms, an alkoxide groups, an amide group, and mixtures or combinations thereof. In other embodiments, the hydrophobic functional groups are selected from the group consisting of carboxyl acids, organo sulfonic acids, polyethers, polyether amines, sterols, porphyrins and mixtures or combinations thereof. In certain embodiments, the hydrophilic functional groups are selected from the group consisting of diamines, polyamines, diols, polyols, diacids, polyacids, crown ethers, glymes, polyalkenylethers, polyalkenylamines, polyalkenyletheramines, polyacrylic acids, polyvinylalcohols, or mixtures or combinations thereof. In certain embodiments, the ionic functional groups are selected from the group consisting of a metal salt, an ammonium salt, a phosphonium salt, a sulfate salt, a carboxylic acid salt, a phosphate salt, dicarboxylic acids, poly carboxylic acids, where one carboxylic acid is used to form a covalent linkage with chitosan and the other acid groups can take a charge, diamines, poly amines, where one amine is used to form a covalent linkage with chitosan and the other amino groups can take a charge, metal ions, ionic atomic clusters, ionic molecular structures, simple anions, polyatomic anions, deprotonated oxoacids, substituted deprotonated oxoacids or deprotonated organic acids where these groups interact with the chitosan via an electrostatic interaction, and mixtures or combinations thereof. In other embodiments, the compositions can also include buffers, vehicles, additives, preservatives, excipients, adjuvants, or any other component that will render the composition suitable for a particular purpose. In any of the above compositions, any amounts of other components can be added to the compositions.

The present invention also relates to a composition comprising a treated chitosan, a modified chitosan, a modified and treated chitosan or a mixture thereof. Each of these chitosans exhibits changes in one or more chemical and/or physical properties and in performance properties and characteristics relative to a corresponding untreated chitosan. Each treated chitosan is prepared by dialyzing a solubilized chitosan against water, a salt solution and/or an anionic solution. While each modified chitosan is prepared by forming covalent linkages between the chitosan and one functional group or a plurality of functional groups, by forming non-covalent associations between the chitosan and one atomic or molecular agent or a plurality of atomic and/or molecular agents, or by forming mixtures between the chitosan and one atomic or molecular agent or a plurality of atomic and/or molecular agents altering the chitosan through covalent attachments of one functional group or a plurality of functional groups, non-covalent associations with one atomic or molecular agent or a plurality of atomic and/or molecular agents, and/or coadditions of one atomic or molecular agent or a plurality of atomic and/or molecular agents. The atomic and/or molecular agents are selected to impart to the chitosan a desired behavior, property or characteristic for a given application. In certain embodiments, the composition is in the form of a liquid, a solid, a dispersion, a suspension, a hydrogel, a particle, a nanoparticle, a thin film, or a shaped structure. In other embodiments, the compositions include a biological agent, where the composition is capable of releasing an effective amount of the agent into a site of organism over a desired period of time. In other embodiments, the agent is covalently bonded to at least one of the chitosans in the composition either directly or through a linker moiety, where the composition is capable of releasing an effective amount of the agent into a site of an organism over a period of time and where the period of time depends either on a rate of hydrolytic cleavage, enzymatic cleavage or a combination of hydrolytic cleavage and enzymatic cleavage of the agent from the at least one of the chitosans.

The present invention also relates to an adhesive composition comprising a treated chitosan, a modified chitosan, a modified and treated chitosan or a mixture thereof, where each treated and each modified chitosan exhibit changes in one or more chemical, physical and/or performance properties or characteristics relative to a corresponding untreated chitosan. In certain embodiments, the compositions also include an additive package adapted to render the composition suitable for a desired adhesive purpose. In other embodiments, the additive package comprises a biocompatible filler, an adhesive augmenting agent, or mixtures thereof.

The present invention also relates to a filler composition comprising a modified chitosan, a modified and treated chitosan or a mixture thereof, where each chitosan absorbs and retains water to a greater extent than a corresponding untreated chitosan. In certain embodiments, the composition also includes an additive package adapted to enhance the filler properties of the filler composition. In other embodiments, the additive package comprises a biocompatible filler, a water retention additive, or mixtures thereof.

The present invention also relates to a method of bonding tissue comprising the step of applying to a surface of a tissue site an effective amount of an aqueous treating solution comprising chitosan composition to form a coated surface. The chitosan composition comprises a treated chitosan, a modified chitosan, a modified and treated chitosan or a mixture thereof, where each chitosan exhibits changes in one or more chemical, physical and/or performance properties or characteristics relative to a corresponding untreated chitosan. The chitosan composition adheres to the surface with sufficient bond strength and sufficient retention to the surface to persist on the surface for a desired period of time. In certain embodiments, the method also includes the step of contacting the coated surface with a surface of a substrate, where the contacting is for a time, at a temperature, at a pressure and at a humidity sufficient to allow the chitosan composition to bond the tissue site surface to the substrate surface with a force greater than a chitosan composition comprising corresponding untreated chitosans. In certain embodiments, the substrate is a second tissue site. In other embodiments, the substrate is a synthetic material, a biological material or a mixture thereof. In certain embodiments, each modified chitosan includes a functionalizing effective amount of one functional group or a plurality of functional groups covalently bonded to amine or alcohol moieties of the chitosan, where the effective amount is sufficient to change one or more properties of the chitosan and where the functional group or groups are the same or different in each modified chitosan. In certain embodiments, the functionalizing effective amount is between about 0.01% and about 100% of the amine or alcohol moieties of the chitosan. In other embodiments, the functionalizing effective amount is between about 0.1% and about 10% of the amine or alcohol moieties of the chitosan. In other embodiments, the functionalizing effective amount is between about 0.5% and about 2% of the amine or alcohol moieties of the chitosan. In other embodiments, the functional groups are selected from the group consisting of hydrophobic functional groups, hydrophilic functional groups, ionic functional groups, quantum dots, atomic clusters, NMR active groups, fluorescent groups, dyes, and mixtures thereof. In certain embodiments, the hydrophobic functional groups are selected from the group consisting of alkyl groups, alkenyl groups, aralkyl groups, alkaryl groups, and mixtures thereof having between 1 and 100 carbon atoms, where one or more of carbon atoms of the groups are replace by a hetero atom and/or hetero atom moieties selected from the group consisting of oxygen atoms, sulfur atoms, silicon atoms, germanium, ester moiety, amide moiety, urea moiety, urethane moiethyl, and mixtures or combinations thereof and where one or more of the hydrogen atoms are replaced by a hetero atom and/or hetero atom moieties selected from the group consisting of halogen atoms, an alkoxide groups, an amide group, and mixtures or combinations thereof. In other embodiments, the hydrophobic functional groups are selected from the group consisting of carboxyl acids, organo sulfonic acids, polyethers, polyether amines, sterols, porphyrins and mixtures or combinations thereof. In certain embodiments, the hydrophilic functional groups are selected from the group consisting of diamine, polyamines, diols, polyols, diacids, polyacids, crown ethers, glymes, polyols, polyamines, polyalkenylethers, polyalkenylamines, polyalkenyletheramines, polyacrylic acids, polyvinylalcohols, or mixtures or combinations thereof. In certain embodiments, the ionic functional groups are selected from the group consisting of a metal salt, an ammonium salt, a phosphonium salt, a sulfate salt, a carboxylic acid salt, a phosphate salt, dicarboxylic or poly carboxylic acids, where one carboxylic acid is used to form a covalent linkage with chitosan and the other acid groups can take a charge, diamines or poly amines, where one amine is used to form a covalent linkage with chitosan and the other amino groups can take a charge, metal ions, ionic atomic clusters, ionic molecular structures, simple anions, polyatomic anions, deprotonated oxoacids, substituted deprotonated oxoacids or deprotonated organic acids where these groups interact with the chitosan via an electrostatic interaction, and mixtures or combinations thereof. In other embodiments, each chitosan in the chitosan composition is in the form of a hydrogel and the chitosan composition is present in a concentration between about 0.1 mg/mL and about 100 mg/mL and water is present in an amount between about 90 and about 99.99 v/v percent. In other embodiments, the chitosan composition is present in a concentration between about 1 mg/mL and about 50 mg/mL and the solvent is present in an amount between about 95 and about 99.9 v/v percent. In other embodiments, the chitosan composition is present in a concentration is between about 3 mg/mL and about 30 mg/mL, and the solvent is present in an amount between about 97 and about 99.7 v/v percent. In other embodiments, the chitosan composition further comprises an effective amount of a biological agent. In certain embodiments, each chitosan in the chitosan composition is in the form of a hydrogel and the chitosan composition is present in a concentration between about 0.1 mg/mL and about 100 mg/mL and the solvent is present in an amount between about 90 and about 99.99 v/v percent. In other embodiments, the chitosan composition is present in a concentration is between about 1 mg/mL and about 50 mg/mL and the solvent is present in an amount between about 95 and about 99.9 v/v percent. In other embodiments, the chitosan composition is present in a concentration is between about 3 mg/mL and about 30 mg/mL, and the solvent is present in an amount between about 97 and about 99.7 v/v percent.

The present invention also relates to a process for making a delivery composition including mixing a composition comprising a treated chitosan, a modified chitosan, a modified and treated chitosan or a mixture thereof with an effective amount of one biological agent or a plurality of biological agents under conditions sufficient to form a substantially uniform delivery composition. Each chitosan exhibits changes in one or more chemical, physical and/or performance properties or characteristics relative to a corresponding untreated chitosan.

The present invention also relates to a process for making a biological agent delivery composition including contacting a composition comprising a treated chitosan, a modified chitosan, a modified and treated chitosan or a mixture thereof with an effective amount of one biological agent or a plurality of biological agents. Each chitosan exhibits changes in one or more chemical, physical and/or performance properties or characteristics relative to a corresponding untreated chitosan. Each agent includes a functional group adapted to react with sites on the treated chitosans to form covalent linkages under conditions to form the covalent linkages between the chitosan and each biological agent to form an extended release, biological delivery composition. The linkages are cleavable via hydrolysis, via enzymatic activity or via a combination of hydrolysis and enzymatic activity.

The present invention also relates to a process for making a biological agent delivery composition including contacting a composition comprising a treated chitosan, a modified chitosan, a modified and treated chitosan or a mixture thereof with an effective amount of one biological agent or a plurality of biological agents under conditions to prepare a substantially uniform drug delivery composition. Each chitosan exhibits changes in one or more chemical, physical and/or performance properties or characteristics relative to a corresponding untreated chitosan. The biological agents are covalently bonded to some or substantially all reactive groups on the chitosan. The drug delivery composition is capable of releasing an effective amount of the biological agent over a period of time via hydrolysis, via enzymatic activity or via a combination of hydrolysis and enzymatic activity.

The present invention also relates to a composition including a treated chitosan, a modified chitosan, a modified and treated chitosan or a mixture thereof. The treatment includes at least dialyzing an untreated chitosan or a modified untreated chitosan under conditions sufficient to change one or more chemical, physical and/or performance properties or characteristics of each chitosan relative to a corresponding untreated chitosan. The modification includes (i) forming covalent linkages between the chitosan and one functional group or a plurality of functional groups, (ii) forming non-covalent associations between the chitosan and one atomic or molecular agent or a plurality of atomic and/or molecular agents, (iii) forming mixtures between the chitosan and one atomic or molecular agent or a plurality of atomic and/or molecular agents, or (iv) a mixtures or combination of these three modification types.

The present invention also relates to a drug delivery system including a treated chitosan, a modified chitosan, a modified and treated chitosan or a mixture thereof, where each chitosan and each modified chitosan exhibit changes in one or more chemical, physical and/or performance properties or characteristics relative to a corresponding untreated chitosan. The chitosan has covalently bonded to sites in the chitosan a pharmaceutically effective amount of one pharmaceutical agent or a plurality of pharmaceutical agents via labile linkages. The pharmaceutically effective amount is sufficient to invoke a desired therapeutic effect. The linkages are hydrolytically labile, enzymatically labile or hydrolytically and enzymatically labile releasing the pharmaceutical agent over a designed time period at a designed rate. The system has different or improved drug delivery properties relative to a drug delivery system including an equivalent amount of a corresponding untreated chitosan.

The present invention also relates to a method comprising the steps of applying an effective amount of an adhesive system comprising a treated chitosan, a modified chitosan, a modified and treated chitosan or a mixture thereof to a site of a first substrate. Each treated chitosan and each modified chitosan exhibit changes in one or more chemical, physical and/or performance properties or characteristics relative to a corresponding untreated chitosan. The method also includes the step of contacting the site with a corresponding site of a second substrate, where the contacting is for a time, at a temperature, at a pressure and at a humidity sufficient to allow the adhesive system to bond the substrate sites together with a force greater than an equivalent adhesive system prepared with corresponding untreated chitosan. In certain embodiments, the substrates are living tissue or a living tissue and a patch material.

The present invention also relates to a method comprising the step of applying an effective amount of an adhesive system comprising a treated chitosan, a modified chitosan, a modified and treated chitosan or a mixture thereof to a site of a substrate. Each treated chitosan and each modified chitosan exhibit changes in one or more chemical, physical and/or performance properties or characteristics relative to a corresponding untreated chitosan. The contacting is sufficient to allow the adhesive system to bond the substrate with a force greater than an equivalent adhesive system prepared with corresponding untreated chitosan. In certain embodiments, the substrates are living tissue or a living tissue and a patch material.

The present invention also relates to a method for treating chitosan including dissolving a raw chitosan in a first aqueous acid solution for a time and at a temperatures sufficient to facilitate complete chitosan dissolution. A base is added to the dissolved chitosan solution to precipitate the chitosan, where the base addition raises a pH of the dissolved chitosan solution to a value between about pH 9 and about pH 10. The precipitated chitosan is re-dissolved in a second aqueous acid solution. Then, a base is added to the redissolved chitosan solution to precipitate the chitosan. The re-precipitated chitosan solution is centrifuged to separate the chitosan from the solution. The re-precipitated chitosan is dialyzed in an acid solution for a time and at a temperature sufficient to dissolve the chitosan in a dialysis tube. The acid dialyzed chitosan is then dialyzed against a buffered salt solution, which changes one or more chemical, physical and/or performance properties or characteristics relative to a corresponding untreated chitosan or modified chitosan. In certain embodiments, the method can also include freeze drying the dialyzed chitosan to form a chitosan having a lower apparent molecular weight and a higher tissue bond strength than a corresponding untreated chitosan. In other embodiments, the method can also include prior to first base addition step, chemically modifying the chitosan. In other embodiments, the chemical modification can be performed at any stage the process, e.g., to the raw chitosan, to the water dialyzed chitosan, to the acid dialyzed chitosan, to the freeze dried chitosan or to the re-constituted chitosan. In other embodiments, the method can also include prior to freeze drying, adding an additive package to the dialyzed chitosan. In other embodiments, the additive package can be added at any stage of the process, e.g., to the raw chitosan, to the water dialyzed chitosan, to the acid dialyzed chitosan, to the freeze dried chitosan or to the re-constituted chitosan. Of course, where to add the additive package will depend on the additives and where they would be capable of surviving certain of the process step. Thus, if the additive package would be lost during dialysis, then the additive package would have to be added post dialysis; similarly, if the additive package would be changed or lost during chemical modification, then the additive package would have to be added post modification. One of ordinary skill in the art should recognize that the order of process steps more depends on the desired material than on a required procedure. Thus, if the composition requires the change in chitosan afforded by the dialysis step that changes its apparent molecular weight, then the process steps will be arranged to accomplish that end. Otherwise, the process steps will be arranged to impart to the compositions a set of desired properties or characteristics.

The present invention also relates to composition including a linkage between a protein and a biological agent created by the photoactivation of a naphthalimide group. The composition is designed to release the biological agent of over a period of time due to hydrolysis, photolysis and/or enzymatic cleavage of the naphthalimide linkage. The present invention also relates to a method of bonding a biological agent to a protein comprising the step of forming a linkage between a protein and a biological agent by photoactivation of a naphthalimide group, where the linkage releases a biological agent over a period of time due to hydrolysis, photolysis and/or enzymatic activity.

The present invention also relates to a method for making a tethered biological agent comprising the step of contacting a chitosan composition comprising a treated chitosan, a modified chitosan, a modified and treated chitosan or a mixture or combination thereof with a biological agent under conditions adapted to form a linkage between a moiety on the chitosan or chitosans and a moiety the biological agent, where linkage is non-susceptible to hydrolytic, photolytic or enzymatic cleavage. In certain embodiments, the linkage is a direct linkage between the two moieties or the linkage comprises a linker interposed between the two moieties.

History of Invention

The inventors' first attempt at a modified chitosan was to prepare chitosan modified with a naphthalimide, resulting in a light activated material displaying greater bond strength than chitosan alone. See U.S. patent application Ser. No. 10/982,197, incorporated herein by reference.

As the inventors began to optimize the naphthalimide modified chitosan, it was discovered that dialysis versus phosphate buffered saline greatly increased bond strengths of bioadhesives derived from the naphthalimide modified chitosan as well as native chitosan.

It was noted that the naphthalimide modified chitosan demonstrated bonding in the absence of light. Therefore, the inventors began to explore the possibility of modifying chitosan with organic molecules to enhance certain characteristics or qualities of chitosans. Through the same iterative process, it was discovered that the binding ability of both native and modified chitosan was greatly enhanced. In some cases, certain modifications may convey additional biocompatibility, desirable degradation profiles, or other desirable traits to the resulting modified chitosan formulations.

The inventors have found that the methods of this invention provide unique chitosan materials. Native chitosan is typically found to be in a molecular form that places it near the random coil/rigid rod region of the Haug triangle of macromolecular conformations as shown in FIG. 1. The experimental data shown below demonstrate that treated chitosan, modified chitosan, modified and treated chitosan or mixtures or combinations thereof prepared according to the methods of this invention evidence a reduction in measured molecular weight as compared to untreated chitosan. As shown in the Haug triangle in FIG. 1, the inventors believe, without being bound to any particular theory or theoretical explanation, that this shift to lower apparent molecular weight, which is substantially reversible, is due to a change in a conformation of the chitosan molecule from a random coil to a more compact spherical conformation. Thus, the inventors believe that the chitosan molecular conformation moves from the left vertex of the Haug triangle towards the top vertex of the Haug triangle.

Analytical characterization supports the premise of a contraction of the 3D chitosan chemical structure of the molecule to give a more compact 3D conformation and/or structure. While not meaning to be bound by any theory, the inventors believe that this observable change in chitosan molecular form may be responsible for the improved bioadhesive properties obtained using the treated chitosan, a modified chitosan, modified and treated chitosans or mixtures or combinations thereof of this invention as compared to corresponding untreated chitosans.

This invention involves the treatment or modification and treatment of chitosan for use as an adhesive for general purpose applications and as an adhesive system for medical applications, especially, medical applications involving tissue bonding. The compositions of this invention including a treated, modified, modified and treated chitosans or mixtures or combinations thereof are also well suited as a means for local drug delivery. The treated, modified, modified and treated chitosans or mixtures or combinations of this invention are also well suited for filling, bulking or reconstructive procedures.

Chitosan contains a wealth of hydroxy and amino functional groups which makes it an ideal candidate for chemical modification. The present invention utilizes the inherent nucleophilicity of its amino functionality as sites for coupling or attaching a wide range of chemical moieties via formation of sulfonamide and amide linkages or other similar nitrogen containing chemical linkages such as urethane linkages, urea linkages, thiourea linkages, or the like. The present invention details the use of organic acid chloride, sulfonic acid chloride and diimide coupling reagents to produce desired chemical modifications. Any appropriate reaction methodology known to one skilled in the art utilizing amino functionalities on a substrate could be used to implement such modification.

During the development of this invention, it was discovered that a treated chitosan, a modified chitosan, a modified and treated chitosan or mixtures or combinations thereof, where modification involves the covalent attachment or co-addition of chemical entities into the chitosan structure, provides unique biomaterials with different and often times favorable functional characteristics for a number of potential uses. These uses include novel adhesive systems, novel means for local drug delivery systems, and novel filling or bulking systems. Although currently the focus of the inventions is on biomedical applications, the adhesive system may find wider applications especially in binding a non-living substrate to a living substrate or another non-living substrate or to serve as a coating of a non-living substrate in order to confer enhanced biocompatibility or other desirable traits.

The inventors have found that novel chitosan based adhesive compositions or systems can be formulated that has much superior tissue bonding properties as compared to native or untreated chitosan. The inventors have also found that chitosan used in the formulation of the novel chitosan based adhesive compositions or systems of this invention have properties that distinguish them from normal, native, untreated or unprocessed chitosan permitting clear differential analytical characterization of the chitosans of this invention and the adhesives formulated therefrom. The inventors have also shown that certain altered physical and/or chemical characteristics of the chitosan are reversible. Thus, these transformations do not appear to destroy or fundamentally alter the basic chemical nature of the chitosan, just substantially alter the properties of the treated chitosan relative to untreated chitosan. The inventors have also found that novel drug delivery matrices can be formulated that offers superior retention of the formulation and improved bioavailability of the desired pharmaceutical agent, meaning that the compositions of this invention afford a similar therapeutic effect and/or similar bioavailability at lower drug concentrations compared to commercially available delivery compositions. Furthermore, the inventors have found that compositions of this invention demonstrate characteristics desirable for use as fillers or bulking agents in such fields as reconstructive surgery or cosmetic surgery. The compositions of this invention demonstrate very favorable biocompatibility within tissues generally augmented in reconstructive and cosmetic surgery. Thus, the compositions of this invention can be tailored so that the compositions have desired properties and characterizations.

Although in many embodiments of this invention, the compositions of this invention including treated, modified and/or modified and treated chitosans are reconstituted from a freeze dried state into an aqueous solution to form hydrogels, aqueous dispersions, aqueous suspensions, aqueous pastes or the like, the compositions can also be utilized directly in their freeze dried state. In such embodiments, the freeze dried materials can be dry mixed with other materials such as biological agents or fillers. The compositions can also be swelled, using water or an aqueous solution (incomplete dissolution) and mixed with other components. These materials can then be fully hydrated or reconstituted. The dry or swelled compositions of this invention can also be used directly, where the treated, modified and/or modified and treated chitosans form hydrogels in situ after the material containing the composition is implanted or placed in contact with tissues.

Suitable Reagents

Suitable amino acids for use in this invention include, without limitation, any naturally occurring or synthetic compound including a carboxylic group and an amino group in an alpha arrangement or any compound including a carboxylic group and an amino group capable of being incorporated into a polypeptide chain or a compound including a carboxylic acid analog or an amino group analog, where the compound is capable of being incorporated into a polypeptide chain.

Suitable polypeptides for use in this invention include, without limitation, any naturally occurring or synthetic compound comprising a chain of amino acids.

Suitable enzymes for use in this invention include, without limitation, any naturally occurring or synthetic compound comprised of amino acids and capable of catalyzing a chemical reaction.

Suitable ribozymes for use in this invention include, without limitation, any naturally occurring or synthetic compound comprised of nucleotides and capable of catalyzing a chemical reaction.

Suitable nucleotides for use in this invention include, without limitation, any naturally occurring or synthetic compound capable of being incorporated into a nucleotide chain.

Suitable oligonucleotides for use in this invention include, without limitation, any naturally occurring or synthetic compound comprising a relatively small number of nucleotides, generally between about 2 and about 20.

Suitable polynucleotides for use in this invention include, without limitation, any naturally occurring or synthetic compound comprising a large number of nucleotides, generally greater than about 20 to thousands.

Suitable nucleic acids for use in this invention include, without limitation, any naturally occurring or synthetic compound comprising two to millions of nucleotides or more.

Suitable hydrophobic groups for use in modifying the chitosans of this invention include, without limitation, alkyl group, alkenyl groups, alkynyl groups, aralkyl groups, and alkaryl groups, having between 1 carbon atom and about 100 carbon atoms. In these groups, one or more carbon atoms can be replaced by a hetero atom or a hetero atom containing group, where the hetero atoms are selected from the group consisting of oxygen, nitrogen, sulfur, silicon, germanium, gallium, and mixtures thereof and where the hetero atom containing groups are selected from the group consisting of an alkoxide group, a sulfide group, an amido group, a silicon containing group, and mixtures or combination thereof. In these groups, one or more of the hydrogen atoms can be replaced by a hetero atom or hetero atom containing group, where the hetero atoms are selected from the group consisting of a halogen atom and mixtures thereof and where the hetero atom containing group is selected from the group consisting of alkoxide groups, sulfide groups, and mixtures or combinations thereof.

Suitable hydrophilic groups for use in modifying the chitosans of this invention include, without limitation, any group or plurality of groups that enhance or change hydrophilic or hygroscopic properties of chitosan. Exemplary examples of such hydrophilic or hygroscopic groups include diamines, polyamines, diols, polyols, diacids, polyacids, crown ethers, glymes, polyalkenylethers, polyalkenylamines, polyalkenyletheramines, polyacrylic acids, polyvinylalcohols, or any other group that can enhance or change the hydrophilic or hygroscopic property of the chitosan, or mixtures or combinations thereof.

Suitable ionic groups for use in modifying the chitosans of this invention include, without limitation, any group or plurality of groups that enhance or change ionic properties of chitosan. Exemplary groups include dicarboxylic or poly carboxylic acids, where one carboxylic acid is used to form a covalent linkage with chitosan and the other acid groups can take a charge, diamines or poly amines, where one amine is used to form a covalent linkage with chitosan and the other amino groups can take a charge, metal ions, ionic atomic clusters, ionic molecular structures, simple anions, polyatomic anions, deprotonated oxoacids, substituted deprotonated oxoacids or deprotonated organic acids where these groups interact with the chitosan via an electrostatic interaction, any other charged group or mixtures or combinations thereof.

Suitable biological agents for use in the compositions of this invention include, without limitation, any bioactive agent that causes directly or indirectly a desired biological effect, or any compound that causes a desired biological, physiological, or other effects such as a protective coating, or the like. Exemplary biological agents include, without limitation, biocides, pharmaceuticals, nutraceuticals, or mixtures or combinations thereof. Biocides include, without limitation, a pesticide, an antimicrobial, a spermicide or mixtures or combinations thereof. Pesticides include, without limitation, fungicides, herbicides, insecticides, algicides, molluscicides, miticides and rodenticides. Antimicrobials include, without limitation, germicides, antibiotics, antibacterials, antivirals, antifungals, antiprotozoals and antiparasites. Pharmaceuticals include, without limitation, any compound given to an animal including a human to prevent or treat a disease, dysfunction, malady, or the like or to reduce or ameliorate symptoms of such disease, dysfunction, malady, or the like. Exemplary examples of pharmaceuticals include cardiac drugs; cardiovascular drugs; diuretics; psychotherapeutic drugs; gastrointestinal drugs; anti-cancer drugs; contraceptive drugs; ocular drugs; anti-inflammatory drugs; gastrointestinal tract pharmaceutical agents including, without limitation, antacids, antiemetics, $H_2$ antagonists, proton pump inhibitors, laxatives, antidiarrhoeals, etc. or mixtures or combinations thereof; blood and blood forming organ pharmaceutical agents including, without limitation, anticoagulants, antiplatelets, thrombolytics, etc. or mixtures or combinations thereof; cardiovascular system pharmaceutical agents including, without limitation, antiarrhythmics, antihypertensives, diuretics, vasodilators, antianginals, beta blockers, angiotensin converting enzyme inhibitors, antihyperlipidemics, etc. or mixtures or combinations thereof; skin pharmaceutical agents including, without limitation, emollients—antipruritics, etc. or mixtures or combinations thereof; reproductive system pharmaceutical agents including, without limitation, hormonal contraception, fertility agents, selective estrogen receptor modulators, sex hormones, etc. or mixtures or combinations thereof; endocrine system pharmaceutical agents including, without limitation, anti-diabetics, corticosteroids, sex hormones, thyroid hormones; pharmaceutical agents for infections and infestations including, without limitation, antibiotics, antivirals, vaccines, antifungals, antiprotozoals, antihelmintics, etc. or mixtures or combinations thereof; malignant and immune disease pharmaceutical agents including, without limitation, anticancer agents, immunostimulators, immunosuppressants, etc. or mixtures or combinations thereof; muscle, bone, and joint pharmaceutical agents including, without limitation, anabolic steroids, anti-inflammatories, antirheumatics, corticosteroids, muscle relaxants, etc. or mixtures or combinations thereof; ocular pharmaceuticals; brain and nervous system pharmaceutical agents including, without limitation, anesthetics, analgesics, anticonvulsants, mood stabilizers, anxiolytics, antipsychotics, antidepressants, nervous system stimulants, sedatives; respiratory system pharmaceutical agents including, without limitation, bronchodilators, decongestants, $H_1$ antagonists, etc. or mixtures or combinations thereof.

Synthetic Strategies of the Invention

General Procedure for Chitosan Dissolution

Chitosan was solubilized with a 10% organic acid or a non-oxidizing mineral acid solution. The organic acid or non-oxidizing mineral acid used was dependent upon the subsequent steps used to produce the invention and the final application of this invention. Non-limiting mineral acids include HCl, sulfuric acid, phosphoric acid or any other non-oxidizing mineral acid. Table I contains a non-limiting list of suitable organic acid choices for this process.

TABLE I

| Organic Acids For Chitosan Dissolution | |
|---|---|
| Acetic Acid | Butyric Acid |
| Lactic Acid | Pyruvic Acid |
| Tartaric Acid | Benzoic Acid |
| Citric Acid | Succinic Acid |
| Formic Acid | Trichloroacetic Acid |

The chitosan was allowed to solubilize overnight without mixing. After the chitosan was completely dissolved, the sample was placed on a mechanical mixer and stirred for about 30 minutes before proceeding to the next step. The sample was continuously stirred until the final base precipitation, which occurs at the end of the chitosan purification process.

Chitosan Modification (Optional)

If treated, but unmodified, chitosan was desired, this step in the synthetic protocol was skipped. If a modified and treated chitosan was desired, various chemical entities in a number of broad categories, tabulated in a non-limiting list in Table II can be used to modify the treated chitosan. These modifications can be performed at various point during the synthetic strategy. These moieties can be covalently attached to the chitosan substrate using, but not limited to, the linking chemistries provided in Table II or Examples 1-4 and 6. The degree of modification obtained was determined by the amount of modifier added in the modification step. If the modifier was not a liquid, it was dissolved in an appropriate solvent. The modifier was then slowly added to the stirred chitosan by dropwise addition. The modifier was allowed to mix with the chitosan for an appropriate period of time based upon the modifier selected.

TABLE II

Modification Classes and Chemistries

| Class | Attachment Type | Modifier Functionality | General Modifier Classes | Representative Modifier | Coupling Chemistry |
|---|---|---|---|---|---|
| A | Covalent to chitosan amine or alcohol | hydrocarbon, branched hydrocarbon, or substituted hydrocarbon | long chain fatty acid, organic sulfonic acids, organic acid chlorides, organic anhydrides, etc. | Octanesulfonic acid | Reactive anhydride, acid chloride or other activated acid or ester/amide coupling agent |
| B | Covalent to chitosan amine or alcohol | unsaturated or aromatic hydrocarbon | aromatic ring systems, porphyrins, etc. | Protoporphyrin IX | Reactive anhydride, acid chloride or other activated acid or ester/amide coupling agent |
| C | Covalent to chitosan amine or alcohol | polar or non-polar hydrocarbon | alkyl groups, alkenyl groups, alkynyl group, arenyl groups, aralkyl groups, alkaryl group, halogenated analogs, perhalogenated analogs, analogs having one or more hetero atoms, etc. | Perfluorooctane sulfonic acid | Reactive anhydride, acid chloride or other activated acid or ester/amide coupling agent |
| D | Covalent to chitosan amine or alcohol | sterol nucleus | sterols, steroids, etc. | Deoxycholic acid | Reactive anhydride, acid chloride or other activated acid or ester/amide coupling agent |
| E | Covalent to chitosan amine or alcohol | biomolecules | amino acids, polypeptides, enzymes, ribozymes, nucleic acids, nucleotides, plasmids, saccharides, polysaccharides, vitamins, minerals, etc. | Arginine | Reactive anhydride, acid chloride or other activated acid or ester/amide coupling agent |
| E' | Covalent to chitosan amine or alcohol | hydrophilic groups | polyalkyleneoxide carboxylic acids, diamines, polyamines, diols, polyols, diacids, poly acids, crown ethers, glymes, polyalkenylethers, polyalkenylamines, polyalkenyletheramines, polyacrylic acids, polyvinylalcohols, etc. | N-(2-Diethylamino-ethyl)-succinamic acid | Reactive anhydride, acid chloride or other activated acid or ester/amide coupling agent |
| E" | Covalent to chitosan amine or alcohol | ionic groups | metal salts, ammonium salts, phosphonium salts, sulfate salts, diamines, polyamines, diacids, polyacids, acrylic acid oligomers, polyacrylic acid, disulfonates, poly sulfonates, diphosphonates, poly phosphonates, etc. | Glutamic acid | Reactive anhydride, acid chloride or other activated acid or ester/amide coupling agent |
| F | Mixture | non-polar solvents, polar solvents, organic molecules, biomolecules | alkanes, alkenes, aromatics, plasticizers, amino acids, polypeptides, enzymes, ribozymes, nucleic acids, nucleotides, plasmids, saccharides, polysaccharides, vitamins, minerals, etc. | perfluorooctane, octane, perfluoron | NA |
| G | Treated | | NA | NA | NA |

While chitosan is amenable to a wide variety of modifications with a single atomic and/or molecular functional group or with a plurality of atomic and/or molecular functional groups, Table III tabulates a list of functional groups that have been used by the inventors to modify chitosan to achieve a change to a physical, chemical or functional property or characteristic of the chitosan. The term atomic functional group is meant to embrace the attachment of single atoms such as metal atoms or ions, the attachment of atomic clusters including homoatomic clusters or mixed atomic clusters, quantum dots, or any other small collection of atoms that may not evidence traditional molecular bonding.

TABLE III

A List of Specific Molecules Used to Modify Chitosan

Octane-sulfonic acid
1,1,2,2,3,3,4,4,5,5,6,6,7,7,8,8,8-Heptadecafluoro-octane-1-sulfonic acid
Succinic acid mono-[2-(6-ethylcarbamoyl-hex-2-enyl)-4-hydroxy-3-(3-hydroxy-5-phenyl-pent-1-enyl)-cyclopentyl] ester
Fluorescein isothiocyanate (FITC)
N-Hexyl-succinamic acid
N-Methyl-succinamic acid
N-Isopropyl-succinamic acid
N-Octyl-succinamic acid
N-Phenyl-succinamic acid
N-Benzyl-succinamic acid
Glycine ethyl ester
Arginine ethyl ester
Cysteine ethyl ester
Histidine ethyl ester
N-(2-Diethylamino-ethyl)-succinamic acid
N-(2-{2-[2-(2-{2-[2-(2-{2-[2-(2-Methoxy-ethoxy)-1-methyl-ethoxy]-1-methyl-ethoxy}-1-methyl-ethoxy)-1-methyl-ethoxy]-1-methyl-ethoxy}-1-methyl-ethoxy)-1-methyl-ethoxy]-1-methyl-ethoxy}-1-methyl-ethyl)-succinamic acid
Lactic acid
Protoporphyrin
Heme
Cholic acid
Deoxycholic acid
Steric acid
Oleic acid
Palmitic acid
Allantoic acid
3-indole lactic acid
Indole-3-butyne acid
3-Indole propionic acid
Pyruvic acid
3-Mercapto-propionic acid
α-Ketoglutaric acid
Oxaloacetic acid
Phenyl methyl sulfonic acid Base Treatment Base was slowly added to the chitosan sample until a pH between 9 and 10 was achieved (pH paper with a discernable color change between 9 and 10 was used). In addition to the mechanical stirring, a teflon stir rod was used to aid the mixing process during this step, as the chitosan solution became very viscous.

Chitosan Purification

The chitosan was resolubilized in acid by the addition of a 10% (v/v) organic acid solution. Resolubilization was allowed to take place overnight. After all chitosan had gone back into solution, the chitosan was reprecipitated by slowly adding base. Full precipitation was indicated by both the attainment of a basic pH (9-10) and the lack of any notable viscosity in the sample supernatant. The chitosan, including covalently modified chitosan, was precipitated in this step leaving small molecules, including unreacted modifying reagents, in solution. The mixer was removed from the sample and the sample was centrifuged (e.g., 3850×G or a sufficient G force to sediment the chitosan) and the supernatant discarded.

Dialysis

The solid chitosan from the centrifugation step was transferred to dialysis tubing (10 mm flat diameter, 12,000-14,000 MW cutoff). The chitosan was dialyzed against a 10% (v/v) organic acid solution until the solid was redissolved. The same acid chosen for the initial chitosan dilution was used in this step. However, depending on the use for which the final product is to be used, the acid can be different than the acid used in the initial dissolution steps and the choice will be influenced by the subsequent synthetic steps. Table I contains a non-limiting list of the possible acid choices. The acid dialysate was then removed and replaced with water and dialyzed for a time no shorter than 3 hours. The water was then replaced 2 additional times for a total of three water washes. A small amount of chitosan was removed from the dialysis tubing and the pH measured using a pH meter. The dialysate was then changed to a buffered salt solution and the dialysis was monitored until the pH of the chitosan was generally in the range of pH 5.7 to 6.0. The buffered salt solution used for dialysis was chosen based upon the final product application. Table IV contains a non-limiting list of the possible buffered salt solutions. Fresh buffered salt solution was used if the desired pH range was not achieved in a 3 hour period. The chitosan was then dialyzed 3 times against water with each wash lasting no less than 3 hours. The chitosan was removed from the dialysis tubing and combined in a freeze dry flask. Any of the wash steps described above can be comprise a single wash step or additional wash steps, where the number of washings per wash steps is more a matter of choice than necessity.

TABLE IV

Example Buffered Salt Solutions or Potential Components

| | |
|---|---|
| Phosphate Buffered Saline | Phosphate |
| Suberate | Adipate |
| Oxalate | Citrate |
| Succinate | Malate |
| Sulfate | HEPES |

Chitosan Freeze Drying

The flask containing dialyzed chitosan was placed in a −80° C. freezer overnight. The sample was then freeze dried and stored until use.

Chitosan Reconstitution

The final formulation was prepared by combining an amount of freeze dried chitosan of this invention with a volume of sterile phosphate buffered saline (PBS; pH=7.4) or other appropriate diluents that would yield the desired formulation concentration in milligrams chitosan per milliliter of PBS or other appropriate diluent. The sample was allowed to solubilize for at least four hours prior to sterilization, or for a time that is appropriate for the specific final formulation.

Sterilization

The chitosan formulation was steam sterilized in an autoclave. This was accomplished by tenting the sample vial with aluminum foil and placing the sample vial in a water bath inside the autoclave. After sterilization, the sample was allowed to cool to room temperature and a final pH was measured. The desired formulation pH is between about 5 and about 7. In certain embodiments, the pH range is between about 6 and about 7. In other embodiments, the pH range is between about 6.2 and about 6.4.

Addition of Non-Covalent Chemical Modifiers (Optional)

In all of the compositions of the invention, further manipulations of the chitosan properties may be achieved by the addition of one modifying reagent or a plurality of modifying reagents, where the reagents are designed to impart properties to the composition making the composition tailored for an intended purpose. These additions can occur at various points throughout the synthetic strategy. For example, for tissue adhesives, the additives may be anti-microbial agents, anti-viral agents, growth promoters, agents to enhance healing, or any other agent that can tailor the composition for a tissue adhesive purpose. For other types of adhesives, the additives may include other additives depending on the application. For drug delivery applications, the additives can be the active pharmaceutical agents if the pharmaceutical agents are not covalently bonded to the chitosan matrix or can be excipients, adjuvants, promoters, release promoters, or any other agent that can tailor the composition for the intended drug delivery application. These non-covalent modifications can influence the chitosan behavior by modulating or modifying intra- and inter-chain interactions. This is accomplished by combining appropriate volumes of sterile reconstituted chitosan and sterile modifying agents to yield the desired formulation. Suitable non-covalent modifiers include, without limitation, crosslinking agents, pharmaceutical compositions, hydrophobic molecules, hydrophilic molecules, dyes, steroids, lipids, proteins, nucleic acids, biocompatible polymers, or any other material that can be added to the chitosans of this invention.

Graphical Descriptions of Methods of this Invention

Figure 2A:
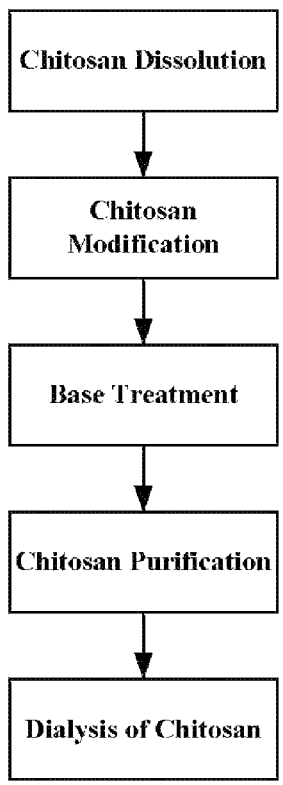
FIGS. 2A&B depict two schematic embodiments of chitosan treatment and/or modification methods of this invention.
Figure 2B:
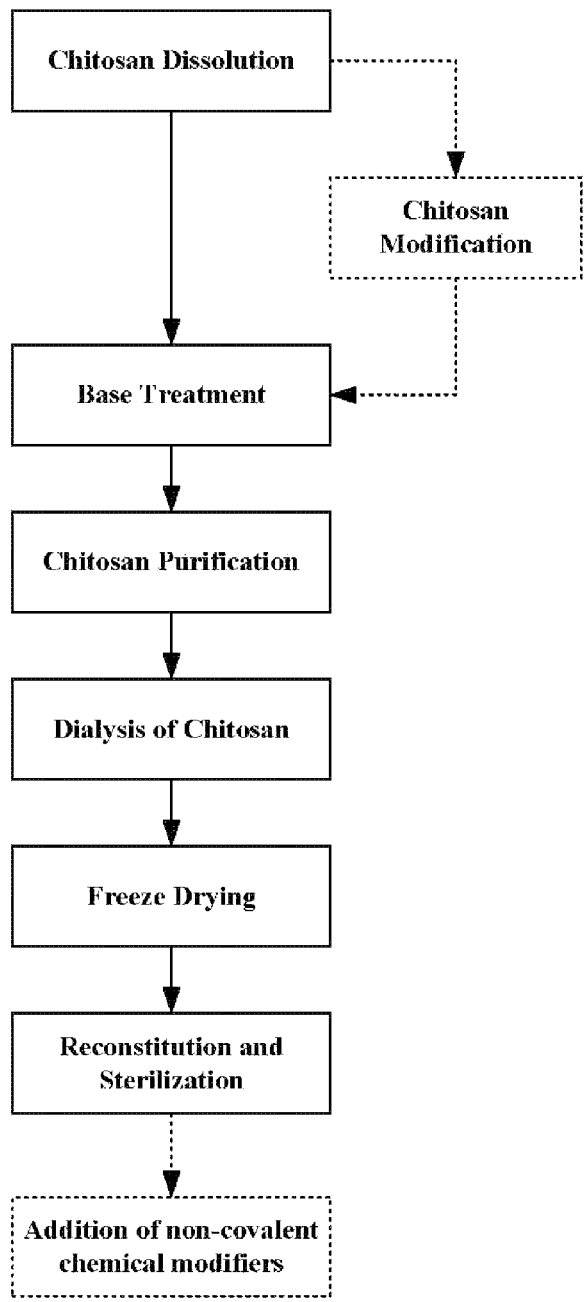

Certain embodiments of the method of this invention for the preparation of treated chitosan or modified and treated chitosan are shown in block diagram format in FIGS. 2A&B.

EXPERIMENTS OF THE INVENTION

Example 1

Modification of Chitosan with a Class A Modifier and Sulfonyl Chloride Coupling

This example illustrates the preparation of a Class A type of covalent modification of chitosan with an alkyl sulfonic acid via a sulfonic acid chloride. This synthesis was designed to target a chitosan modification ratio of about 1% (one octane sulfonamide linkage per 100 glucose subunits).

Procedure

In a beaker, 2 grams of chitosan were combined with 40 mL of 10% (v/v) lactic acid. The chitosan was allowed to solubilize overnight. When the chitosan was fully dissolved the sample was placed on a mechanical mixer and stirred at a speed of 80-120 rpm and allowed to mix for 30 minutes. With continued mixing, 100 µL of octanesulfonyl chloride was added dropwise to the chitosan. The sample was allowed to mix for an hour and then 6M NaOH was slowly added until the pH of the sample was between 9 and 10. This pH was maintained with continued mixing for 2 hours. The chitosan was then redissolved by the addition of 100 mL of 10% (v/v) lactic acid. When all of the modified chitosan was dissolved the sample was reprecipitated by the slow addition of 6M NaOH. Mixing was terminated and the sample was divided equally among 4 centrifuge tubes (50 mL) and the samples centrifuged at a sufficient speed and time to sediment out the chitosan. Generally, sedimentation is conducted at about 3850×G. The supernatant was discarded and the modified chitosan placed into dialysis tubing. The chitosan was then dialyzed with 10% (v/v) lactic acid until all of the chitosan was dissolved. The acid dialysate was then removed and replaced with ultrapure water (USP Sterile Water for Injection) and dialyzed for no less than 3 hours. The ultrapure water was then replaced 2 additional times for a total of 3 water washes. A small aliquot of chitosan was removed from the dialysis tubing and a pH measurement was made. The dialysate was then changed to PBS pH 7.4 and the dialysis was monitored until the pH of the chitosan was in the range of 5.7 to 6.0. The chitosan was then dialyzed three times against ultrapure water with each wash lasting no less than 3 hours. The chitosan then went through the freeze-drying, reconstitution and sterilization steps outlined above. The desired final pH of the formulation is 6.2 to 6.4.

Example 2

Modification of Chitosan with a Class C Modifier and Diimide Coupling

This example illustrates the preparation of a class C type of covalent modification of chitosan with N-(2-diethylamino-ethyl)-succinamic acid using diimide coupling.

Procedure

In a beaker, 1.00 g (5.7 mmoles of chitosan monomer units) of chitosan was dissolved in 0.1 N HCl. Then, 0.40 g (1.8 mmoles) of N-(2-diethylamino-ethyl)-succinamic acid was added to the chitosan solution. Next, 0.52 g (2.7 mmoles) of 1-ethylene-3(3-dimethylamino-propyl)carbodiimide hydrochloride (EDC) or N-ethyl-N'-(3-dimethylaminopropyl)carbodiimide hydrochloride and 0.78 g (0.68 mmoles) N-hydroxysuccinimide (NHS) or 1-hydroxy-2,5-pyrrolidinedione was added. The pH of the resulting solution was adjusted to 5 with 1 N NaOH and the mixture was stirred for 24 hours at room temperature. The resulting modified chitosan was purified by precipitation by adjusting the pH to about 9 with 1 N NaOH and collecting the precipitate by centrifugation. Further details of this type of modification reaction can be found in Park, J. H.; Cho, Y. W.; Chung, H.; Kwon, I. C.; Jeong, S. Y. "Synthesis and Characterization of Sugar-Bearing Chitosan Derivatives: Aqueous Solubility and Biodegradability" Biomacromolecules 2003, 4, 1087-1091.

Example 3

Modification of Chitosan with a Class C Modifier and Acid Chloride Coupling

This example illustrates the preparation of a Class C type of covalent modification of chitosan with N-(2-diethylamino-ethyl)-succinamic acid using acid chloride coupling.

Procedure

In a beaker, 0.40 g (1.8 mmoles) of N-(2-diethylaminoethyl)succinamic acid was dissolved in approximately 10 mL of dry THF. Then, 0.26 g (2.2 mmoles) of thionyl chloride was added to the solution and refluxed for one hour with a drying column attached. After refluxing, the solution was cooled to room temperature. 1.00 g (5.7 mmoles of chitosan monomer units) of chitosan was dissolved in a 10% (w/w) acetic acid solution. The N-(2-diethylaminoethyl)succinamic acid chloride solution was then added dropwise with stirring to the chitosan solution. After reacting the chitosan with the succinamic acid chloride, the pH was adjusted to a value between 7 and 8 with 1 N NaOH and the reaction was allowed to continue for 2 to 4 hours. The modified chitosan was purified by raising the pH to 9 by adding 1 N NaOH. The precipitate was then collected by centrifugation.

Example 4

Modification of Chitosan with a Class D Modifier and Acid Chloride Coupling

This example illustrates the preparation of a Class D type of covalent modification of chitosan with cholic acid using acid chloride coupling.

Procedure

One gram of chitosan was dissolved in 20 mL of 10% lactic acid. 0.581 grams of cholic acid (sodium salt) was dissolved in 10 mL of DMSO or ethyl acetate. 120 μL of thionyl chloride was carefully added to the cholic acid solution. The cholic acid-thionyl chloride reaction mixture was refluxed under a drying tube for 1 hour after which the mixture was cooled to room temperature. The cholic acid-thionyl chloride reaction mixture was added to the dissolved chitosan with constant stirring using an overhead mixer. The pH of the reaction solution was adjusted to between 9 and 10 using 6 M NaOH. This reaction mixture was stirred for 2 hours. The precipitated modified chitosan was collected by centrifuging the mixture for 10 minutes at 3850×G. The modified chitosan was redissolved in 50 mL of 10% lactic acid after which it was reprecipitated using 6M NaOH to adjust to pH 9-10. The precipitated modified chitosan was collected by centrifuging the mixture for 10 minutes at 3850×G. The collected modified chitosan was transferred to dialysis tubing and dialyzed against 10% lactic acid until the chitosan was dissolved. After the modified chitosan was dissolved, the dialysate was replaced with deionized (DI) water and dialysis continued for an additional 3 hours. A total of three changes of DI water were employed. After three water washes, the modified chitosan was dialyzed against PBS (pH 7.4) until the pH of the chitosan reached pH 5.7-6.0. Alternatively, PBS dialysis could be replaced by dialysis against other salts such as magnesium sulfate in TRIS buffer. Once the desired pH range had been obtained, two, three hour dialysis steps were completed. The modified chitosan was placed into a freeze dryer flask and frozen at −80° C. for at least 1 hour. The flask was placed on the freeze dryer and dried until completely dry. The dried modified chitosan was stored in a desiccator at −20° C. until needed. The modification steps in the above procedure can be repeated to provide a biomaterial that is more highly modified.

Example 5

Mixture of Chitosan with a Class F Modifier

This example illustrates the preparation of a Class F type of noncovalent modification comprised of a mixture of treated chitosan and perfluoron.

Procedure 1 gram of chitosan was dissolved in 40 mL of 10% acetic acid to produce a solution 25 mg/mL chitosan. 1 mL of perfluoron was added to 1 mL of the 25 mg/mL chitosan solution to yield a final chitosan concentration of 12.5 mg/mL and stirred overnight. Upon initial addition, the solution was biphasic but after prolonged stirring, the perfluoron phase was not evident. The resultant solution displayed an opalescence character. The chitosan/perfluoron mixture was placed into dialysis tubing and dialyzed against water three times and then against PBS overnight.

Example 6

Modification of Chitosan with a Class C Modifier and Diimide Coupling

This example illustrates the preparation of a class C type of covalent modification of chitosan with a polyether using diimide coupling. In this example, a polyether amine was modified with succinic anhydride to produce a succinamic acid linker that facilitates diimide coupling to chitosan.

Procedure

Preparation of the Polyether Amine Acid Linker

In a 250 mL round bottom flask combine 2.49 g (4.2 mmoles) of Jeffamine 600, 150 mL of dry tetrahydrofuran, 0.42 g (4.2 mmoles) succinic anhydride and 1.2 mL (8.4 mmoles) triethylamine. Stir and reflux this mixture for a total of 4 hours. After the solution cools, rotovap until approximately 10 mL of solution remains. Next, dry the sample down further under a nitrogen purge until evaporation of THF is complete and the mixture is a syrupy consistency. This process should yield approximately 1.8 mL of linker.

Modification of Chitosan Using Diimide Coupling

In a beaker, 2.00 g (11.4 mmoles of chitosan monomer units) of chitosan was dissolved in 0.1 N HCl. Then, 1.00 g (1.4 mmoles) of J600-succinamic acid was added to the chitosan solution. Next, 0.287 g (2.5 mmoles) of 1-ethylene-3 (3-dimethylamino-propyl)carbodiimide hydrochloride (EDC) or N-ethyl-N'-(3-dimethylaminopropyl)carbodiimide hydrochloride and 0.478 g (2.5 mmoles) N-hydroxysuccinimide (NHS) or 1-hydroxy-2,5-pyrrolidinedione was added. The pH of the resulting solution was maintained between pH 5-6 with 6 M NaOH and the mixture was stirred (glass or Teflon stirrer) for 72 hours at room temperature. The resulting modified chitosan was purified by precipitation by adjusting the pH to about 9 with 6 M NaOH and collecting the precipitate by centrifugation. The modified chitosan was then transferred to dialysis tubing and dialyzed versus 10% (v/v) lactic acid in PBS for 36 hours until dissolved. The acid dialysate was then removed and replaced with ultrapure water (USP Sterile Water for Injection) and dialyzed for no less than 3 hours. The dialysate was then changed to PBS pH 6.0 and the chitosan was dialyzed for approximately 36 hours. The PBS dialysate was then removed and replaced with ultrapure water (USP Sterile Water for Injection) and dialyzed for no less than 3 hours. The final product was freeze dried and reconstituted according to the normal practices outlined earlier in this document.

Theoretically the aforementioned procedure is expected to yield a 10% modification of the chitosan with the polyether amine. Additional experimentation has shown that it is possible to achieve polyether amine modification levels both higher and lower than 10% by varying the reagent amounts and coupling times. All other processing steps described remain the same. It has been observed that even subtle changes in these modification ratios yield biomaterials with vastly different properties, notably a difference in viscosity and a difference in the ability to hold water.

Demonstration of Unique Physical Characteristics

To characterize the effects of treatments and modification, representative compositions were analyzed by various analytical procedures including circular dichroism (CD), elemental analysis, nuclear magnetic resonance (NMR), gel permeation chromatography (GPC) with light scattering detection, and viscometry. These analytical procedures were performed on treated, as well as modified or modified and treated chitosan. This data was then compared to data on native chitosan samples to document the physical and/or chemical differences between the compositions of the present invention and native chitosan. These initial studies are herein referred to as Study 1. Additional studies, herein referred to as Study 2, were performed at a later date using the same analytical techniques (with the exception of NMR) to study the effects of chitosan molecular weight (MW) as well as type (random (R) vs. block (B)) and degree of deacetylation (DDA). All characterization was performed on the embodiment described in Example 1.

Circular Dichroism (CD)

Figure 3:
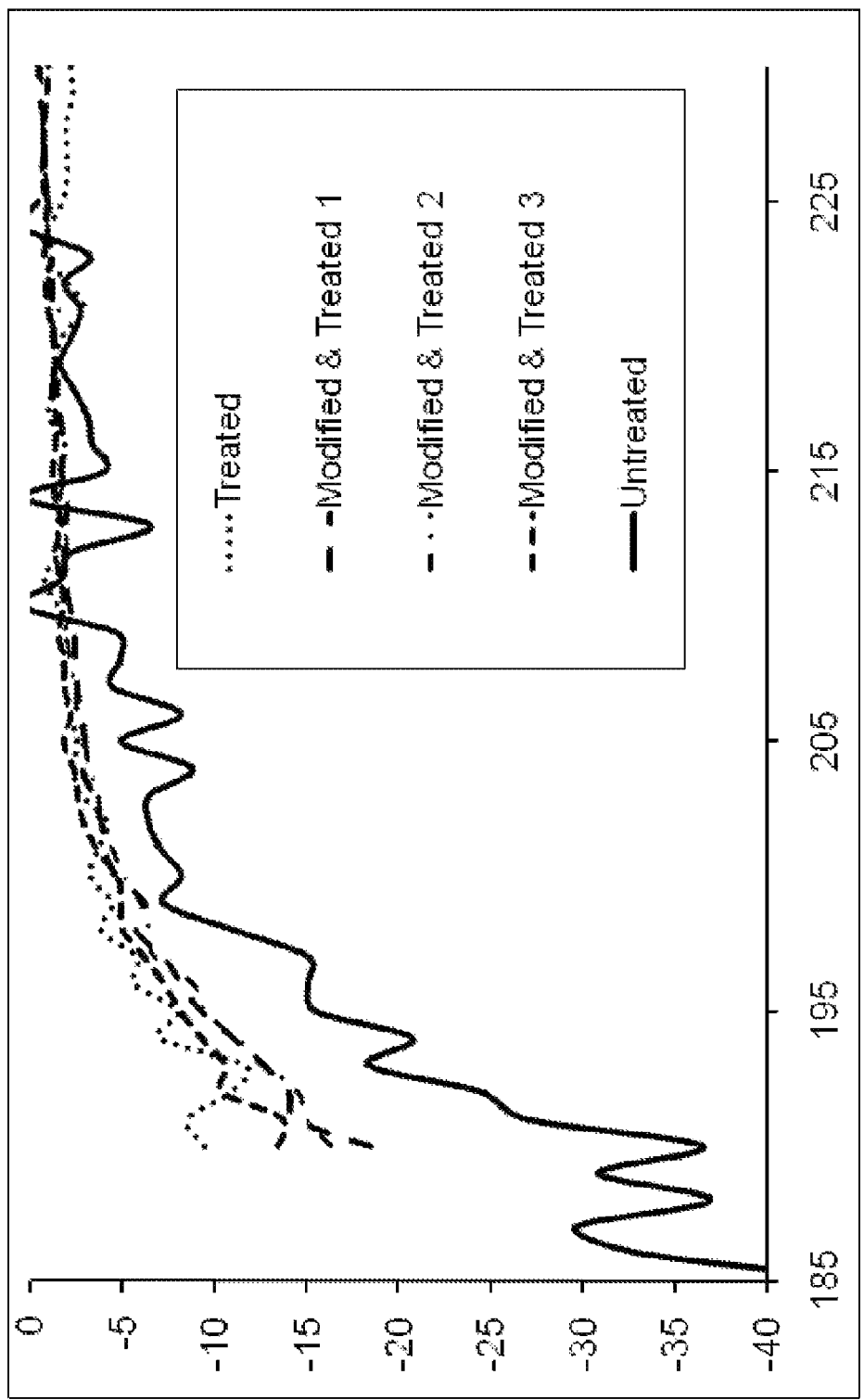
FIG. 3 depicts circular dichroism (CD) spectra collected from treated chitosan, several replicates of the material of Example 1, and untreated chitosan.

Domard (Int. J. Biol. Macromol. 1987, Vol. 9, 98-104) reported the CD spectra of chitosan. The author reports a negative dichroic band at 185 nm that corresponds to the deprotonated (—$NH_2$) form of chitosan, a form which exists as a more crystalline material. The protonated form of chitosan (—$NH_3^+$) does not display the negative band. The electrostatic repulsion of the protonated amines prevents this material from adopting a crystalline conformation. CD spectra collected on our products are shown in FIG. 3. It is clear that the proprietary treatment of chitosan, either modified or unmodified, produces a unique chitosan that is less crystalline in nature than untreated chitosan. These results have been verified with multiple samples on multiple instruments.

Elemental Analysis

Elemental analysis (combustion) was used to determine the degree of modification by octane sulfonate. Sulfur and nitrogen analysis was performed on three modified and treated batches and one unmodified and treated batch of material. Each chitosan subunit contains one nitrogen capable of linking to octane sulfonate using acid chloride coupling. Comparison of total moles nitrogen to the moles of sulfur contributed from the sulfonamide linkage of the octane sulfonate modifier to the chitosan allowed for the determination of the modification ratio for each of the three modified and treated samples. The absence of any sulfur from the unmodified and treated sample confirmed that no sulfur is present in the absence of the modifier. The modification ratio determined for the three modified and treated batches was 1.5±0.3% of the glucose subunits modified. Sulfur levels for the initial studies were close to the limit of detection for the combustion analyzer used for quantitation, therefore, the sulfur analysis for Study 2 was performed using Inductively Coupled Plasma (ICP) which yielded improved sensitivity. Table V summarizes the modification ratios determined in each set of experiments.

TABLE V

Determination of Modification Ratio in the Modified and Treated Chitosan Matrix

| Study | MW Chitosan Raw Material | DDA % | N* | Sulfur Analytical Method | Modification Ratio Average ± SD |
|---|---|---|---|---|---|
| 1 | 261,000 | 98.9 | 3 | Combustion | 1.5 ± 0.3% |
| 2 | 261,000 | 98.9 | 1 | ICP | 0.75% |
| 2 | 274,000 | 85.5R | 3 | ICP | 0.60 ± 0.02% |
| 2 | 364,000 | 81.0B | 3 | ICP | 0.54 ± 0.02% |

*N value represents different batches of modified and treated material.

Modification ratio data for all study groups shows good agreement with the 1% modification ratio targeted during the synthesis process. As noted above, sulfur quantitation by combustion was pushing the quantitative limits of the analytical technique. This is reflected in the increased variability in results for the three batches analyzed. Variability decreased using ICP analysis and it is believed that these values more accurately reflect the modification ratio.

Elemental analysis was further used to determine concentrations of ions contributed by the PBS used to treat and reconstitute the sample. The following elements were quantified: potassium, sodium, chlorine, and phosphorous. These elements represent the following ions in treated chitosan: $K^+$, $Na^+$, $Cl^-$ and $H_2PO_4^-/HPO_4^{2-}$. The concentrations of each ion in the modified and treated chitosan are tabulated below in Table VI and represents the osmotic balance of the chitosan. The multivalent phosphate ion is concentrated relative to the bulk PBS showing the affinity of the positively charged chitosan for that multiply charged anion while sodium is excluded from the bulk material.

TABLE VI

Preferential Incorporation of Anions in the Modified and Treated Chitosan Matrix

| Study | Element | MW Chitosan Raw Material | DDA % | N* | Concentration in Biomaterial (B) (% + SD) | Concentration in PBS Dialysate (D) (%) | Ratio of B:D |
|---|---|---|---|---|---|---|---|
| 1 | P | 261,000 | 98.9 | 2 | 0.89 ± 0 | 0.031 | 28.71 |
| 2 | P | 261,000 | 98.9 | 1 | 0.55 | 0.031 | 17.74 |
| 2 | P | 274,000 | 85.5R | 3 | 0.65 ± 0.14 | 0.031 | 20.97 |
| 2 | P | 364,000 | 81.0B | 3 | 0.62 ± 0.16 | 0.031 | 20.00 |
| 1 | Cl | 261,000 | 98.9 | 2 | 6.66 ± 0.11 | 0.521 | 12.76 |
| 2 | Cl | 261,000 | 98.9 | 1 | 8.64 | 0.521 | 16.58 |
| 2 | Cl | 274,000 | 85.5R | 3 | 6.20 ± 0.61 | 0.521 | 11.90 |
| 2 | Cl | 364,000 | 81.0B | 3 | 5.90 ± 0.75 | 0.521 | 11.32 |
| 2 | Na | 261,000 | 98.9 | 1 | 0.0063 | 0.371 | 0.017 |
| 2 | Na | 274,000 | 85.5R | 3 | 0.0086 ± 0.003 | 0.371 | 0.023 |
| 2 | Na | 364,000 | 81.0B | 3 | 0.013 ± 0.0006 | 0.371 | 0.035 |

*N value represents different batches of modified and treated material.

R = Random deacetylation;

B = Block deacetylation

Nuclear Magnetic Resonance (NMR)

Proton NMR was capable of detecting a resonance resulting from the hydrocarbon modification of chitosan. This resonance peak was present in the three modified and treated batches analyzed and not in the unmodified and treated batch verifying the origin of the peak being the modifier. Comparison of peak integrations for this particular resonance to a well defined resonance attributable to the chitosan backbone (C2) gave a modification ratio of approximately 0.5%. This value shows good agreement with the modification ratios predicted by the ICP elemental sulfur analysis and shown in Table V.

Gel Permeation Chromatography (GPC)

Figure 4:
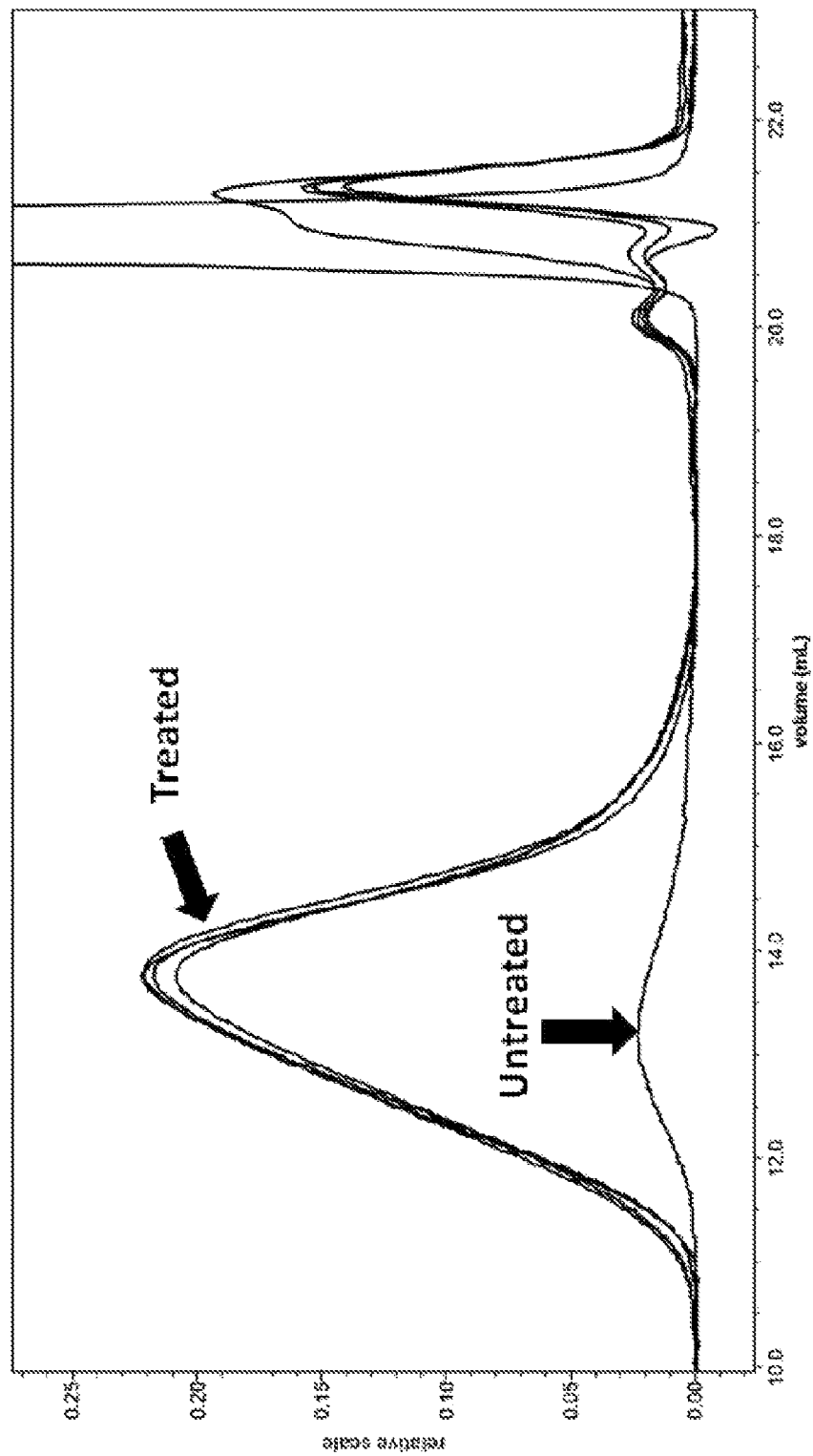
FIG. 4 depicts GPC chromatograms collected from treated chitosan, several replicates of the materials of Example 1, and untreated chitosan.

Thirteen chitosan samples were analyzed using GPC with light scattering detection under the following standardized conditions. An Ultrahydrogels (Two Linear) column with 0.3M acetic acid/0.3M sodium acetate as the mobile phase at 30° C. with a flow rate of 1.0 mL/minute. An injection volume of 150 µL was used and the elution profile was determined using a Viscotek Y-501 detector and a DAWN light scattering detector. A summary of the data is shown in Table VII and chromatograms are shown in FIG. 4. Comparison of the Weight Average Molecular Weight ($M_w$) data shows a distinct difference between all chitosan samples having undergone the treatment of Example 1. The untreated materials displayed a lower retention volume (higher $M_w$) than the materials receiving the treatment of this invention. Similar changes in $M_w$ were seen for all chitosan samples prepared according to Example 1 studied. In these experiments, the modification is that of Example 1. Samples were run at two different testing labs to confirm these results. This change in Mw is independent of chitosan properties such as molecular weight (MW), degree of deacetylation (DDA) and the type of deacetylation (block versus random). Upon treatment, samples GPC-2, 3, 4, and 5 show an observable and reproducible shift in $M_w$, from 263,000 to 219,000, a reduction to 84%. This change in observed molecular weight is inconsistent with simplistic chain cleavage as such chain cleavage would not be expected under these experimental conditions. An alternative explanation could be a change in the molecular conformation. The multivalent phosphate ion could attract disparate parts of the chitosan backbone, forming a more compact structure. Elongated (ellipsoid) particles typically elute more quickly on GPC columns, therefore a higher retention volume would indicate an apparent molecular contraction. This is consistent with our materials having access to a greater included volume.

This alternative explanation is further supported by the data obtained after reversing the proprietary treatment, thus eliminating the unique conformational structure. One of the modified and treated samples was processed to remove the phosphate and replace it with monovalent chloride anions, which would not be expected to facilitate a molecular contraction. GPC analysis was then performed on this sample. The data for the "reversed treatment" clearly show that there is an observable shift in average molecular weight, $M_w$, from 219,000 to about 253,000, thus verifying that the change in measured $M_w$ is reversible. The conformationally altered chitosan compositions resulting from the treatments of this invention yield a biocompatible adhesive system that is unexpectedly superior to untreated chitosan based adhesives and superior to many competing adhesive systems.

This behavior is also seen when using chitosans with differing molecular weights, degree of deacetylation or type of deacetylation (block versus random), samples GPC-8 through GPC-13.

TABLE VII

GPC Data

| Sample | Material | Raw Material MW | % DDA | $M_w$ by GPC | $M_w$/MW |
|---|---|---|---|---|---|
| GPC-1 | Unmodified/Untreated | 261,000 | 98.9 | 263,000 | 1.01 |
| GPC-2 | Unmodified/Treated | 261,000 | 98.9 | 220,800 | 0.85 |
| GPC-3 | Modified/Treated Batch A | 261,000 | 98.9 | 219,000 | 0.84 |
| GPC-4 | Modified/Treated Batch B | 261,000 | 98.9 | 219,500 | 0.84 |
| GPC-5 | Modified/Treated Batch C | 261,000 | 98.9 | 216,200 | 0.83 |
| GPC-6 | Treatment Reversed Batch B | 261,000 | 98.9 | 252,600 | 0.97 |
| GPC-7 | Modified/Treated | 261,000 | 98.9 | 220,000* | 0.84 |
| GPC-8 | Modified/Treated | 274,000 | 85.5R | 222,700* | 0.81 |
| GPC-9 | Modified/Treated | 274,000 | 85.5R | 227,500* | 0.83 |
| GPC-10 | Modified/Treated | 274,000 | 85.5R | 222,300* | 0.81 |
| GPC-11 | Modified/Treated | 364,000 | 81.0B | 226,200* | 0.62 |
| GPC-12 | Modified/Treated | 364,000 | 81.0B | 260,700* | 0.72 |
| GPC-13 | Modified/Treated | 364,000 | 81.0B | 223,100* | 0.61 |

*Second testing lab
R = Random deacetylation;
B = Block deacetylation
Table VII shows that the treated chitosans evidence a ratio of $M_w$ to MW that is less than one. The $M_w$ to MW ratio is generally between about 0.50 and about 0.90. In certain embodiments, the $M_w$ to MW ratio is between about 0.50 and about 0.85. In other embodiments, the $M_w$ to MW ratio is between about 0.60 and about 0.85.

Viscometry

Relative viscosity measurements were made for a representative sampling of all materials presented in Table VII using a Brookfield Viscometer. All samples were at identical concentrations (10 mg/mL). A summary of the data is presented in Table VIII. Chitosan receiving the invention's proprietary treatment, whether modified or unmodified, again demonstrated unique and reproducible physical properties in comparison with unprocessed formulations. When making this type of measurement using the same starting material (same MW), sample pH and concentration, one would expect to see relative viscosity measurements of similar proportion. Rather, the viscosity was consistently and reproducibly reduced by the proprietary treatment, by approximately 50%. This is consistent with the attraction between the phosphate ions and the chitosan producing a tighter molecular conformation. The modification studied in these examples was that of Example 1.

TABLE VIII

Viscosity Data For Various Chitosan Formulations

| Sample | Material | Raw Material MW | % DDA | Concentration (mg/mL) | Relative Viscosity (cP) | Shear Rate (1/sec) | T ° C. |
|---|---|---|---|---|---|---|---|
| V-1 | Unmodified/Untreated | 261,000 | 98.9 | 10 | 91.7 | 39.6 | 30 |
| V-2 | Unmodified/Treated | 261,000 | 98.9 | 10 | 38.9 | 39.6 | 30 |
| V-3 | Modified/Treated Batch A | 261,000 | 98.9 | 10 | 41.8 | 39.6 | 30 |
| V-4 | Modified/Treated Batch B | 261,000 | 98.9 | 10 | 43.3 | 39.6 | 30 |
| V-5 | Modified/Treated Batch C | 261,000 | 98.9 | 10 | 40.5 | 39.6 | 30 |

TABLE VIII-continued

Viscosity Data For Various Chitosan Formulations

| Sample | Material | Raw Material MW | % DDA | Concentration (mg/mL) | Relative Viscosity (cP) | Shear Rate (1/sec) | T °C. |
|---|---|---|---|---|---|---|---|
| V-6 | Modified/Treated | 261,000 | 98.9 | 10 | 35.1 | 26.4 | 25 |
| V-7 | Modified/Treated | 274,000 | 85.5[R] | 10 | 50.2 | 26.4 | 25 |
| V-8 | Modified/Treated | 364,000 | 81.0[B] | 10 | 118.6 | 26.4 | 25 |

[R] = Random deacetylation and
[B] = Block deacetylation

As would be expected, an increase in molecular weight of the material corresponds to an increase in the relative viscosity of the material, samples V-7 and V-8 have higher molecular weight and display correspondingly higher viscosities.

Figure 5A:
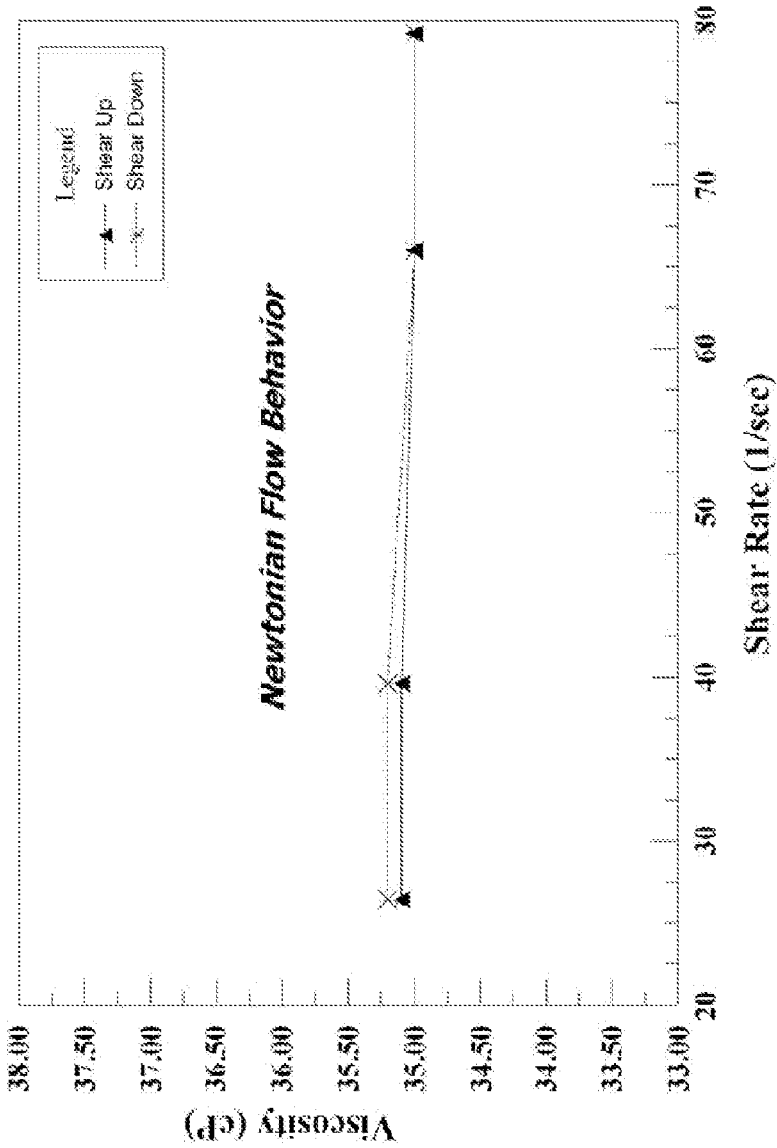
FIGS. 5A-E depict the variety of viscosity behaviors exhibited by the material of Example 1 differing in such characteristics as molecular weight and degree of deacetylation.
Figure 5B:
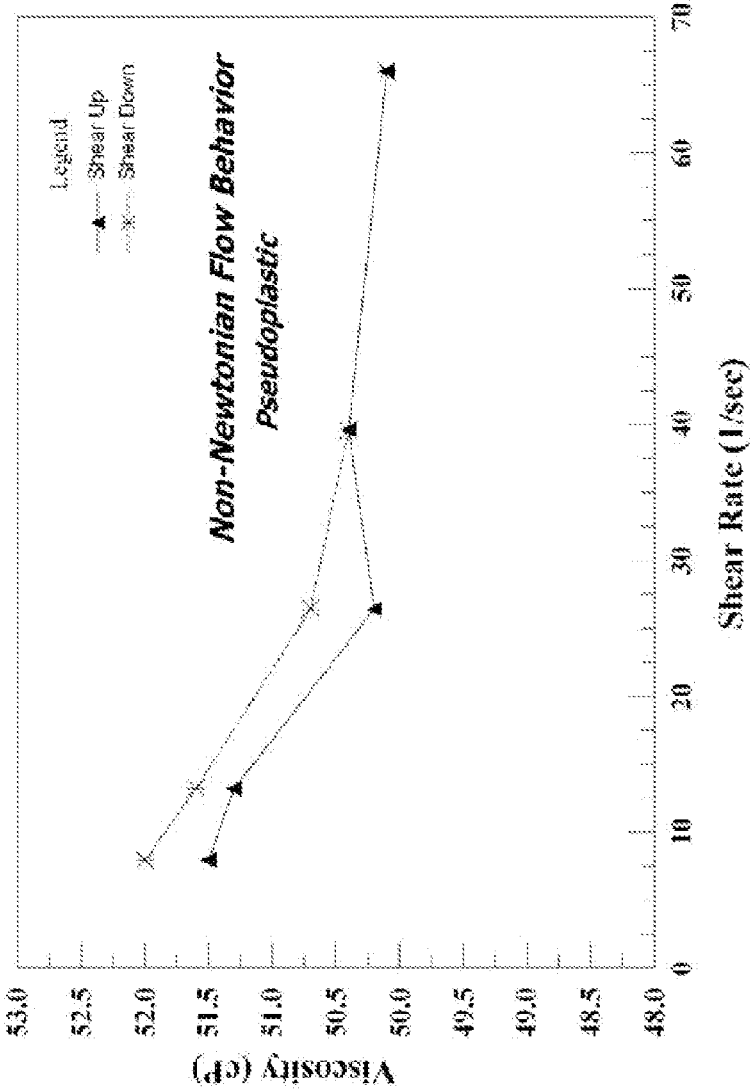
Figure 5C:
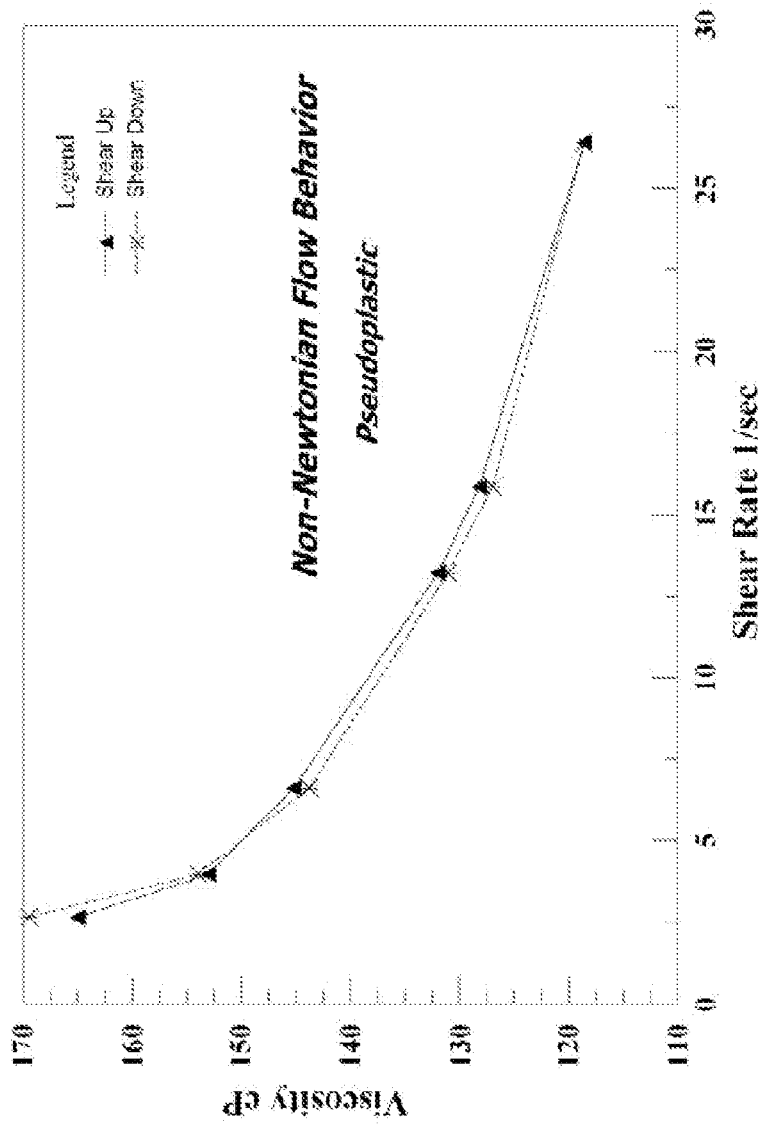

More extensive viscometry testing was performed on samples V-6, V-7 and V-8. Sample V-6 (FIG. 5A) displayed Newtonian Flow behavior while samples V-7 (FIG. 5B) and V-8 (FIG. 5C) show progressively greater deviations from Newtonian behavior showing pseudoplastic behavior as the molecular weight increases.

Figure 5D:
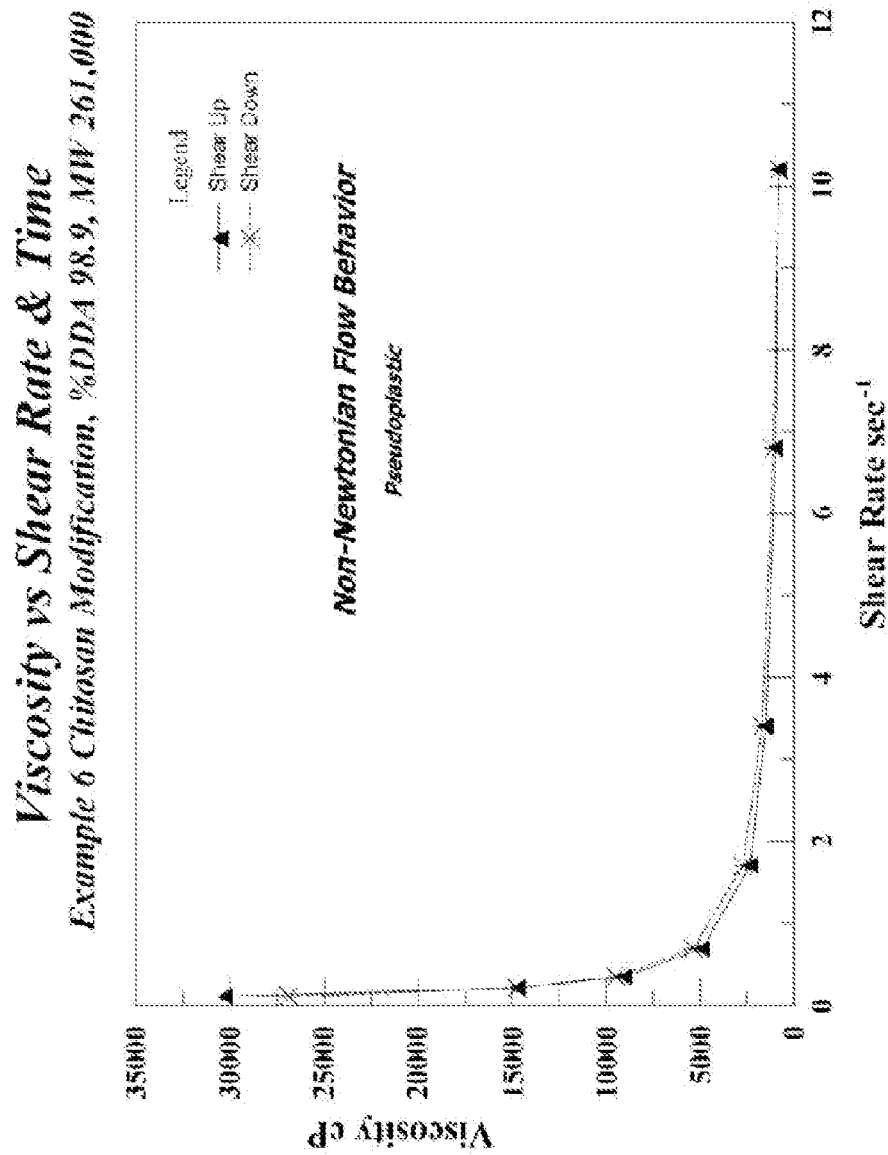
Figure 5E:
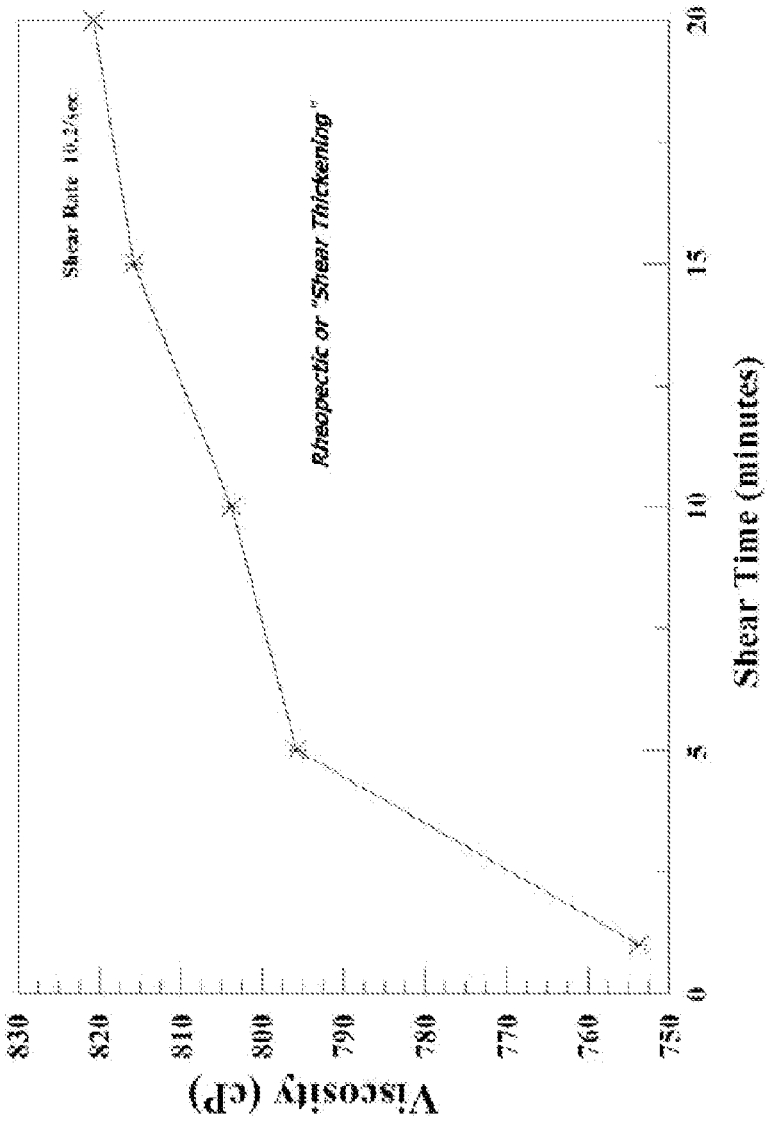

However, other modifications result in dramatically different viscosity behavior. The material of Example 6 was studied to understand its unique properties that make it useful as a dermal filler. The material of Example 6 is unique in that its capacity to contain water over a wide range of pH is greatly enhanced over all other forms of chitosan studied. This behavior has been attributed to the nature of the covalent chemical modification. In addition, the material of Example 6 displays dramatically different viscosity behavior. For example, the modification used in Example 6 results in a very viscous material that displays non-Newtonian (pseudoplastic) behavior (FIG. 5D) and rheopectic behavior (FIG. 5E). Rheopectic behavior was not observed with the material of Example 1.

It is clear that the judicious choice of the modifying agent will allow the tailoring of the water retention, viscosity profile, and other beneficial properties to fit the intended use of the material.

Demonstration of Applications and Application Properties

Example 7

Ex Vivo Tensile Bond Strength Testing

This example was designed to assess the ability of the various formulations of this invention to bond tissues ex vivo.

Procedure

A variety of tissues were obtained from a number of sources. The target tissue was then cut into small strips, approximating 4×8 mm. The test material was applied to the end of one tissue strip. Another tissue strip was then apposed to the treated strip to form an approximately 4×4 square millimeter of overlap in an area of overlap with single-thickness "tails" projecting from each end. The tissue preparation was then wrapped in a thin plastic sheet, sandwiched between glass microscope slides, and compressed with mild compression (~125 g). After bonding, the tissues were carefully placed in PBS for at least an hour, but no longer than 24 hours, prior to tensile strength testing to ensure any residual "stickiness" resulting from partial dehydration would not influence the measured tensile strengths. Testing of tensile bond strengths was conducted using a tensiometer, whereby the force was gradually increased to the point of bond failure. Peak loads were noted and bond strengths were calculated as g-f/cm$^2$.

Results

Table IX provides comparison data for a number of competing technologies and controls. Table X provides representative bond strengths for each of several general classes of modified chitosan materials. The most promising formulations were then subjected to additional safety and efficacy testing, data provided in subsequent examples.

Conclusion

This model provides a useful tool to screen potential formulations and to compare the relative adhesive properties of different formulations in different tissues. Using this model, it was determined that the formulations of this invention offer excellent adhesive properties, which have proven to be superior to competing technologies or to the bioadhesive nature of native chitosan alone.

TABLE IX

Comparison Data

| Treatment | Shear Strength (g-f/cm$^2$) | System |
|---|---|---|
| Saline[1] | 13 ± 4 | Skin-to-skin |
| Hemaseel Fibrin Glue[2] | 82 ± 45 | Veritas ™-to-artery |
| BioGlue[2] | 232 ± 188 | Veritas ™-to-artery |
| Tisseel Fibrin Glue[1] | 261 ± 51 | Skin-to-skin |
| Ethyl cyanoacrylate[1] | 385 ± 119 | Skin-to-skin |
| Untreated chitosan[2] | 230 ± 92 | Cornea-to-cornea |

[1]U.S. Pat. No. 5,817,303 assigned to Protein Polymer Technologies, skin-to-skin values
[2]PhotoBioMed data
Veritas ™ is a prepared pericardial product manufactured by Synovis Life Sciences

TABLE X

Representative Tensile Bond Strength Data for Various Modification Classes As Defined in TABLE II

| Modified Chitosan | Modification Class | Shear Strength g-f/cm$^2$ | Bonding System |
|---|---|---|---|
| Octane | A | 837 ± 324 | Cornea-Cornea |
| Protoporphyrin | B | 368 ± 125 | Duraguard-Artery |
| N-(2-Diethylamino-ethyl)-succinamic acid | C | 717 ± 230 | Cornea-Cornea |
| Deoxycholic acid | D | 609 ± 157 | Duraguard-Artery |
| Perfluoron | F | 267 ± 99 | Veritas-Artery |
| Unmodified/Treated | G | 1164 ± 546 | Cornea-Cornea |

Duraguard ™ is a prepared pericardial product manufactured by Synovis Life Sciences
Veritas ™ is a prepared pericardial product manufactured by Synovis Life Sciences
Corneas and arteries were obtained post mortem from a slaughter house

Example 8

Demonstration of Tissue Bonding In Vivo

This example was designed to assess the ability of a composition of this invention to bond tissues in vivo, specifically to seal a corneal incision in a rabbit model, and utilized the material of Example 1.

Procedure

New Zealand White rabbits with a body weight of 7 to 8 lbs were used. The rabbits were anesthetized with intramuscular xylazine (5 mg/kg) and ketamine (35 mg/kg). A local anesthetic of proparacaine hydrochloride solution 0.5% (Alcaine, Alcon) was applied to the rabbit eyes. The eyes were taped open with Transpore Tape (3M) and covered with Steri-Drape (3M) to provide a sterile surgical field. Corneal incisions were created with a 3.2 mm Clear Cut slit knife (Alcon). The slit knife was marked with a sterile surgical marker (Viscot) so the incision would be defined. A non self-sealing, 3.2-mm incision was made in each cornea, approximately 1 mm anterior to the limbus, angled 45° from the plane of the iris and penetrating the full thickness of the cornea. To ensure the incision was leaking, sterile Balanced Salt Solution (BSS) (Alcon) was injected into the anterior chamber with a 23-gauge needle (Techcon). In the experimental groups, approximately 10 to 20 µL of the material of Example 1 was dispensed into the corneal incision with a 30-gauge blunt needle (Techcon) and gentle pressure was applied with a surgical eye spear (Murocel) to ensure the tissues were opposed and to dry the incision surface. Approximately 5 to 10 µL of the material of Example 1 were applied topically and allowed to set for a five minute bonding period. In the control groups, the incision was sealed with 10-0 non-absorbable nylon black monofilament surgical suture (Alcon) by placing a suture from the sclera into the cornea. After treatment all eyes were irrigated with BSS, treated with antibiotic moxifloxacin hydrochloride 0.5% (Vigamox, Alcon), and taped close to prevent the eye from drying. Post-operatively the rabbits were given a steroid antibiotic of tobramycin and dexamethasone (Tobradex, Alcon) and ketorolac tromethamine 0.5% (Acular, Allergan) four times a day until harvested. Animals were monitored to evaluate for potential leaks and any sign of irritation. Animals were harvested at three time points (n=6 per time point), 1-2 hours, 1 day, and 7 days. Immediately following euthanasia, BSS was injected into the anterior chamber using a 23-gauge needle (Techcon) to pressurize the chamber. A physiograph was used to assess the leak/burst pressure for each eye. Anterior chamber pressures are typically 12-20 mmHg. Eyes were considered successfully sealed if the leak/burst pressure exceeded 50 mmHg.

Results

Six rabbits were observed and harvested at 1-2 hrs. No irritation was seen in any of the control (sutured) or experimental (treated with the material of Example 1) eyes. All eyes held pressure in excess of 50 mmHg. Six rabbits were observed and harvested on day 1. No irritation was seen in the experimental eyes. A slight irritation was noted in the sutured eyes. All eyes held pressure in excess of 50 mmHg. Six rabbits were observed and harvested on day 7. No irritation was seen in any of the control or experimental eyes. All eyes held pressure in excess of 50 mmHg.

Conclusion

The material of Example 1 was found to be a successful sealant of corneal incisions in the rabbit eye. This material demonstrated excellent biocompatibility, standard suture treatment elicited an inflammatory response while the composition of this invention did not.

Example 9

Cytotoxicity Assays

This example was designed to assess the cytotoxicity of the formulations of this invention on corneal endothelial cells in culture and utilized the material of Example 1.

Procedure

Rabbit corneal endothelial cells were grown in standard tissue culture medium (Dulbecco's Modified Eagle Medium—DMEM) containing 10% fetal calf serum (FCS) until they become confluent (about 7-10 days). Cells were grown in 12-well tissue culture plates. Confluent cultures were used to test the toxicity of the adhesive formulation of this invention on these cells. The stock compound (10 mg/mL) was diluted in DMEM containing 0.2% FCS to obtain 1, 2, or 3 mg/mL final concentration just before use. The cells were incubated in the presence of different concentrations of adhesive (as above) in a total volume of 0.5 mL DMEM+0.2% FCS/well at 37° C. for 24 hours. At the end of experiment, cells were washed with PBS and analyzed for the presence of live and dead cells under each experimental condition using Molecular Probes™ Live/Dead® Viability/Cytotoxicity kit for mammalian cells as per the manufacturer's specifications. Cell culture experiments were run in triplicate. These procedures were performed using primary cells and repeated using secondary cell lines.

Figure 6:
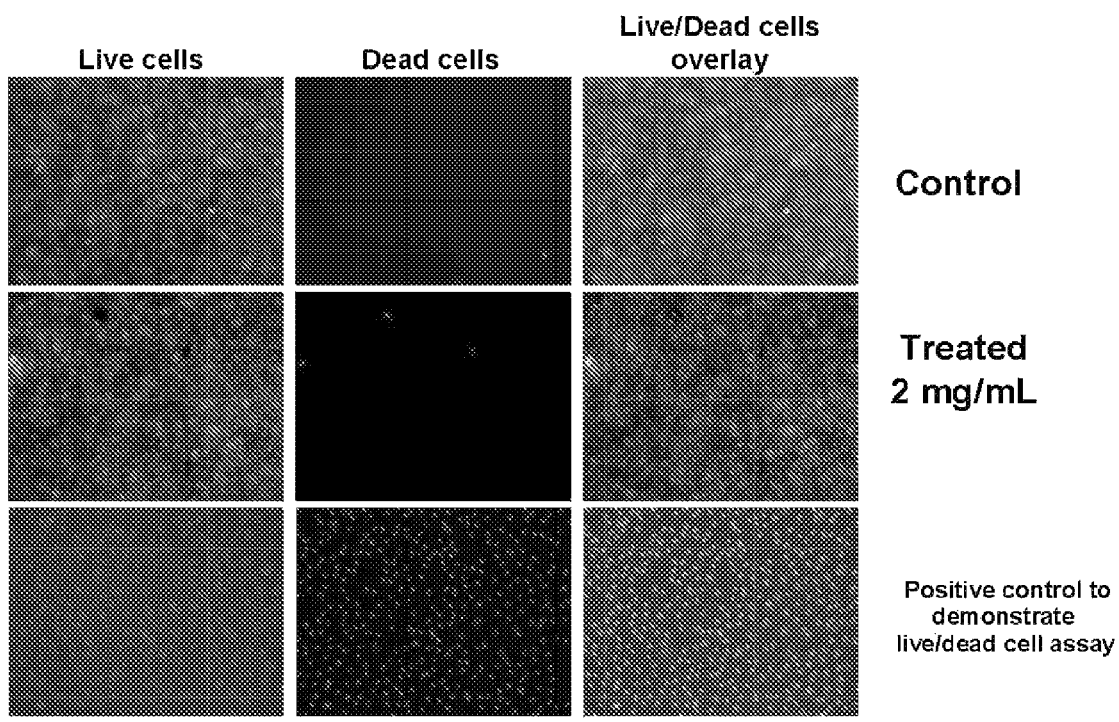
FIG. 6 illustrates the safety of the materials of this invention to living cells. Death of corneal endothelial cells was not observed when primary cultures were exposed to the material of Example 1 for 20-24 hours (middle panels). Death was induced in cells by fungal infection and detectable using this staining technique (bottom panel).

Referring now to FIG. 6, data is shown that indicates that the corneal incision sealing agent of this invention is not toxic. Death of corneal endothelial cells was not observed when primary cultures were exposed to compound for 20-24 hours (top and middle panels). Death was induced in cells by fungal infection (bottom panel).

Figure 7:
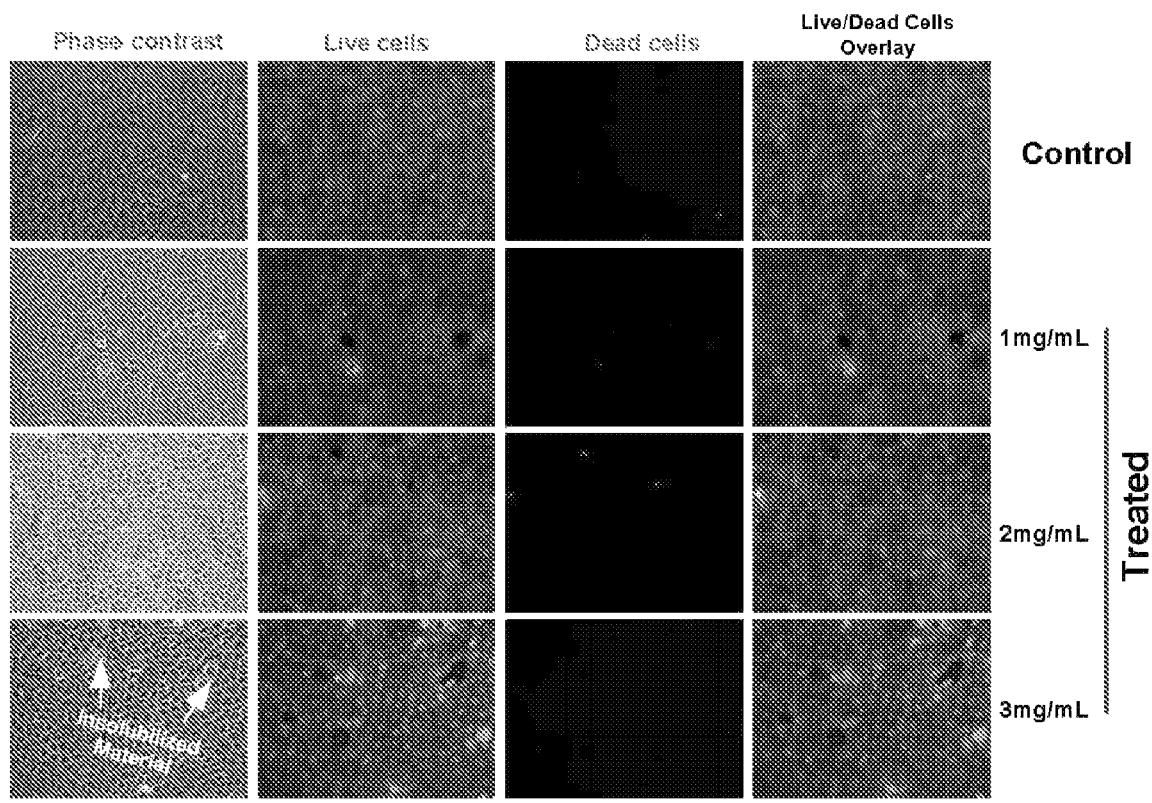
FIG. 7 depicts a series of corneal endothelial cell culture toxicity studies with varying doses of the material of Example 1; no cytotoxicity was observed.

Referring now to FIG. 7, a series of toxicity studies with compounds of this invention are shown.

Results

There was no cytotoxicity observed in these cultured cells under any of the test conditions.

Conclusion

The adhesive compound of this example is not toxic to corneal endothelial cells. Even at 3 mg/mL, where essentially one third of the media consisted of an adhesive of this invention, no cytotoxic effects were observed.

Example 10

Corneal Pocket Model

This example illustrates the biocompatibility of a formulation of this invention when placed within the corneal stroma of a rabbit eye utilizing the material of Example 1.

Procedure

New Zealand White rabbits with a body weight of 7 to 8 kg were used. The rabbits were anesthetized with intramuscular xylazine (5 mg/kg) and ketamine (35 mg/kg). A local anesthetic of proparacaine hydrochloride solution 0.5% (Alcaine, Alcon) was applied to the rabbit eyes. The eyes were taped open with Transpore Tape (3M) to prevent contamination from the eyelashes. The initial corneal incision was created with a 300 micron precision depth knife (Sharpoint). Approximately a 2.5-mm incision was made in each cornea, approximately 1.5 mm anterior to the limbus. A 3.5-mm diameter lamellar stromal pocket was created at 300 microns into the cornea using a Bevel Up Angled Crescent Knife (Sharpoint). In the experimental groups, approximately 20 µL of the adhesive formulation (10 mg/mL) was dispensed into the corneal pocket with a 23-gauge blunt needle (Techcon) and the pocket was stroked with gentle pressure using surgical eye spear (Murocel) to ensure no air remained in the pocket. The adhesive was allowed to set for the five minute bonding period. In the control groups, approximately 20 μL of BSS was dispensed into the corneal pocket following the same procedure as the experimental groups. After treatment all eyes were irrigated with BSS, treated with antibiotic moxifloxacin hydrochloride 0.5% (Vigamox, Alcon), and taped closed to prevent the eye from drying during recovery from anesthesia. Post-operatively the rabbits were given a steroid antibiotic of tobramycin and dexamethasone (Tobradex, Alcon) four times a day for seven days.

Results

Three rabbits were observed and harvested on each of days 1, 14, 30, 60, and 90. Two rabbits were observed and harvested at 120 days. Macroscopic observations revealed no irritation in any of the test specimens. Histological observations confirmed that the material remained substantially benign in numerous studies. Residual chitosan remained evident in the stromal pocket out to 120 days.

Figure 8:
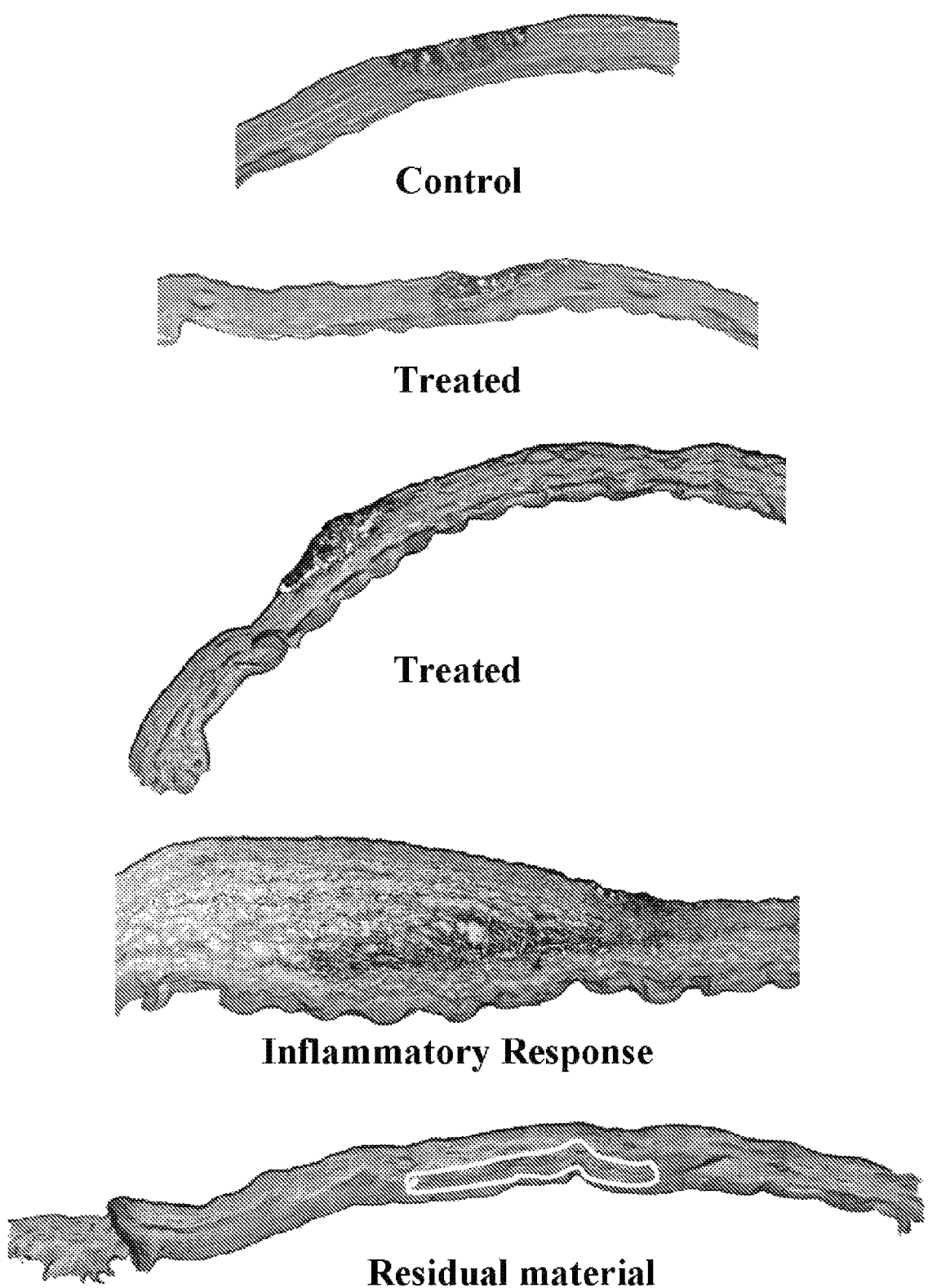
FIG. 8 illustrates the safety of the materials of this invention within the stroma of the cornea. The material of Example 1 elicits virtually no immunogenic or inflammatory response, even upon chronic administration. Residual material can be observed, even at 60 days, without any adverse effects to the cornea—in vivo study.

Referring now to FIG. 8, this figure illustrates the safety of these materials within the stroma of the cornea. These materials elicit virtually no immunogenic or inflammatory response, even upon chronic administration. Residual material can be observed, even at 120 days, without any adverse effects to the cornea. The apparent lesion observed in these specimens is due to the mechanical damage inflicted during creation of the corneal pocket. The pocket actually extends beyond the lesioned area for a length of approximately 3.5 mm at a depth of approximately 300 μm within the stroma. Test materials are instilled within this pocket and have either been inert (top three specimens) or caused a severe inflammatory response (fourth specimen positive control).

Conclusion

This compound did not induce an inflammatory or immune response in the corneal stroma of the rabbit eye. Prior results with inflammatory agents induced significant irritation, photophobia, inflammation, corneal edema, and neovascularization.

Example 11

Intradermal Injections: Biocompatibility and Longevity of Base Material

This example was designed to determine the biocompatibility of a formulation of this invention when injected intradermally and utilized the material of Example 1.

Procedure

Sprague Dawley rats were anesthetized with an intramuscular injection of xylazine (7 mg/kg), ketamine (70 mg/kg), and buprenorphine (0.05 mg/kg). The dorsal skin surface of the rat was shaved and cleaned with alcohol. 0.2 mL of the materials of Example 1 was subcutaneously injected into an identified grid section. Additionally, 0.2 mL of both a positive and negative control material were subcutaneously injected. The injection sites were marked with a small tattoo dot to assure harvest of the appropriate regions at the time of euthanasia, occurring at either 7 or 28 days. At the appropriate time point, animals were euthanized, skin samples with associated muscle were harvested, and specimens were embedded in OCT and frozen for subsequent cryosectioning and histological evaluation.

Results

The negative control specimen was completely resorbed by day 7 and there was virtually no immune response at the site of injection at either time point. The positive control showed significant reduction, via resorption or biodegradation, by day 7 and virtual absence by day 28. However, a significant inflammatory response was observed at the injection site of the positive control, even at day 28 when the material was no longer evident. The materials of Example 1 remained present out to day 28 and showed a lesser inflammatory response at both the 7 and 28 day time points than the positive control. A very minimal and localized immune response was observed while subadjacent tissue exhibited typical morphology.

Conclusions

The materials of Example 1 of this invention show good biocompatibility and excellent longevity in the tissues tested. These materials could be potentially useful as dermal fillers or as a depot for sustained drug delivery.

Example 12

Periocular Injections: Biocompatibility and Longevity of Filler/Bulking Material This example was designed to determine the biocompatibility and retention of a material of this invention, specifically designed to serve as a filler or bulking agent, and utilized the material of Example 6.

Procedure

New Zealand White rabbits were used for this study (n=3). The treatments of the eyes were randomized. In each animal, one eye was treated with 60-80 μL of the material of Example 6 at 10 mg/mL and the other eye was treated with 60-80 μL of the material of Example 6 at 20 mg/mL. The rabbits were anesthetized using isoflurane at 2.0 to 3.5% in a 40%/60% oxygen/air mixture. Two drops of a topical anesthetic (Tetracaine—0.5% drops or Alcaine) were applied to the rabbit eyes. A forceps was used to gently lift the conjunctiva from the surface of the globe resulting in a "tenting" of the conjunctiva. The injection was made well off the surface of the globe. (This maneuver greatly reduces the risk of globe perforation.) With the needle placed tangential to the globe, the needle tip was inserted into the tent, and the appropriate formulation was delivered. A 23-gauge needle was used to make the injections. 100 μL of the material of Example 6 at 10 mg/mL was injected into the conjunctiva of one eye. 100 μL of the material of Example 6 at 20 mg/mL was injected into the conjunctiva of the contralateral eye. Following the injections, antibiotic drops (Vigamox®) were placed into the eyes. Daily observations were made for one week, then once a week until the study was concluded. Pictures were taken of the conjunctiva at 24 hours. At 29 days, the rabbits were euthanized and conjunctivas were harvested and processed for histology.

Results

When looking at the rabbits before lowering the eyelid, all the rabbit eyes maintained a bright, moist appearance at all observation points. Within the first 24-48 hours, there was a slight reduction in apparent volume but all injection sites maintained considerable distention of the conjunctival tissue. These formulations are designed to optimize the retention of water so that they retain a volume-occupying nature in order to serve as a filler or bulking agent. Slight redness was noted in the conjunctiva for the first couple of days. This very likely may have been attributable to the overdistention of the tissue. At 29 days, all the eyes looked good. There continued to be a residual distention of the conjunctival tissue (comparable to that observed after 48 hours). Histological assessment, utilizing calcofluor staining, confirmed the presence of the material of Example 6 in the conjunctiva of treated eyes 29 days post-injection.

Conclusion

The material of Example 6 shows promise as a filler or bulking agent. Following periocular injection, the material of Example 6 remained present in the conjunctival space for at least 29 days, with excellent biocompatibility. While not quantified in this study, these materials demonstrated desirable qualities as they retained a significant percentage of their initial volume.

Example 13

In Vitro Corneal Retention Model

This example was designed to determine the kinetics of formulation retention on the corneal surface of an in vitro rabbit eye model and utilized the material of Example 1. This example was designed to assess the ability of a modified and treated chitosan material to act as a drug delivery matrix through, ultimately, mixture of free drug within the prepared chitosan material and subsequent adherence to the target tissue substrate with elution of the drug into the tissue via diffusion.

Procedure

Viable, excised rabbit eyes were obtained from a commercial source. The formulations of this invention were conjugated with fluorescein isothiocyanate (FITC) and prepared at 20 mg/mL concentration. Globes were rinsed in PBS, then were drained and allowed to stand at room temp for 1 min. The epithelial surface of the cornea was gently dabbed with a kimwipe to remove excess PBS. The epithelium was treated with 200 µL of this formulation to ensure thorough coverage. After 1 min, the globes were transferred to a container with PBS and rinsed for 1 min. Corneal buttons were dissected and transferred to the DMEM/F12 organ culture media and rinsed again. Globes were then incubated in a well (12 well tissue culture plate) containing 4 mL DMEM/F12 at 37° C. with gentle agitation for different time periods (0, 4, 8, 16, 24 hours; n=5). Care was taken to use constant rinse volumes and agitation rates. At the desired time point, corneas were removed and rinsed in fresh PBS for 1 min with gentle agitation. Corneas were embedded in OCT and snap frozen in liquid nitrogen. Duplicate sections were obtained from each of four levels of the embedded cornea. These sections were analyzed for this formulation retention using fluorescent microscopy. Image analysis software was utilized to quantify corneal fluorescence using a systematic approach that averaged multiple sites from multiple sections in an unbiased fashion. Control corneas (untreated) were used to quantify native autofluorescence, which was then subtracted from the total fluorescence measurements. Remaining fluorescence could be attributed to residual FITC-labeled formulation.

Results

Figure 9:
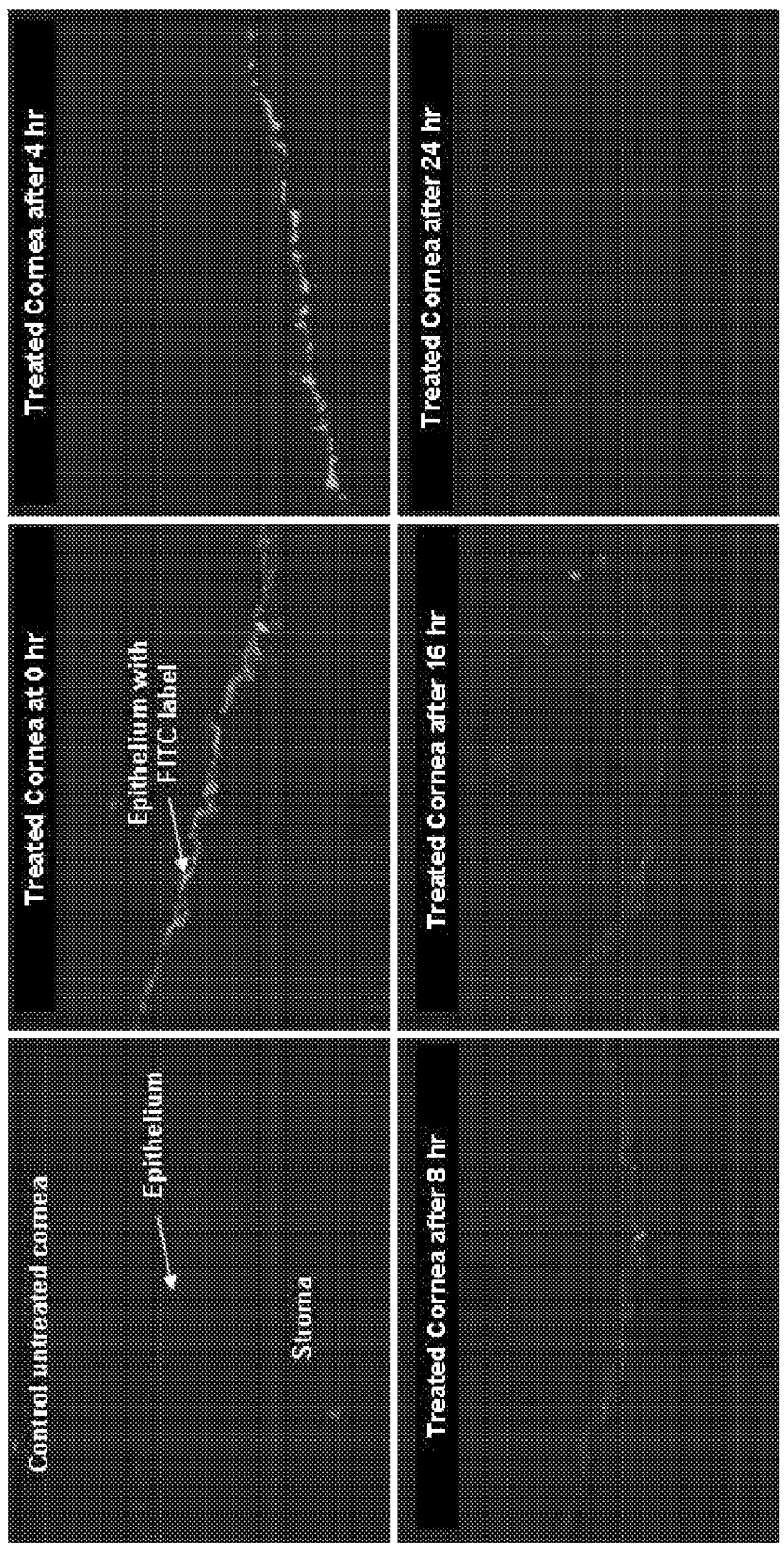
FIG. 9 depicts the retention of the material of Example 1 on the cornea of the rabbit, with significant residual even at 8 and 16 hours after application—in vitro study.
Figure 10:
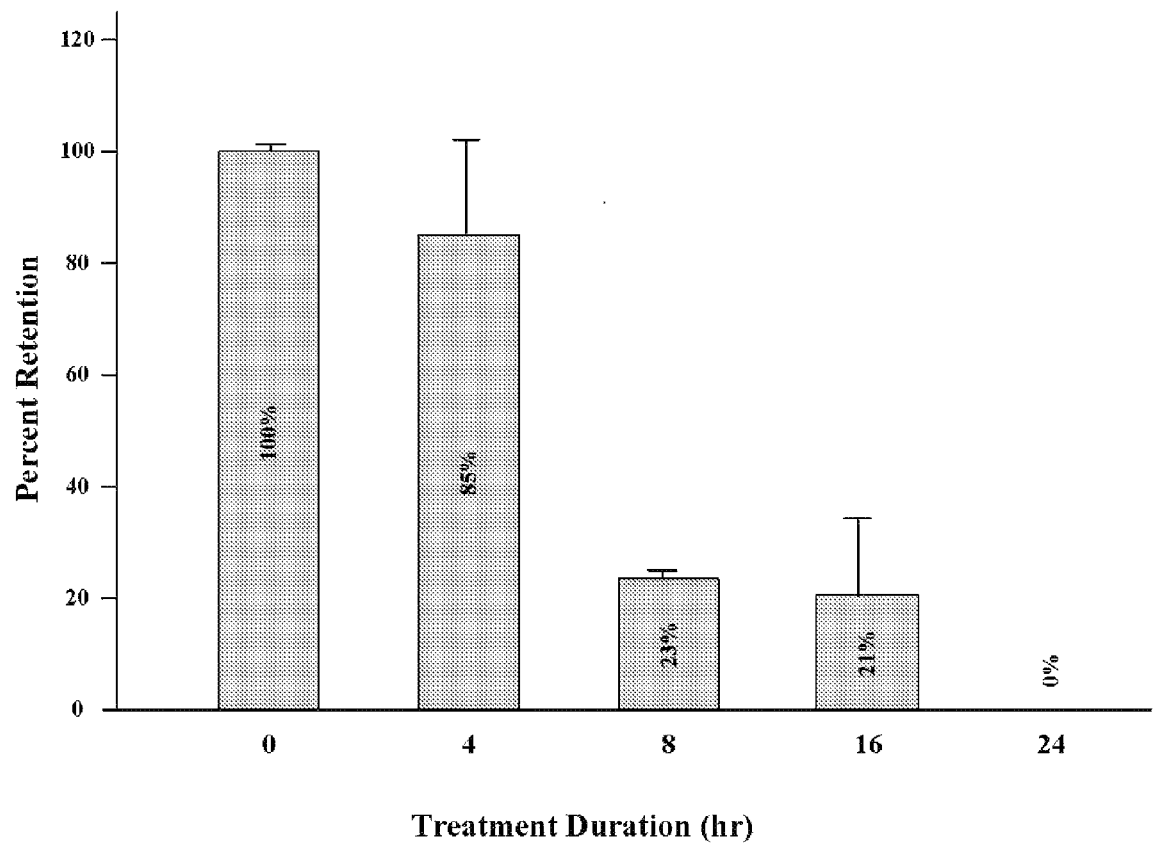
FIG. 10 depicts, graphically, the amount of the material of Example 1 retained on the cornea after various time points—in vitro study.

Quantitative analysis of the residual fluorescence revealed that 85% remained at 4 hours post-application, more than 20% remained at both 8 and 16 hours, while virtually all residual fluorescence was gone by 24 hours (see Table XI). Refer to FIG. 9 to observe representative corneal cross sections exhibiting residual fluorescence and to FIG. 10 for luminescence quantitation.

Conclusion

The formulations of this invention are easy to apply and remain adherent for up to 16 hours. By 24 hours there is no residual fluorescence. This data suggests that these formulations may provide a useful matrix from which to administer sustained drug delivery or to address dry eye, requiring only one application per day. The absence of residual at 24 hours suggests a fresh surface for reapplication on the next day.

TABLE XI

Retention of Formulations (20 mg/mL) on Corneal Surface - Data Details

| Treatment Group | Time Point | Cornea | # Sections Analyzed | Mean Residual Fluorescence | % Above Baseline |
|---|---|---|---|---|---|
| Control | 0 hr | 1 | 4 | 31.63 | *Note: The average |
|  |  | 2 | 4 | 33.36 | native fluorescence |
|  |  | 3 | 7 | 34.86 | observed in all control |
|  | Totals | 3 | 15 | 33.28 ± 1.62 | time points was 32.74. |
| Control | 8 hr | 1 | 8 | 32.55 | This value was |
|  |  | 2 | 8 | 34.09 | subtracted from the |
|  | Totals | 2 | 16 | 33.32 ± 1.09 | mean residual |
| Control | 24 hr | 2 | 6 | 32.93 | fluorescence of the |
|  |  | 5 | 3 | 30.51 | treated specimens to |
|  | Totals | 2 | 9 | 31.72 ± 1.71 | obtain the amount |
| Treated | 0 hr | 1 | 6 | 44.81 | above baseline. The |
|  |  | 2 | 5 | 43.22 | percent above baseline |
|  |  | 3 | 7 | 46.35 | was determined as the |
|  |  | 4 | 7 | 59.43 | percent remaining of |
|  |  | 5 | 8 | 51.94 | the 0 hr time point. |
|  | Totals | 5 | 33 | 49.15 ± 6.62 | 16.41: 100% |
| Treated | 4 hr | 1 | 8 | 45.39 |  |
|  |  | 2 | 8 | 46.5 |  |
|  |  | 3 | 8 | 44.08 |  |
|  |  | 4 | 7 | 44.77 |  |
|  |  | 5 | 6 | 53.02 |  |
|  | Totals | 5 | 37 | 46.75 ± 3.62 | 14.01: 85% |
| Treated | 8 hr | 1 | 7 | 30.89 |  |
|  |  | 4 | 8 | 42.21 |  |
|  | Totals | 2 | 15 | 36.55 ± 8.00 | 3.81: 23% |
| Treated | 16 hr | 1 | 8 | 39.06 |  |
|  |  |  | 7 | 35.99 |  |
|  |  | 5 | 6 | 33.4 |  |
|  | Totals | 3 | 23 | 36.15 ± 2.83 | 3.41: 21% |
| Treated | 24 hr | 1 | 6 | 30.59 |  |
|  |  |  | 7 | 30.68 |  |
|  |  | 3 | 7 | 36.1 |  |
|  |  | 4 | 5 | 29.21 |  |
|  |  | 5 | 7 | 31.22 |  |
|  | Totals | 5 | 32 | 31.56 ± 2.64 | 0: 0% |

Example 14

Epithelial Wound Healing Model

This example was designed to assess the corneal re-epithelialization rate and pattern in scrape wounds after treatment utilizing the material of Example 1.

Procedure

New Zealand White rabbits with a body weight of 7 to 8 kg were used (n=4). Animals were anesthetized with an intramuscular (i.m.) injection of xylazine (5 mg/kg) and ketamine (35 mg/kg). A local anesthetic of proparacaine hydrochloride solution 0.5% (Alcaine, Alcon) was applied to the rabbit eyes. The eyes were taped open with Transpore Tape (3M) to prevent contamination from the eyelashes. The eyeball was raised from its socket with a gentle push at the bottom of the lower eyelid using the back of the scalpel (blunt end). While the eyeball was delicately held between thumb and forefinger, the center of cornea was marked with a sterile 6 mm trephine by gently pressing the trephine. The entire epithelium was gently scraped within the marked 6 mm circle on the cornea using a #15 Bard-Parker blade fitted to a scalpel. Care was taken to scrape the entire epithelium within the marked area.

Figure 11:
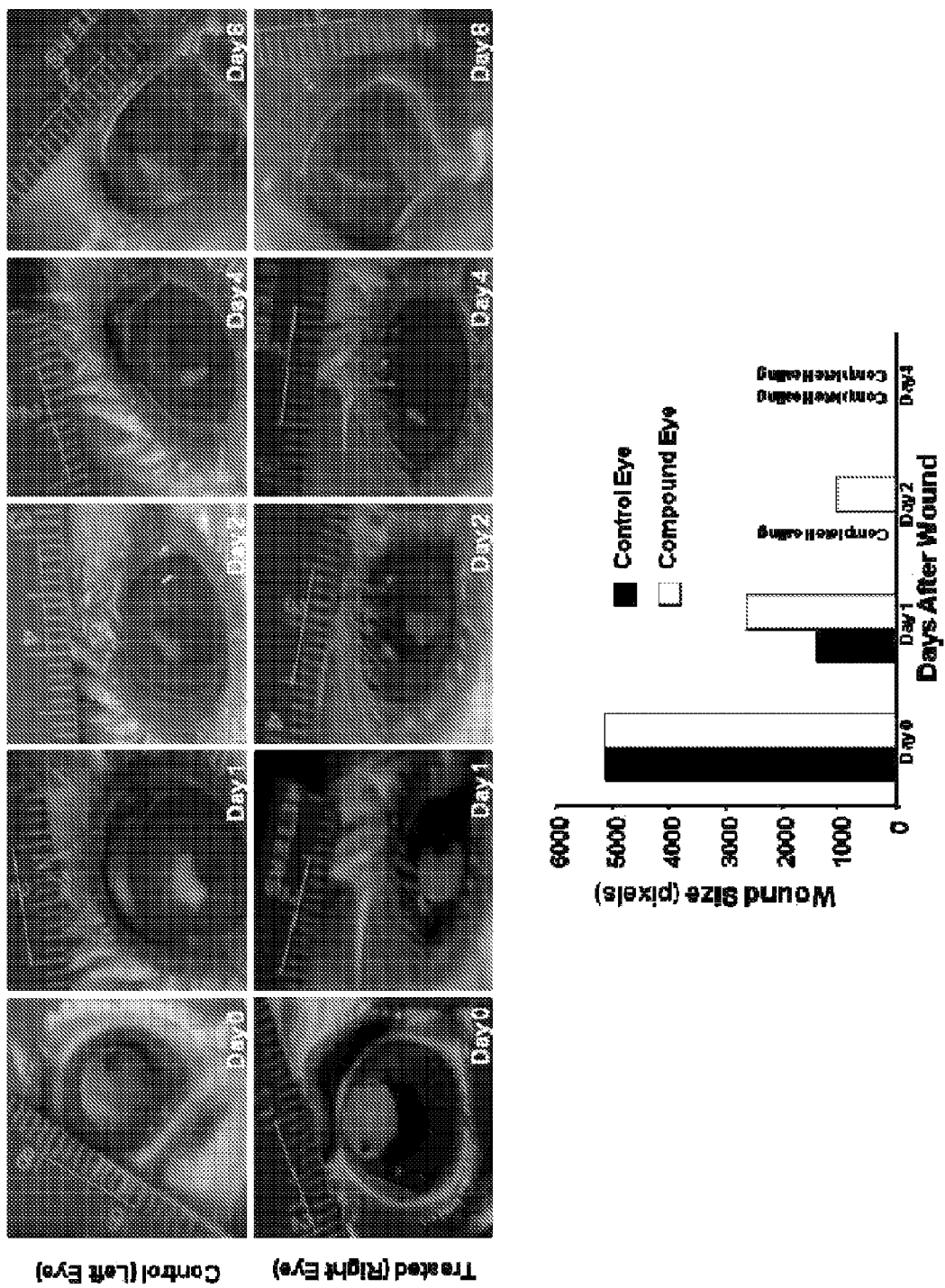
FIG. 11 depicts a series of photographs showing rabbit corneal re-epithelialization in scrape wounds after treatment with the material of Example 1—in vivo study.
Figure 12:
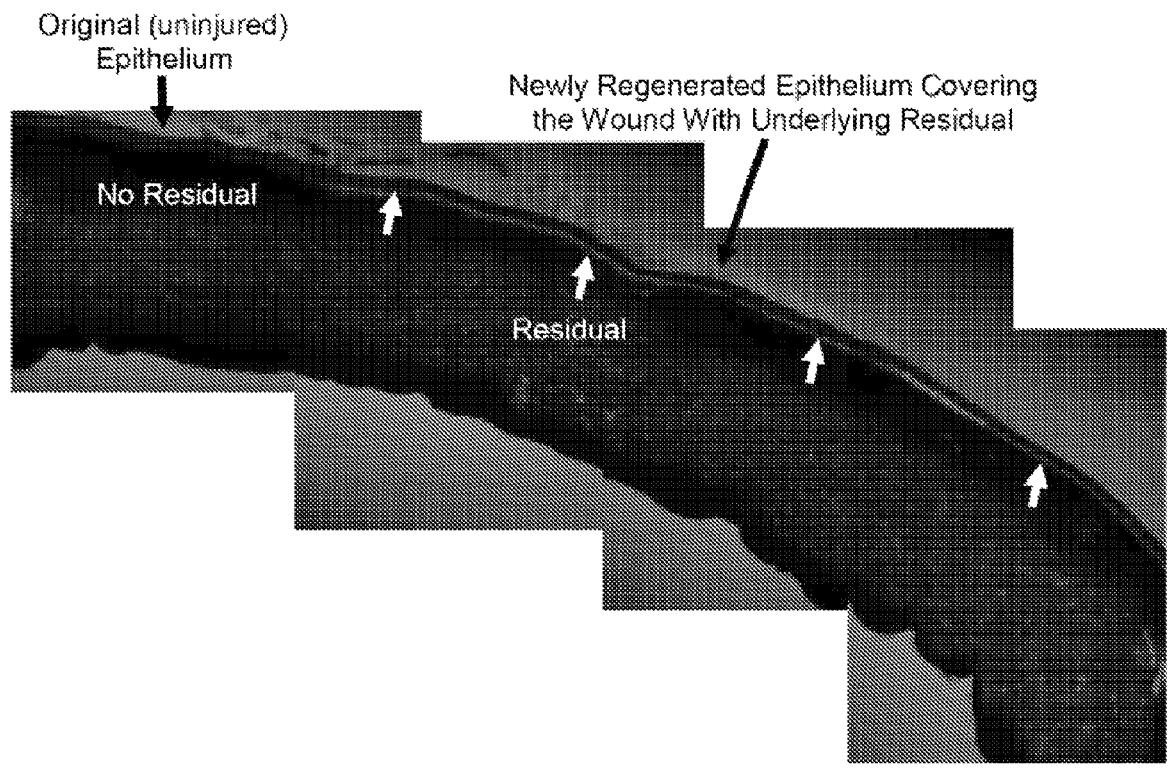
FIG. 12 depicts a cross-section of a cornea showing uninjured epithelium and newly regenerated epithelium covering the wound with underlying residual material of Example 1—in vivo study.

The eye was rinsed with sterile BSS after scraping to remove any adherent loose epithelium. One eye was randomly selected to be treated with compound (10 mg/mL concentration). 100 µL was applied topically and allowed to set for 1 min. The contralateral eye was treated with 100 µL of BSS to serve as a control. Each eye was treated with fluorescein and, under UV exposure, the image was captured to record the wound size at the 0 time point. A ruler was placed adjacent to the cornea for calibration during image analysis. After the eye was photographed, the fluorescein was washed off with BSS. After treatment all eyes were irrigated with BSS, treated with antibiotic moxifloxacin hydrochloride 0.5% (Vigamox, Alcon), and taped closed to prevent the eye from drying during recovery from anesthesia. Elizabethan collars were placed on the animals to prevent them from touching their eyes. Wound size was assessed in all eyes by taking the photos as above on days 1, 2, 4 and 8 following the surgery. The general health and eye condition was monitored once a day and observations were recorded. The corneas were harvested after the 8-day photos were taken. Corneas and were excised, snap frozen and prepared for histological observation.
Results Photos have been taken and quantitative image analyses have been performed. Visual observations and preliminary analysis of the wound healing process suggest that the presence of the adherent film causes a slowing of the re-epithelialization process as shown in FIG. 11, however re-epithelialization does ultimately occur. Histological observations, using a stain that binds with chitosan, reveal that the epithelial cells advance over the adherent film of this invention as shown in FIG. 12. There has been no apparent punctal occlusion from dislodged film remnants.
Conclusion The topical film does not appear to have any toxic or inflammatory effects, but does seem to slow the re-epithelialization process. Clinical benefit would be gained if this protective covering could provide an analgesic effect during the, albeit delayed, re-epithelialization process. Alternatively, it could provide a means to deliver an analgesic agent and/or epithelial/stromal growth promoters. Evidence shows residual film adhered to stroma out to 8 days, which would provide a novel means for sustained drug delivery.

Example 15

Drug Release Model

This example was designed to assess the ability of a modified and treated chitosan material to act as a drug delivery matrix through covalent attachment of a pharmaceutical agent to the chitosan molecule itself and subsequent adherence to the target tissue substrate. The pharmaceutical agent may either remain attached or be cleaved via hydrolytic or enzymatic activity.
Procedure Enzymatic cleavage of a pseudo drug was demonstrated using a dansyl group attached to a backbone through an enzymatically cleavable link. In the diagram below, the simple amide is a prudent target for cleavage by elastase. This example was completed using collagen as the backbone. The linkage was covalently attached to the collagen utilizing naphthalimide photochemistry.

The collagen was suspended in a PBS, pH 7.4, and incubated in the presence of 10 U/mL elastase. After four hours, the collagen was removed by centrifugation and the pseudo drug released was measured by the fluorescence in the supernatant.

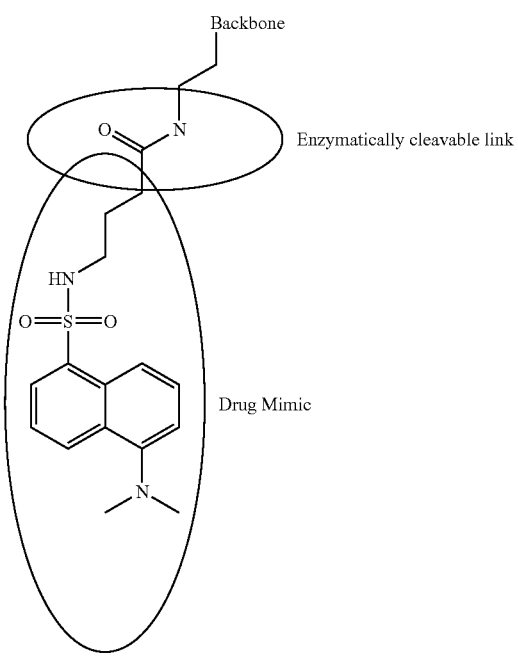

Results

Figure 13:
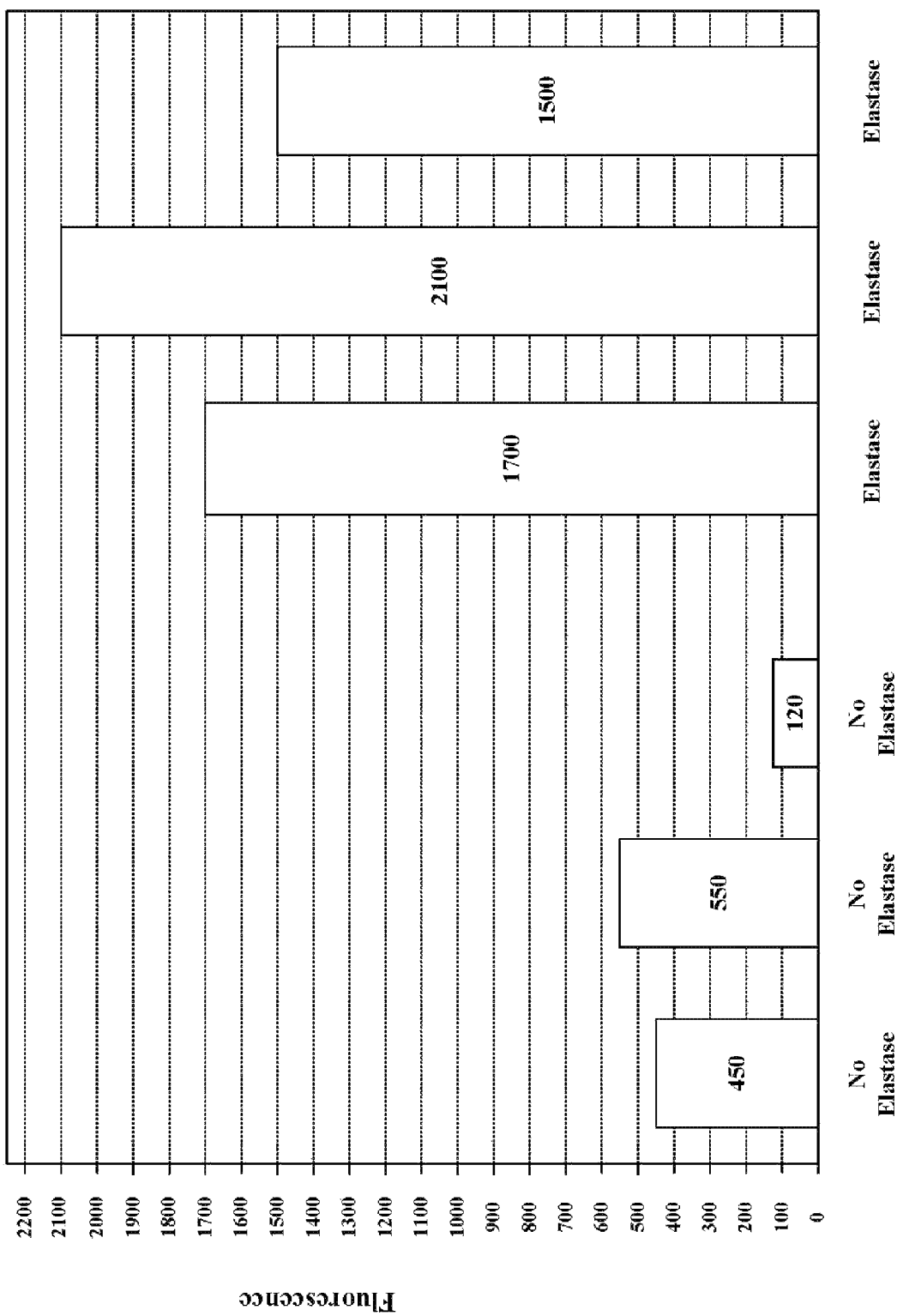
FIG. 13 depicts graphically the enzymatic release of a pseudo drug by elastase from several replicates of a collagen-based model, validating the premise of cleavable drug tethers.

The results of these experiments are shown in FIG. 13. In the absence of the enzyme, the fluorescence was 373±225, in the presence of the enzyme the fluorescence was 1767±305 indicating an enzymatic release of the pseudo drug.
Conclusion This example clearly demonstrates the concept of using a cleavable linker to achieve sustained release of a pharmaceutical agent from a biological macromolecule. While this demonstration illustrates enzymatic-dependent release of a pseudo drug from a collagen model, similar chemistry can be used to deliver pharmaceutical agents from materials of this invention.

Example 16

Demonstration of Antimicrobial Properties

This example was designed to assess the antimicrobial properties of a modified and treated chitosan formulation and utilized the material of Example 1.
Procedure A 0.5 McFarland standard inoculum of organisms was used to prepare a lawn of growth on Remel Sheep Blood agar or Remel Chocolate agar plate (organism dependent). A 50 µL drop of the compound was placed in the middle of the plate. The plates were incubated at 36.5° C. at 6.5% $CO_2$ and observed for inhibition of growth at 24 and 48 hours. The compound was checked for sterility by inoculating a 50 µL drop onto Remel Sheep Blood agar and Remel Chocolate agar plates. Placing a drop of saline on each plate performed a negative control of the test procedure.
Results There was obvious inhibition of growth directly beneath the drop of the compound but not in the adjacent area with the following organisms:
    *Staphylococcus epidermidis*
    *Staphylococcus aureus*
    *Haemophilus influenzae*
    *Pseudomonas aeruginosa*
    *Escherichia coli*

Two organisms appeared to have no apparent inhibition. Inhibition may have been present but unable to be observed by this methodology:

*Enterococcus faecalis*
*Streptococcus pneumoniae*

There was no growth evident on the plates used to check the sterility of the compound, and the negative control areas of the plates reacted as expected.

Conclusion

The literature reports that native chitosan exhibits antimicrobial properties against various microbial organisms. These experiments confirm that the modified and treated chitosan of this invention retains antimicrobial properties, at least against certain microbial organisms.

Example 17

Demonstration of Antifungal Properties

This example was designed to assess the antifungal properties of a modified and treated chitosan formulation and utilized the material of Example 1.

Procedure

The antifungal properties of the material of Example 1 at 10 mg/mL were tested by creating a 0.5 McFarland standard turbidity lawn of organisms on Sab Dex agar. One drop of the compound was placed in the middle of this lawn of organisms and observed for potential antifungal activity. Five different yeast and fungal organisms were tested, including *Candida albicans, Candida glabrata, Candida parapsilosis, Candida krusei*, and *Aspergillus* sp.

Results

Prior to treatment, all of the yeast and fungal organisms grew luxuriantly of the Sab Dex agar media. There was obvious inhibition of growth directly beneath the drop of the compound but not in the adjacent area with the following organisms:

*Candida krusei*
*Candida parapsilosis*

Partial inhibition of growth directly under the central portion of the drop of the test compound was observed with

*Candida albicans*
*Candida glabrata*
*Aspergillus* sp.

Conclusion

The material of Example 1 exhibits some degree of contact-dependent antifungal properties with all fungal organisms tested. Perhaps most importantly, the promotion of fungal growth was not observed in any case. This finding is encouraging in light of the proposed medical uses, where it will be important to discourage, rather than encourage, fungal propagation.

Ocular Delivery Compositions and Methods for Specific Drugs

The present invention also relates to an ocular drug delivery composition including a chitosan matrix and a pharmaceutically effective amount of an ocular drug. The ocular drug is selected from the group consisting of a prostaglandin, a prostamide or a mixture thereof, or a non-steroidal anti-inflammatory drug (NSAID) or a mixture of NSAIDs or a corticosteroid or a mixture of corticosteroids and the composition is adapted to release a therapeutically effective amount of the ocular drug over a period of time. The chitosan matrix includes a treated chitosan, a treated and modified chitosan, or a mixture thereof, where the treated chitosans have a lower apparent molecular weight and higher tissue bond strength than untreated chitosan. The period of time for compositions including a prostaglandin, a prostamide or a mixture thereof is between a day and about 1 year. In certain embodiments, the period of time for compositions including a prostaglandin, a prostamide or a mixture thereof is between about a month and about six months. In other embodiments, the period of time for compositions including a prostaglandin, a prostamide or a mixture thereof is between about a mount and about four months. In other embodiments, the period of time for compositions including a prostaglandin, a prostamide or a mixture thereof is at least three months. In other embodiments, the period of time for compositions including a prostaglandin, a prostamide or a mixture thereof is at least one month. In other embodiments, the period of time for compositions including a prostaglandin, a prostamide or a mixture thereof is at least two months. The period of time for composition including a non-steroidal anti-inflammatory drug (NSAID) or a mixture of NSAIDs or a corticosteroid or a mixture of corticosteroids is between about 0.5 hours and about 36 hours. In certain embodiments, the period of time for composition including a non-steroidal anti-inflammatory drug (NSAID) or a mixture of NSAIDs or a corticosteroid or a mixture of corticosteroids is between about 1 hour and about 36 hours. In other embodiments, the period of time for composition including a non-steroidal anti-inflammatory drug (NSAID) or a mixture of NSAIDs or a corticosteroid or a mixture of corticosteroids is at least 4 hours. In other embodiments, the period of time for composition including a non-steroidal anti-inflammatory drug (NSAID) or a mixture of NSAIDs or a corticosteroid or a mixture of corticosteroids is at least 8 hours. In other embodiments, the period of time for composition including a non-steroidal anti-inflammatory drug (NSAID) or a mixture of NSAIDs or a corticosteroid or a mixture of corticosteroids is at least 16 hours.

The present invention also relates to a method for administering an ocular drug delivery composition of this invention including a prostaglandin, a prostamide or a mixture thereof, to an eye of an animal including a human, where the administering is via injection. The present invention also relates to a method for administering an ocular drug delivery composition of this invention including a non-steroidal anti-inflammatory drug (NSAID) or a mixture of NSAIDs or a corticosteroid or a mixture of corticosteroids, where the administering is via topical administration.

The present invention also provides a pharmaceutical composition for treating an ocular disease or condition. The composition includes a chitosan composition comprising a treated chitosan, a modified chitosan, a modified and treated chitosan, or a mixture thereof, where the treated chitosans exhibit changes in chemical, physical and/or performance properties or characteristics relative to a corresponding untreated chitosan. The composition also includes a therapeutic agent selected from the group consisting of a prostaglandin, a prostamide and a mixture thereof, a non-steroidal anti-inflammatory drug (NSAID) and a mixture of NSAIDs, and a corticosteroid and a mixture of corticosteroids, or a mixture or combination of one or more of these therapeutic agents. The chitosan composition is adapted to release a therapeutically effective amount of the therapeutical agent over a period of time. In certain embodiments, the composition can also include a preservative. The preservative is generally selected from the group consisting of benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and mixtures thereof in a concentration range of about 0.00001% to about 0.05% or about 0.1% (w/v) of the composition. In other embodiments, the composition can also include an excipient. The excipient is generally an ophthalmically compatible excipient. In other embodiments, the composition can also include a buffer. The buffer is generally selected from the group consisting of acetate buffers, citrate buffers, phosphate buffers, borate buffers and mixtures thereof. In other embodiments, the composition can also include a vehicle. The vehicle is generally an ophthalmically compatible vehicle. In certain embodiments, the therapeutic agent is covalently bonded to sites on the chitosan. In other embodiments, the therapeutic agent is covalently bonded to sites on the chitosan via a linker.

The present invention also provides a process for making a pharmaceutical composition for treating an ocular condition. The process includes contacting a chitosan composition comprising a treated chitosan, a modified chitosan, a modified and treated chitosan, or a mixture thereof and a therapeutically effective amount of a pharmaceutical agent to form the pharmaceutical composition. The pharmaceutical composition can be substantially uniform or non-uniform depending on its specific application. Each treated chitosan has been designed to exhibit changes in one or more chemical, physical and/or performance properties or characteristics relative to a corresponding untreated chitosan. The pharmaceutical agent is selected from the group consisting of a prostaglandin, a prostamide and a mixture thereof, a non-steroidal anti-inflammatory drug (NSAID) and a mixture of NSAIDs, and a corticosteroid and a mixture of corticosteroids. In certain embodiments, the pharmaceutical composition can also include a preservative. The preservative is generally selected from the group consisting of benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and mixtures thereof in a concentration range of about 0.00001% to about 0.05% or about 0.1% (w/v) of the composition. In certain embodiments, the pharmaceutical composition can also include an excipient. The excipient is generally an ophthalmically compatible excipient. In certain embodiments, the pharmaceutical composition can also include a buffer. In certain embodiments, the buffer is generally selected from the group consisting of acetate buffers, citrate buffers, phosphate buffers, borate buffers and mixtures thereof. In certain embodiments, the pharmaceutical composition can also include a vehicle. The vehicle is generally an ophthalmically compatible vehicle. In certain embodiments, the therapeutic agent is covalently bonded to sites on the chitosan. In other embodiments, the therapeutic agent is covalently bonded to sites on the chitosan via a linker. The present invention also provides a pharmaceutical composition made by the processes set forth in this paragraph.

The present invention also provides a process for making a pharmaceutical composition for treating an ocular condition. The process includes contacting a chitosan composition comprising a treated chitosan, a modified chitosan, a modified and treated chitosan, or a mixture thereof and a therapeutically effective amount of pharmaceutical agent under conditions to covalently bond the agent to sites on the chitosan. Each treated chitosan exhibits changes in one or more chemical, physical and/or performance properties or characteristics relative to a corresponding untreated chitosan. The pharmaceutical agent is selected from the group consisting of a prostaglandin, a prostamide and a mixture thereof, a non-steroidal anti-inflammatory drug (NSAID) and a mixture of NSAIDs, and a corticosteroid and a mixture of corticosteroids. In certain embodiments, the pharmaceutical composition can also include a preservative. The preservative is generally selected from the group consisting of benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and mixtures thereof in a concentration range of about 0.00001% to about 0.05% or about 0.1% (w/v) of the composition. In certain embodiments, the pharmaceutical composition can also include an excipient. The excipient is generally an ophthalmically compatible excipient. In certain embodiments, the pharmaceutical composition can also include a buffer. The buffer is generally selected from the group consisting of acetate buffers, citrate buffers, phosphate buffers, borate buffers and mixtures thereof. In certain embodiments, the pharmaceutical composition can also include a vehicle. The vehicle is generally an ophthalmically compatible vehicle. In certain embodiments, the therapeutic agent is covalently bonded to sites on the chitosan. In other embodiments, the therapeutic agent is covalently bonded to sites on the chitosan via a linker. The present invention also provides a pharmaceutical composition made by the processes of this paragraph.

The present invention also provides a method for treating an ocular disease or condition. The method includes the step of administering to a patient a pharmaceutical composition comprising a chitosan composition comprising a treated chitosan, a modified chitosan, a modified and treated chitosan, or a mixture thereof and a pharmaceutical agent a prostaglandin, a prostamide and a mixture thereof, a non-steroidal anti-inflammatory drug (NSAID) and a mixture of NSAIDs, and a corticosteroid and a mixture of corticosteroids. Each treated chitosan exhibits changes in one or more chemical, physical and/or performance properties or characteristics relative to a corresponding untreated chitosan. The pharmaceutical composition is adapted to release a therapeutically effective amount of the pharmaceutical agent over a period of time and where the therapeutically effective amount is adapted to treat or cure an ocular disease or condition or ameliorate symptoms of an ocular disease or condition.

The present invention also provides an ocular drug delivery composition comprising a chitosan matrix and a pharmaceutically effective amount of an ocular drug. The ocular drug is selected from the group consisting of a prostaglandin, a prostamide or a mixture thereof, or a non-steroidal anti-inflammatory drug (NSAID) or a mixture of NSAIDs or a corticosteroid or a mixture of corticosteroids. The chitosan matrix comprises a treated chitosan, a modified chitosan, a treated and modified chitosan, or a mixture thereof, where each chitosan exhibits changes in one or more chemical, physical and/or performance properties or characteristics relative to a corresponding untreated chitosan. The ocular drug delivery composition is adapted to release a therapeutically effective amount of the ocular drug over a period of time. In certain embodiments, the period of time for a composition including a prostaglandin, a prostamide or a mixture thereof is between a day and about 1 year. In other embodiments, the period of time for a composition including a prostaglandin, a prostamide or a mixture thereof is between about a month and about six months. In other embodiments, the period of time for a composition including a prostaglandin, a prostamide or a mixture thereof is between about a month and about four months. In other embodiments, the period of time for a composition including a prostaglandin, a prostamide or a mixture thereof is at least three months. In other embodiments, the period of time for a composition including a prostaglandin, a prostamide or a mixture thereof is at least two months. In other embodiments, the period of time for a composition including a prostaglandin, a prostamide or a mixture thereof is at least one month. In other embodiments, the period of time for a composition including a non-steroidal anti-inflammatory drug (NSAID) or a mixture of NSAIDs or a corticosteroid or a mixture of corticosteroids is between about 0.5 hours and about 36 hours. In other embodiments, the period of time for a composition including a non-steroidal anti-inflammatory drug (NSAID) or a mixture of NSAIDs or a corticosteroid or a mixture of corticosteroids is between about 1 hour and about 36 hours. In other embodiments, the period of time for a composition including a non-steroidal anti-inflammatory drug (NSAID) or a mixture of NSAIDs or a corticosteroid or a mixture of corticosteroids is at least 16 hours. In other embodiments, the period of time for a composition including a non-steroidal anti-inflammatory drug (NSAID) or a mixture of NSAIDs or a corticosteroid or a mixture of corticosteroids is at least 8 hours. In other embodiments, the period of time for a composition including a non-steroidal anti-inflammatory drug (NSAID) or a mixture of NSAIDs or a corticosteroid or a mixture of corticosteroids is at least 4 hours.

The present invention also provides a method for administering an ocular drug delivery composition. The method includes administering an effective amount of the composition via injection to an eye, or tissue surrounding the eye, of an animal including a human. The composition includes a treated chitosan, a modified chitosan, a treated and modified chitosan, or a mixture thereof, where each chitosan exhibits changes in one or more chemical, physical and/or performance properties or characteristics relative to a corresponding untreated chitosan, and a prostaglandin, a prostamide or a mixture thereof.

The present invention also provides a method for administering an ocular drug delivery composition. The method includes administering an effective amount of the composition topically to an eye of an animal including a human. The composition includes a treated chitosan, a modified chitosan, a treated and modified chitosan, or a mixture thereof, where each chitosan exhibits changes in one or more chemical, physical and/or performance properties or characteristics relative to a corresponding untreated chitosan, and a non-steroidal anti-inflammatory drug (NSAID) or a mixture of NSAIDs or a corticosteroid or a mixture of corticosteroids.

The present invention also provides a pharmaceutical composition for treating an ocular disease or condition. The composition includes a treated chitosan, a modified chitosan, a treated and modified chitosan, or a mixture thereof, where each chitosan exhibits changes in one or more chemical, physical and/or performance properties or characteristics relative to a corresponding untreated chitosan, and a therapeutic agent selected from the group consisting of a prostaglandin, a prostamide, a non-steroidal anti-inflammatory drug (NSAID), and a corticosteroid, and mixtures, derivatives, salts and esters thereof.

The present invention also provides a process for making a pharmaceutical composition for treating an ocular condition. The process includes the step of contacting a modified chitosan and a therapeutic agent, wherein the therapeutic agent is selected from the group consisting of a prostaglandin, a prostamide, a non-steroidal anti-inflammatory drug (NSAID), and a corticosteroid, and mixtures, derivatives, salts and esters thereof.

The present invention provides a method for treating an ocular disease or condition. The method includes the step of administering to an eye of a patient a pharmaceutical composition comprising a treated chitosan, a modified chitosan, a treated and modified chitosan, or a mixture thereof and a therapeutic agent. The therapeutic agent selected from the group consisting of a prostaglandin, a prostamide, a non-steroidal anti-inflammatory drug (NSAID), and a corticosteroid, and mixtures, derivatives, salts and esters thereof, thereby treating the ocular disease or condition. Each treated chitosan are designed to exhibit changes in one or more chemical, physical and/or performance properties or characteristics relative to a corresponding untreated chitosan.

The present invention provides an ocular drug delivery composition comprising a chitosan matrix and a pharmaceutically effective amount of an ocular drug. The ocular drug is selected from the group consisting of a non-steroidal anti-inflammatory drug (NSAID) or a mixture of an NSAID or a corticosteroid or a mixture of corticosteroids. The chitosan matrix includes a treated chitosan, a modified chitosan, a modified and treated chitosan, or a mixture thereof, where each chitosan exhibits changes in one or more chemical, physical and/or performance properties or characteristics relative to a corresponding untreated chitosan. The composition affords equivalent therapeutic activity at a lower pharmaceutically effective amount compared to a composition in the absence of the chitosan matrix. The compositions of this invention including the chitosan matrix are capable of increasing a tissue drug concentration compared to a composition in the absence of the chitosan matrix at an equivalent drug concentration in the composition. Thus, the compositions of this invention afford a lower pharmaceutically effective amount of the drug compared to the composition in the absence of the chitosan matrix. In certain embodiments, the lower pharmaceutically effective amount is at least 10% less than an amount of the drug in a comparable composition in the absence of the chitosan matrix. In other embodiments, the lower pharmaceutically effective amount is at least 20% less than an amount of the drug in a comparable composition in the absence of the chitosan matrix. In other embodiments, the lower pharmaceutically effective amount is at least 30% less than an amount of the drug in a comparable composition in the absence of the chitosan matrix. In other embodiments, the lower pharmaceutically effective amount is at least 40% less than an amount of the drug in a comparable composition in the absence of the chitosan matrix. In other embodiments, the lower pharmaceutically effective amount is at least 50% less than an amount of the drug in a comparable composition in the absence of the chitosan matrix. In other embodiments, the lower pharmaceutically effective amount is at least 60% less than an amount of the drug in a comparable composition in the absence of the chitosan matrix. In other embodiments, the lower pharmaceutically effective amount is at least 70% less than an amount of the drug in a comparable composition in the absence of the chitosan matrix. In other embodiments, the lower pharmaceutically effective amount is at least 80% less than an amount of the drug in a comparable composition in the absence of the chitosan matrix. In other embodiments, the lower pharmaceutically effective amount is at least 90% less than an amount of the drug in a comparable composition in the absence of the chitosan matrix. In other embodiments, the lower pharmaceutically effective amount is at least 95% less than an amount of the drug in a comparable composition in the absence of the chitosan matrix.

The pharmaceutical composition is advantageously ophthalmically acceptable and may include one or more conventional excipients useful in ophthalmic compositions. The present compositions preferably include a major amount of liquid water. The present compositions may be, and are preferably, sterile, for example, prior to being used in the eye.

The present compositions preferably include at least one buffer component in an amount effective to control and/or maintain the pH of the composition and/or at least one tonicity component in an amount effective to control the tonicity or osmolality of the compositions; preferably the tonicity and/or osmolality will be substantially isotonic to the vitreous humor. More preferably, the present compositions include both a buffer component and a tonicity component.

The buffer component and tonicity component may be chosen from those which are conventional and well known in the ophthalmic art. Examples of such buffer components include, but are not limited to, acetate buffers, citrate buffers, phosphate buffers, borate buffers and the like and mixtures thereof. Phosphate buffers are particularly useful. Useful tonicity components include, but are not limited to, salts, particularly sodium chloride, potassium chloride, mannitol and other sugar alcohols, and other suitable ophthalmically acceptable tonicity components and mixtures thereof.

The amount of buffer component employed preferably is sufficient to maintain the pH of the composition in a range of about 6 to about 8, more preferably about 7 to about 7.5. The amount of tonicity component employed preferably is sufficient to provide an osmolality to the present compositions in a range of about 200 to about 400, more preferably about 250 to about 350, mOsmol/kg respectively. Advantageously, the present compositions are substantially isotonic.

The present compositions may include one or more other components in amounts effective to provide one or more useful properties and/or benefits to the present compositions. For example, although the present compositions may be substantially free of added preservative components, in other embodiments, the present compositions include effective amounts of preservative components, preferably such components which are more compatible with the tissue in the posterior segment of the eye, into which the composition is placed, than benzyl alcohol. Examples of such preservative components include, without limitation, benzalkonium chloride, chlorhexidine, PHMB (polyhexamethylene biguanide), methyl and ethyl parabens, hexetidine, chlorite components, such as stabilized chlorine dioxide, metal chlorites and the like, other ophthalmically acceptable preservatives and the like and mixtures thereof. The concentration of the preservative component, if any, in the present compositions is a concentration effective to preserve the composition, and is often in a range of about 0.00001% to about 0.05% or about 0.1% (w/v) of the composition.

Experiments Relating to Ocular Delivery of Specific Drugs

Example 18

In Vivo Corneal Retention Model

This example was designed to determine the kinetics of retention on the corneal surface of an in vivo rabbit eye model and utilized the material of Example 1. Furthermore, this example was designed to assess the ability of a modified and treated chitosan material to act as a drug delivery matrix through, ultimately, mixture of free drug within the prepared chitosan material and subsequent adherence to the target tissue substrate with elution of the drug into the tissue via diffusion.

Procedure

Four New Zealand White rabbits with a body weight of 5 to 6 lbs were used for this study. The rabbit's eyes were randomized. One drop of sterile BSS was put in the control eyes and 20 µL of the material of Example 1 was applied, using a 5-50 µL pipettor, onto the experimental eyes. The corneas were harvested at 2 hours. The rabbits were anesthetized at the time of harvest with isofluorane at 2.0 to 3.5% in a 40%/60% oxygen/air mixture, followed by euthanization. Experiments were staggered at 1 hour intervals to allow time for analysis immediately upon harvest. The corneas were stained with calcofluor and evaluated topographically using fluorescence microscopy to assess retention of the modified chitosan material. Representative images were captured and stored for each cornea.

Results

Topographical evaluation of the surface of the corneas using fluorescence microscopy confirmed continued presence of the materials of Example 12 hours after application. Refer to FIG. 14 to observe the positive calcofluor staining observed on experimental eyes vs. the non-specific staining observed on control eyes.

Conclusion

The materials of Example 1 are easy to apply and remain adherent for up to 2 hours under in vivo conditions. This data suggests that these formulations may provide a useful matrix from which to administer sustained or improved drug delivery or to address dry eye. Chitosan formulations can be prepared which adhere to the cornea for a period of time between about 10 minutes and about 30 days.

Modified Chitosan/Ketorolac Tromethamine (KT) Experimental Section

Example 19

Preparation of Modified Chitosan/KT Products

This example illustrates the incorporation of ketorolac tromethamine (KT) in a chitosan composition of this invention for use as a KT delivery system.

First, a 10 mg/mL solution was prepared from freeze-dried materials of Example 1 by dilution of the solid material with PBS. The resultant solution was steam sterilized. Next, a KT solution was prepared at a concentration of 0.285% (w/v) in sterile saline and sterilized using syringe driven filter sterilization cartridge (Millex-GC). Finally, the modified chitosan solution and the KT solution were combined in a ratio to yield a final modified chitosan concentration of 3 mg/mL and a final KT concentration of 0.2% in a sterile vial. The combined material was then mixed well by placing on a wrist action shaker for one hour. The pH of the final formulation was then measured.

Example 20

KT Drug Delivery from a Modified Chitosan/KT Product

This example was designed to compare the ocular delivery performance of a currently marketed KT formulation (Allergan's Acular LS®) with a proprietary delivery matrix of the current invention in an in vivo rabbit model. This study used the material of Example 19.

Procedure

Nine New Zealand White rabbits with a body weight of 5 to 7 lbs were used for this study. The rabbits and their eyes were randomized to various treatment groups (see below). The appropriate compound was dropped onto the experimental eye; the other eye remained untreated. After instillation of the drops, the rabbits were monitored continuously for the first 15 to 20 minutes and every 15 minutes thereafter until the time of collection. The rabbits were anesthetized using isofluorane at 2.0 to 3.5% in a 40%/60% oxygen/air mixture prior to the collection of aqueous humor. A survey of the literature for drug delivery applications of this type would show that it is common practice to evaluate formulations via topical ocular application followed by quantitation of drug levels in the corneal aqueous humor at various time points post application. Therefore, 100 µL of aqueous humor was collected from each eye at the appropriate time points and stored at −80° C. until analyzed.

Group 1 consisted of three rabbits. The experimental eye of each rabbit was treated with 50 µL of the materials of Example 19 at 3 mg/mL. The other eyes remained untreated. Aqueous humor was collected from the treated eyes at the following time points: 1 hr and 4 hrs. Aqueous humor was collected from the untreated eye of one of the rabbits at 1 hr to serve as a background control for analysis if needed.

Group 2 consisted of two rabbits. The experimental eye of each rabbit was treated with 50 µL of Acular LS® (the recommended dosage). The other eye remained untreated. Aqueous humor was collected from the treated eyes at the following time points: 1 hour and 4 hours.

Aqueous humor samples were analyzed by Reverse Phase High Performance Liquid Chromatography (HPLC). Prior to analysis samples were diluted 1:1 with methanol, refrigerated for 1 hour and centrifuged to eliminate any biological interferences. All samples and standards were treated according to this sample preparation step. Analyte recoveries were evaluated and deemed acceptable for this analysis. HPLC separation was accomplished using a standard C18 analytical column, a mobile phase consisting of methanol/water/acetic acid (55/44/1) and a 1.0 mL/minute flow rate. Detection and quantitation was accomplished using a UV-Visible detector at 254 nm.

Results

Figure 15:
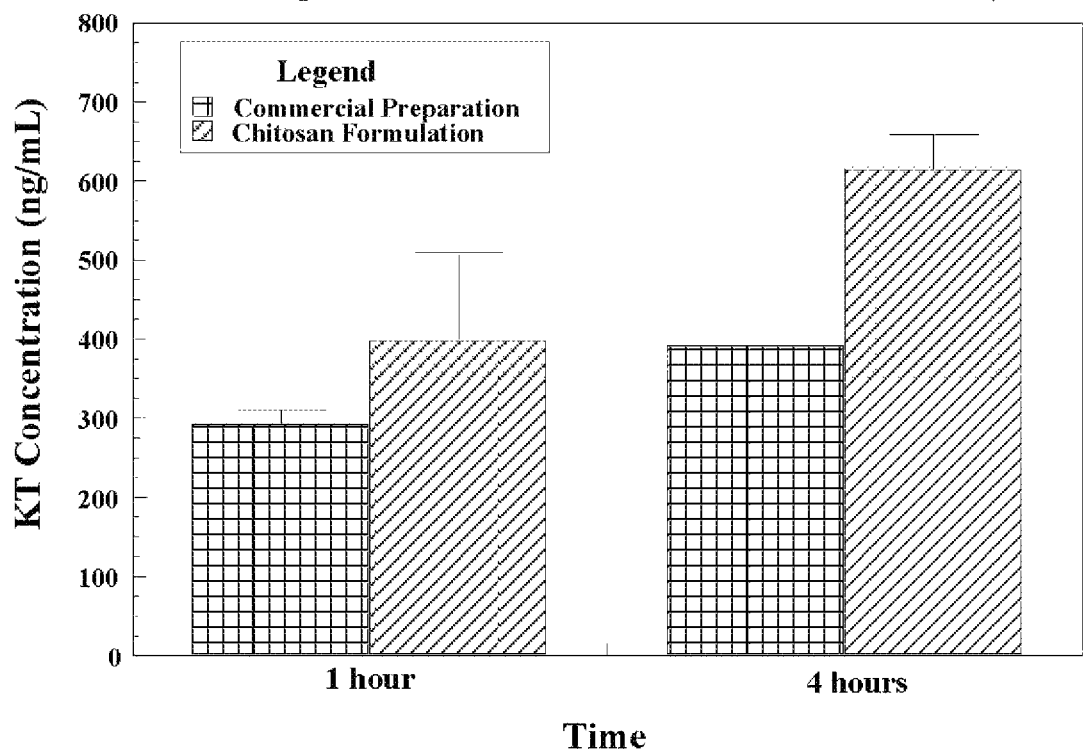
FIG. 15 depicts comparable, if not superior, delivery of ketorolac tromethamine (KT) from the material of Example 19 (0.2% KT) compared to a commercial preparation (0.4% KT).

FIG. 15 shows data obtained from this study. The currently marketed Acular-LS® contains the active drug at a concentration of 0.4% and the formulation of this invention is at 0.2%. Despite having 50% less active drug, delivery from the formulation of this invention exceeds that of the currently marketed product at time points of one and four hours post-application. KT concentrations delivered by the formulation of this invention were at 136% and 157% of Acular-LS® at 1 and 4 hours respectively.

Conclusions

The materials of Example 19 show tremendous promise as a means to improve the delivery of KT to the eye, allowing substantial lowering of the active pharmaceutical ingredient (API) yet obtaining comparable if not superior delivery.

The modified chitosan, KT compositions described herein can be used to successfully treat ocular conditions, such as inflammation and infection. Therapeutically effective modified chitosan formulations can also be prepared with other NSAIDs such as (without limitation): (1) salicylates, for example Acetylsalicylic acid, Amoxiprin, Benorilate, Choline magnesium salicylate, Diflunisal, Faislamine, Methyl salicylate, Magnesium Salicylate, Salicyl salicylate (salsalate); (2) Arylalkanoic acids, for example Diclofenac, Aceclofenac, Acemetacin, Bromfenac, Etodolac, Indometacin, Nabumetone, Sulindac, Tolmetin (3) 2-Arylpropionic acids (profens), for example Ibuprofen, Carprofen, Fenbufen, Fenoprofen, Flurbiprofen, Ketoprofen, Loxoprofen, Naproxen, Oxaprozin, Tiaprofenic acid, Suprofen; (4) N-Arylanthranilic acids (fenamic acids), for example Mefenamic acid, Meclofenamic acid; (5) Pyrazolidine derivatives, such as Phenylbutazone, Azapropazone, Metamizole, Oxyphenbutazone, Sulfinpyrazone; (6) Oxicams, such as Piroxicam, Lomoxicam, Meloxicam and Tenoxicam; (7) COX-2 Inhibitors, such as Celecoxib, Etoricoxib, Lumiracoxib, Parecoxib, Rofecoxib, and Valdecoxib; (8) Sulphonanilides such as Nimesulide, and other NSAIDs such as Licofelone and Omega-3 fatty acids.

Modified Chitosan/Prednisolone Acetate
Experimental Section

Example 21

Preparation of Modified Chitosan/PA Products

This example illustrates the incorporation of prednisolone acetate (PA) in a modified chitosan composition of this invention for use as a PA delivery system.

Procedure

For this particular application the drug is incorporated into the formulation during the aforementioned reconstitution step. This facilitates sterilization of the drug product in tandem with the formulation of this invention. Freeze dried material of Example 4 is weighed out and diluted with sterile saline to yield the desired final modified chitosan concentration of 3 mg/mL. The modified chitosan was allowed to solubilize overnight prior to the addition of the PA. Prior to autoclaving the drug was weighed out in an amount to yield the desired final drug concentration (0.05%) when added to the modified chitosan/saline mixture. The mixture may be heated prior to autoclaving to help the dissolution of the active drug. The formulation was then autoclaved and then stirred overnight. The sterilized material may be diluted with an appropriate diluent while warm or after cooling. Such diluents include any carrier used in drug delivery.

Example 22

Alternate Method for Preparation of Modified Chitosan/PA Products

This example illustrates an alternate procedure for incorporating prednisolone acetate (PA) in a modified chitosan composition of this invention for use as a PA delivery system using DMSO as a cosolvent.

Procedure 2.7 mL of a 10 mg/mL modified chitosan solution of materials of Example 4 was placed in a 20 mL vial. 225 µL of a 2% PA in DMSO solution was added dropwise to the vial. 1 mL of DI water was then added to the vial. Next, 500 µL of methanol was added dropwise to the vial. The resulting solution was transferred to a round bottom flask and rotovaped to produce a hydrogel. The hydrogel was then scraped out of the flask, placed in a graduated cylinder, and reconstituted to the desired volume (9 mL in the example). The reconstituted material was sterilized in an autoclave.

Example 23

Alternate Method for Preparation of Modified Chitosan/PA Products

This example illustrates an alternate procedure for incorporating prednisilone acetate (PA) in a modified chitosan composition of this invention for use as a PA delivery system using ethyl acetate as a cosolvent.

PA was dissolved in ethyl acetate to form a PA ethyl acetate solution having a desired PA concentration. A desired amount of a 10 mg/mL modified chitosan solution of materials of Example 4 was placed in a 20 mL vial. The PA ethyl acetate solution was added to the vial to give a PA concentration of 0.05%. The resulting solution was gently heated to a temperature of about 45° C. to evaporate the ethyl acetate. Optionally, a gentle flow of $N_2$ can be directed onto the surface of the solution to speed removal the ethyl acetate or facilitate the removal of any dissolved ethyl acetate.

Example 24

PA Drug Delivery for a Modified Chitosan/PA Product

This example was designed to compare the ocular delivery performance of a currently marketed prednisolone acetate (PA) formulation (Allergan's Pred Forte®) with a proprietary delivery matrix of the current invention in an in vivo rabbit model. This study used the material of Example 21.

Procedure

Twelve New Zealand White rabbits with a body weight of 5 to 8 lbs were randomized to various treatment groups (see below). The appropriate compound was dropped onto the left eye; the right eye remained untreated. After instillation of the drops, the rabbits were monitored continuously for the first 15 to 20 minutes and every 15 minutes thereafter until the time of collection. The rabbits were anesthetized using isoflurane at 2.0 to 3.5% in a 40%/60% oxygen/air mixture prior to the collection of aqueous humor. A survey of the literature for drug delivery applications of this type would show that it is common practice to evaluate formulations via topical ocular application followed by quantitation of drug levels in the corneal aqueous humor at various time points post application. Therefore, 100 μL of aqueous humor was collected from each eye at the appropriate time points and stored at −80° C. until analyzed.

Group 1 consisted of three rabbits. The left eye of each rabbit was treated with 35 μL of Pred Forte® (the recommended dosage). The right eyes remained untreated. Aqueous humor was collected from both eyes at the 4 hour time point.

Group 2 consisted of three rabbits. The left eye of each rabbit was treated with 35 μL of the materials of Example 21 at 7.2 mg/mL. The right eyes remained untreated. Aqueous humor was collected from both eyes at the 4 hour time point.

Group 3 consisted of three rabbits. The left eye of each rabbit was treated with 35 μL of Pred Forte® (the recommended dosage). The right eyes remained untreated. Aqueous humor was collected from both eyes at the 1 hour time point.

Group 4 consisted of three rabbits. The left eye of each rabbit was treated with 35 μL of the materials of Example 21 at 7.2 mg/mL. The right eyes remained untreated. Aqueous humor was collected from both eyes at the 1 hour time point.

Aqueous humor samples were analyzed by Reverse Phase High Performance Liquid Chromatography. Prior to analysis samples were diluted 1:1 with methanol, refrigerated for 1 hour and centrifuged to eliminate any biological interference. All samples and standards were treated according to this sample preparation step. Analyte recoveries were evaluated and deemed acceptable for this analysis. HPLC separation was accomplished using a standard C18 analytical column, a mobile phase consisting of IPA/water/$H_3PO_4$ (25/74.8/0.2) and a 1.0 mL/minute flow rate. Detection and quantitation was accomplished using a UV-Visible detector at 245 nm.

Results

Figure 16:
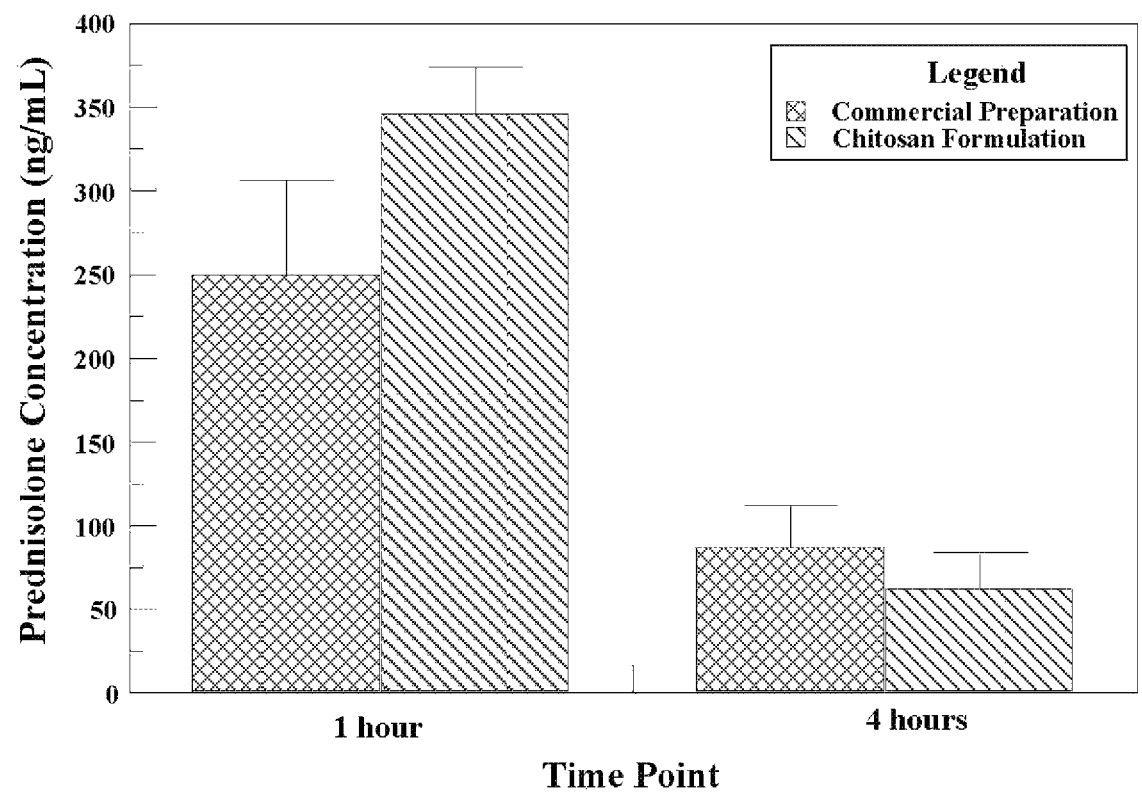
FIG. 16 depicts comparable, if not superior, delivery of prednisolone acetate (PA) from the material of Example 21 (0.05% PA) compared to a commercial preparation (1% PA).

FIG. 16 contains a bar graph that summarizes the data obtained from this study. The currently marketed Pred Forte® contains the active drug at a concentration of 1.0% and the formulation of this invention is at 0.05%. Despite having 20 times less active drug, delivery from the formulation of this invention exceeds that of the currently marketed product at the one hour time point (138% of Pred Forte®) and was only slightly lower (71% of Pred Forte®) 4 hours post-application.

Conclusions

The materials of Example 21 show tremendous promise as a means to improve the delivery of PA to the eye, allowing substantial lowering of the active pharmaceutical ingredient (API) yet obtaining comparable if not superior delivery.

The modified chitosan, prednisolone acetate compositions described herein can be used to successfully treat anterior ocular conditions, such as inflammation and infection. Therapeutically effective modified chitosan formulations can also be prepared with other steroids such as (without limitation) 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In one embodiment, cortisone, dexamethasone, fluocinolone, hydrocortisone, methylprednisolone, prednisolone, prednisone, and triamcinolone, and their derivatives, are preferred steroids.

Modified Chitosan/Bimatoprost Experimental Section

Example 25

Preparation of Modified Chitosan/Bimatoprost Products

This example illustrates the covalent attachment of bimatoprost to a modified chitosan composition of this invention for use as an enzyme released bimatoprost delivery system.

Procedure

Figure 17:
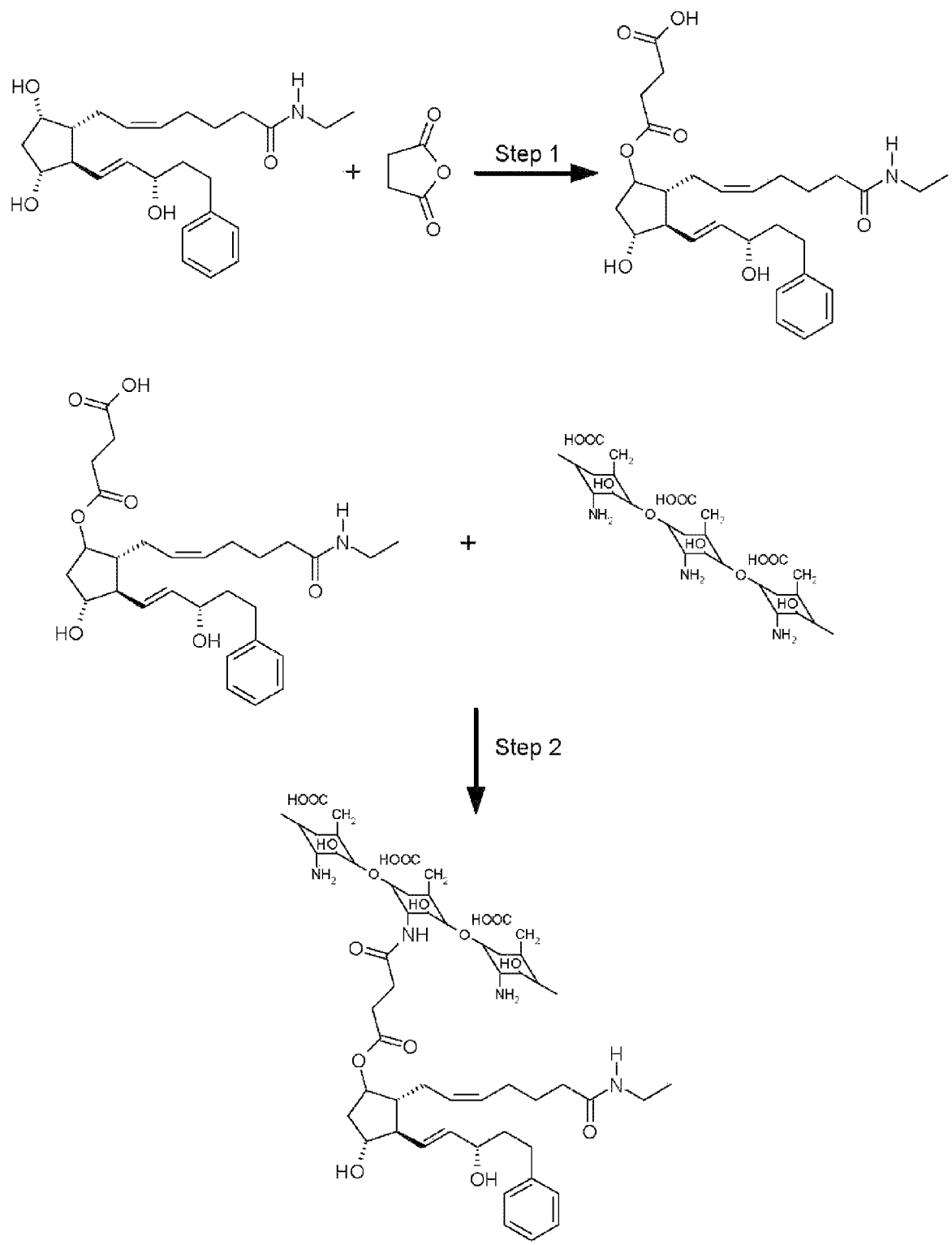
FIG. 17 depicts the synthetic strategy for the covalent attachment of bimatoprost to the chitosan backbone. The bimatoprost is first reacted with succinic anhydride, which provides a linker attached to an alcohol functional group on the bimatoprost. In the second step, the free acid end of the linker is attached to the chitosan backbone utilizing EDC coupling.

The covalent attachment of bimatoprost was accomplished in two steps. In the first step, see FIG. 17, a tether was added to the bimatoprost molecule providing a suitable molecular structure for the attachment to the chitosan backbone. The attachment of the bimatoprost to the tether created an enzymatically cleavable link that upon enzymatic hydrolysis would result in a localized release of unmodified Bimatoprost. In the second step, see FIG. 17, the linker modified Bimatoprost was attached to a chitosan backbone of the modified chitosan materials of Example 1. The covalently modified, drug loaded chitosan material can be used for subsequent localized delivery of the bimatoprost over a prolonged delivery phase.

Step 1: Linker Attachment to Bimatoprost 200 mg of bimatoprost, 48 mg of succinic anhydride, 147 mg of 4-dimethylamino pyridine, 74 μL of triethyl amine and 4 mL dichloromethane are mixed together and placed on a shaker for 20 minutes at room temperature. Four mL of hexane were added to the solution to precipitate the linker-modified bimatoprost. After precipitation, the solvents were evaporated under reduced pressure until only a thick oily layer was left. 10 mL of 0.1M calcium chloride (pH=8) was added and the solution volume reduced to near dryness under reduced pressure. 10 mL of deionized (DI) water was added to redissolve all material. The redissolved sample was then placed in a 50 mL centrifuge vial and acidified with 1M HCl to a pH 4. The solution turned a milky white as the product precipitated. The product was collected by centrifugation for 10 minutes at 3850×G.

Step 2: Attachment to Modified Chitosan

The material of Example 1 was reconstituted in sterile saline to produce a 10 mg/mL solution having a total volume of 10 mL. 0.11 g EDC and 0.165 g NHS were added to the solution with stirring with a magnetic stir bar. The linker-modified bimatoprost from Step 1 was added to the 10 mg/mL modified chitosan solution. The pH of the solution was adjusted to a pH between 6.5 and 7 using 6M NaOH and/or HCl and the pH adjusted solution was stirred for 72 hours. The pH of the resulting solution was then brought to pH 9 by the addition of 6M NaOH to quench the reaction and to precipitate the modified chitosan/bimatoprost product. The precipitated modified chitosan/bimatoprost product and the supernatant were transferred to a 50 mL beaker, and 30 mL of 10% lactic acid was added and the precipitate was allowed to redissolve. The modified chitosan/bimatoprost product was re-precipitated with addition of 6M NaOH. This step was designed to eliminate dissolved residuals that are discarded as part of the supernatant. The material was transferred to centrifuge tubes and centrifuged at 3850×G for 10 minutes. The precipitate was collected, and the solid modified chitosan/bimatoprost product was transferred to dialysis tubing and dialyzed versus 10% acid until the modified chitosan dissolved. The dissolved modified chitosan/bimatoprost product was dialyzed versus water for a minimum of 3 hours. The modified chitosan/bimatoprost product was dialyzed versus water two additional times. The dialysis steps remove excess acid and any unattached bimatoprost/linker from the modified chitosan/bimatoprost product. The pH of the dialysate was measured with pH paper and the pH was recorded. The modified chitosan/bimatoprost product was then dialyzed versus sterile PBS until the dialysate had a pH between 5.7 and 6.0. The modified chitosan/bimatoprost product was then dialyzed against water for 3 hours, repeat for a total of 2 times. The modified chitosan/bimatoprost product was then transferred to a freeze dry flask and refrigerated at −80° C. overnight. The modified chitosan/bimatoprost product was freeze dried. The freeze dried material makes for convenient storage and makes reconstitution at the desired concentration simple. The freeze dried product can then be reconstituted at the desired concentration with sterile PBS and autoclaved to provide a sterile product.

IR Analysis of the Modified Chitosan/Bimatoprost Product

The covalent attachment of the bimatoprost to the modified chitosan materials of Example 1 was studied by FTIR according to the following procedure.

100 mg of dry potassium bromide (KBr) were weighed out. 1 mg of the freeze dried modified chitosan/bimatoprost product was weighed out. The modified chitosan/bimatoprost product and KBr was ground into fine particles using a mortar and pestle, the mixture was scraped from the bottom and the grinding was repeated to ensure complete mixing. The mixture was placed in an 80° C. oven for a minimum of 24 hours. Using a hydraulic press, the mixture was pressed for 5 minutes at 15,000 total pounds of pressure under a vacuum to create a translucent pellet. The pellets were analyzed using a Thermo-Nicolet FT-IR instrument, 16 scans were run on each sample.

Figure 18:
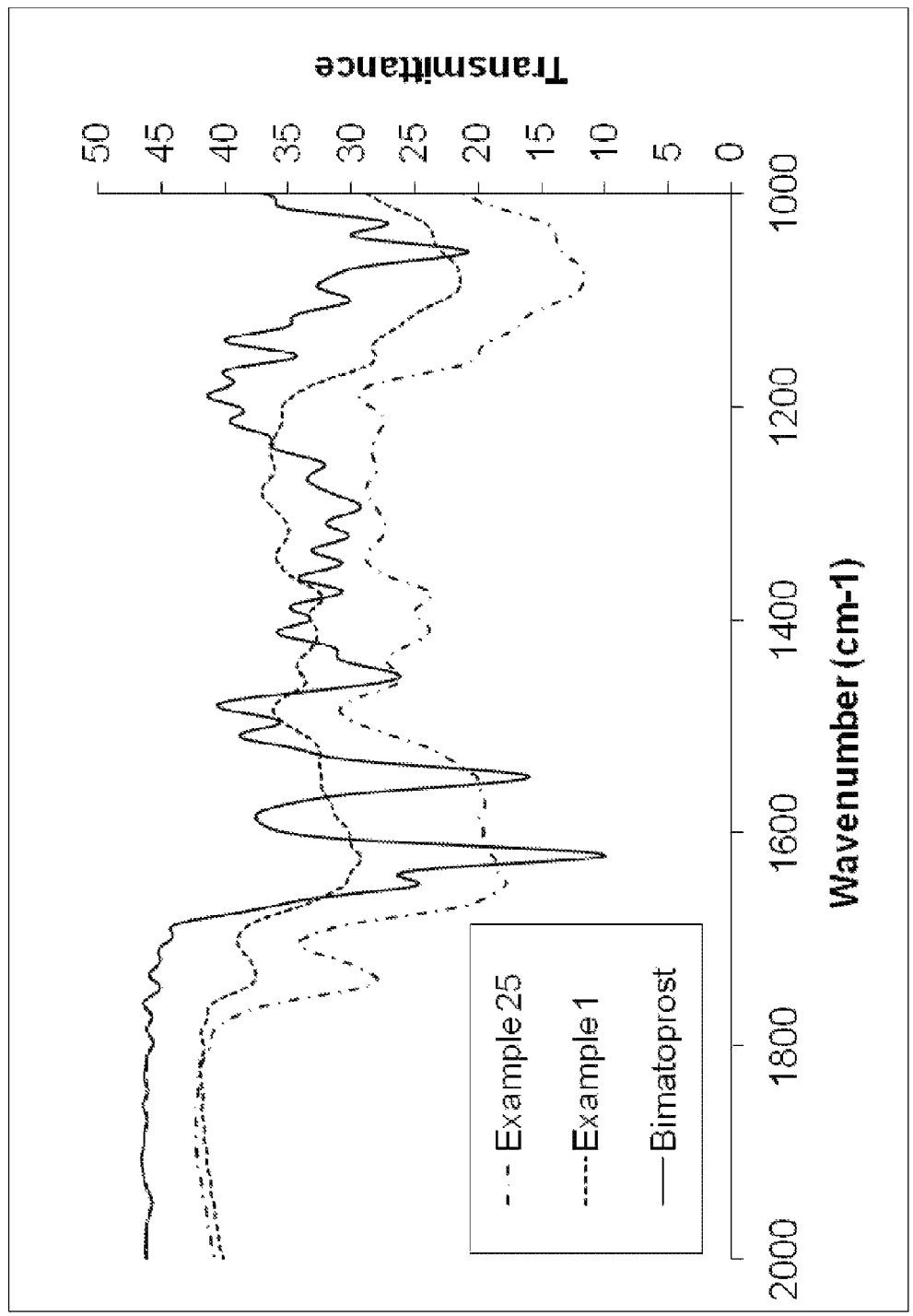
FIG. 18 depicts the FT-IR spectra for the material of Example 1, bimatoprost alone, and the material of Example 25 (the material of Example 1 having bimatoprost covalent attachment thereto). The bands characteristic of bimatoprost at 1550 $cm^{-1}$ and 1620 $cm^{-1}$ can be seen in spectrum of the material of Example 25, indicating the successful attachment of bimatoprost to the material of Example 1.

Referring now to FIG. 18, a composite IR spectra is shown for the modified chitosan composition of this invention, pure bimatoprost and the modified chitosan/bimatoprost product prepared above. The figure shows the region of the IR spectra where amide absorbances appear for pure bimatoprost, the modified chitosan matrix, and the modified chitosan/Bimatoprost product. The development of new IR bands at 1540 $cm^{-1}$ and 1610 $cm^{-1}$ in the modified chitosan matrix IR spectra confirm the attachment of the bimatoprost to the modified chitosan matrix.

Example 26

Method for Preparation of Modified Chitosan/Bimatoprost Products

This example illustrates another procedure for attaching bimatoprost to modified chitosan materials of Example 1 for use as an enzyme-released bimatoprost delivery system. This alternative procedure produces a more pure linker-bimatoprost conjugate than the procedure given in Example 25.

Step 1: Linker Attachment to Bimatoprost 200 mg of bimatoprost (0.48 mmol), 48 mg of succinic anhydride (0.48 mmol), 147 mg of 4-dimethylamino pyridine (DMAP) (1.2 mmol), 74 µL of triethyl amine (TEA) (0.53 mmol), 1 g of DEAE Sephadex (40-125 µm particle size) were weighed out. Next, 4 mL of dichloromethane were added to a vial. The succinic anhydride was added to the vial and dissolved in the dichloromethane by vortexing. Next, the DMAP was added and dissolved by vortexing. Next, the bimatoprost was added and dissolved by vortexing. Next, the TEA was added and dissolved by vortexing. Finally, the DEAE was added and mixed by vortexing and the vial was tightly capped. The capped vial was then placed on a wrist action shaker and shaken for 1 hour at room temperature. As the reaction was proceeding, the plunger from a 10 mL syringe was removed. Small circles of filter paper were cut out and wetted. The wet filter paper circles were used to plug the syringe opening. The filter paper is designed to retard the flow of the DEAE gel. The syringe was filled to the 1 mL line with dry DEAE beads. The beads were wetted using water and then methanol. The reaction mixture was then pipetted into the syringe. The gel was washed with 40 mL of 75% methanol and 40 mL of water to remove any impurities or unreacted material. The gel was then washed with 40 mL of 1M NaCl to elute the product.

Step 2: Attachment to Modified Chitosan

Solubilization of Modified Chitosan

An appropriate amount of modified chitosan material of Example 1 was weighed out and added to the 1M NaCl washed product from step 1. The mixture was stirred for 24 hours. If modified chitosan did not dissolve, the mixture was gently heated to dissolve the modified chitosan using care not to exceed 60° C.

EDC Coupling of Modified Chitosan and Bimatoprost Succinate Product 0.11 g of EDC (per 100 mg modified chitosan) and 0.165 g NHS (per 100 mg modified chitosan) were weighed out and added to the solution from the previous step with stirring using a magnetic stir bar. The pH of the solution was checked and kept between pH 5 and 6. The reaction solution was stirred for 72 hours at room temperature.

Purification and Dialysis

After 72 hours, the pH of the solution was adjusted to pH 9 using 6M NaOH to precipitate the modified chitosan/bimatoprost product. The precipitated modified chitosan/bimatoprost product was place in a 150 mL beaker and 50 mL of 10% lactic acid was added. The precipitated modified chitosan/bimatoprost was stirred until all the modified chitosan/bimatoprost product was dissolved. The modified chitosan/bimatoprost product was precipitated by adjusting the pH to pH 9 using 6M NaOH. The mixture was then poured into a 50 mL centrifuge tube and centrifuged for 15 minutes at 3850× G. The supernatant was then removed and discarded. The modified chitosan/bimatoprost product was transferred to dialysis tubes and dialyzed against 10% lactic acid until the modified chitosan/bimatoprost product dissolved. After the modified chitosan/bimatoprost product dissolved, the dialysate was changed to DI water and the product was dialyzed for minimum of 3 hours for a minimum of 3 separate DI water dialyzing steps. The pH of modified chitosan/bimatoprost product was checked, and then the modified chitosan/bimatoprost product was dialyzed against PBS (pH 7.4) until the modified chitosan/bimatoprost product attained a pH of about 6. The PBS dialysis typically took about 30 minutes for the product to attain a pH of about 6. The product was then dialyzed against DI water for minimum 3 hours in a minimum of 2 separate DI water dialysis steps. The modified chitosan/bimatoprost product was removed from the dialysis tubes and placed in a freeze dryer flask. The flask was placed in a −80° C. freezer for a minimum of 1 hour or overnight. The flask was removed from the −80° C. freezer and placed on the freeze dryer until the product was completely dry.

Example 27

Periocular Injections Biocompatibility and Longevity of Base Material

This example was designed to determine the biocompatibility of a material of this invention when placed within the conjunctival tissue surrounding the rabbit eye and utilized the material of Example 1.
Procedure Two New Zealand White rabbits were used for this study. The rabbits and treatments were randomized. The experimental eyes were treated with 100 µL of the material of Example 1 at 10 mg/mL and the control eyes were treated with 100 µL BSS. The rabbits were anesthetized using isoflurane at 2.0 to 3.5% in a 40%/60% oxygen/air mixture. Two drops of a topical anesthetic (Tetracaine—0.5% drops or Alcaine) were applied to the rabbit eyes. A forceps was used to gently lift the conjunctiva from the surface of the globe resulting in a "tenting" of the conjunctiva. The injection was made well off the surface of the globe. (This maneuver greatly reduces the risk of globe perforation.) With the needle placed tangential to the globe, the needle tip was inserted into the tent, and the appropriate formulation was delivered. A 23-gauge needle was used to make the injections. 100 µL of the material of Example 1 was injected into the conjunctiva of the experimental eye. 100 µL of BSS was injected into the conjunctiva of the control eye. Following the injections, antibiotic drops (Vigamox®) were placed into the eyes. Daily observations were made for one week, then once a week until the study was concluded. Pictures were taken of the conjunctiva at 24 hours. At 29 days, the rabbits were euthanized and conjunctivas were harvested and processed for histology.
Results When looking at the rabbits before lowering the eyelid, no distinction could be made between the control and treated eyes throughout the entire study. All the rabbit eyes maintained a bright, moist appearance at all observation points. At 24 hours, all of the conjunctivas—both experimental and control—appeared normal indicating that the BSS had been absorbed into the tissue as well as the fluid component of the material of Example 1. No redness was noted in any of the conjunctiva. At 29 days, all the eyes appeared normal. There were no bumps present in any of the eyes. Histological assessment, utilizing calcofluor staining, confirmed, the presence of the material of Example 1 in the conjunctiva of experimental eyes 29 day post injection. Referring now to FIG. 19, the microscope images support the continued presence of the material at 29 days.
Conclusion The material of Example 1 shows promise as a means to provide sustained drug delivery to the eye. Following periocular injection, the material of this invention remained present in the conjunctival space for at least 29 days, with excellent biocompatibility.

Example 28

Periocular Injections: Biocompatibility and Longevity of Drug Loaded Material

This example was designed to determine the biocompatibility of a material of this invention, which has been covalently modified by the addition of bimatoprost, when placed within the conjunctival tissue surrounding the rabbit eye and utilized the material of Example 25.
Procedure Four New Zealand White rabbits were used for this study. The rabbits and treatments were randomized for this study. The experimental eyes were treated with 100 µL of the material of Example 25 at 10 mg/mL and the control eyes were treated with 100 µL of BSS. The rabbits were anesthetized using isoflurane at 2.0 to 3.5% in a 40%/60% oxygen/air mixture. Two drops of a topical anesthetic (Tetracaine—0.5% drops or Alcaine) were applied to the rabbit eyes. A forceps was used to gently lift the conjunctiva from the surface of the globe resulting in a "tenting" of the conjunctiva. The injection was made well off the surface of the globe. (This maneuver greatly reduces the risk of globe perforation.) With the needle placed tangential to the globe, the needle tip was inserted into the tent, and the appropriate formulation was delivered. A 23-gauge needle was used to make the injections. 100 µL of the material of Example 25 was injected into the conjunctiva of the experimental eye. 100 µL of BSS was injected into the conjunctiva of the control eye. Following the injections, antibiotic drops (Vigamox®) were placed into the eyes. Daily observations were made for one week, then once a week until the study was concluded. Pictures were taken of the conjunctiva at the time of injection, on day 1 and day 7. At the end of the study the rabbits were euthanized and conjunctivas were harvested and processed for histology.
Results When looking at the rabbits before lowering the eyelid, no distinction could be made between control and treated eyes throughout the entire study. All the rabbit eyes maintained a bright, moist appearance at all observation points. At 24 hours, all of the control conjunctivas appeared normal indicating that the BSS had been absorbed into the tissue. In all of the experimental conjunctivas, there was the presence of a pillow or bump, ranging from slight to prominent, along with a slight redness of the conjunctival tissue. The redness slowly diminished as the study progressed. (The eye itself and surrounding tissues remained completely normal throughout the study.) Within the first 24 hours, the relative bump size decreased, changing very little after that. At 29 days, all the eyes appeared normal. There was still a bump present in all of the experimental eyes. At the time of sectioning, it was very visible as to which of the conjunctiva contained the material of Example 25. Histological assessment, utilizing calcofluor staining, confirmed the presence of the chitosan compound of this invention in the conjunctiva of experimental eyes 29 days after injection. Referring now to FIG. 20, the macroscopic and microscopic evidence is shown supporting the continued presence of this material at 29 days.

Conclusion

The modified chitosan materials of this invention that have been covalently modified with bimatoprost show promise as a means to provide sustained drug delivery to the eye. Following periocular injection, these materials remained present in the conjunctival space for at least 29 days, with excellent biocompatibility. The slight redness observed in the conjunctiva of these experimental eyes following injection is likely attributed to the bimatoprost modification, given that the results from Example 27 show no signs of irritation from the base material alone.

Example 29

In vitro Hydrolysis Assay of Bimatoprost from a Chitosan Material of this Invention This example was designed to assess the ability to enzymatically release the bound bimatoprost. This was demonstrated by an in vitro hydrolysis assay using porcine esterase and lysozyme according to the following procedure.

Procedure

A solution of 0.1M borate buffer was prepared by adding 0.309 g of boric acid to 50 mL of DI water and adjusting the pH to 6.5 using 1M NaOH. A 5 mg/mL solution of the materials of Example 25 was aseptically prepared in sterile saline. 1000 units of porcine esterase and 20 units of egg white lysozyme per milliliter was dissolved in 0.1 M borate buffer. The standards were prepared as follows: Add 1 mL of borate buffer (pH 6.5) and 1 mL of 5 mg/mL modified chitosan material of Example 25 to each vial, vortex for 10 seconds to ensure complete mixing. Place the samples on a wrist action shaker and shake for 72 hours. Esterase samples were prepared as follows: Add 1 mL of the porcine esterase and egg white lysozyme solution (1000 units of porcine esterase and 20 units of egg white lysozyme per mL) and 1 mL of the 5 mg/mL modified chitosan material of Example 25 to each vial, vortex the samples for 10 seconds to ensure complete mixing. Place the samples on a wrist action shaker and shake for 72 hours.

After incubation, the samples were analyzed for released bimatoprost by HPLC.

Remove the sample from the shaker and vortex for 10 seconds, adjust the solution to pH 8-9 by adding 50 µl of 1M NaOH and vortex the sample for 10 seconds. Add 1 mL of methanol and vortex for 10 seconds. Pipette 1 mL of the sample into a microcentrifuge tube centrifuging each sample for 15 minute at 10000 rpm. Remove 200 mL of each sample for HPLC analysis, samples are run on a 250 mm×4.6 mm $C_{18}$ endcapped column (VWR) running isocratic methanol/water/acetic acid (70:30:0.1) at 1 mL/min detecting at 210 nm. The bimatoprost peak elutes at approximately 5.6 minutes, integrate the area under the peak and compare to a standard curve to determine the concentration.

Results

Figure 21:
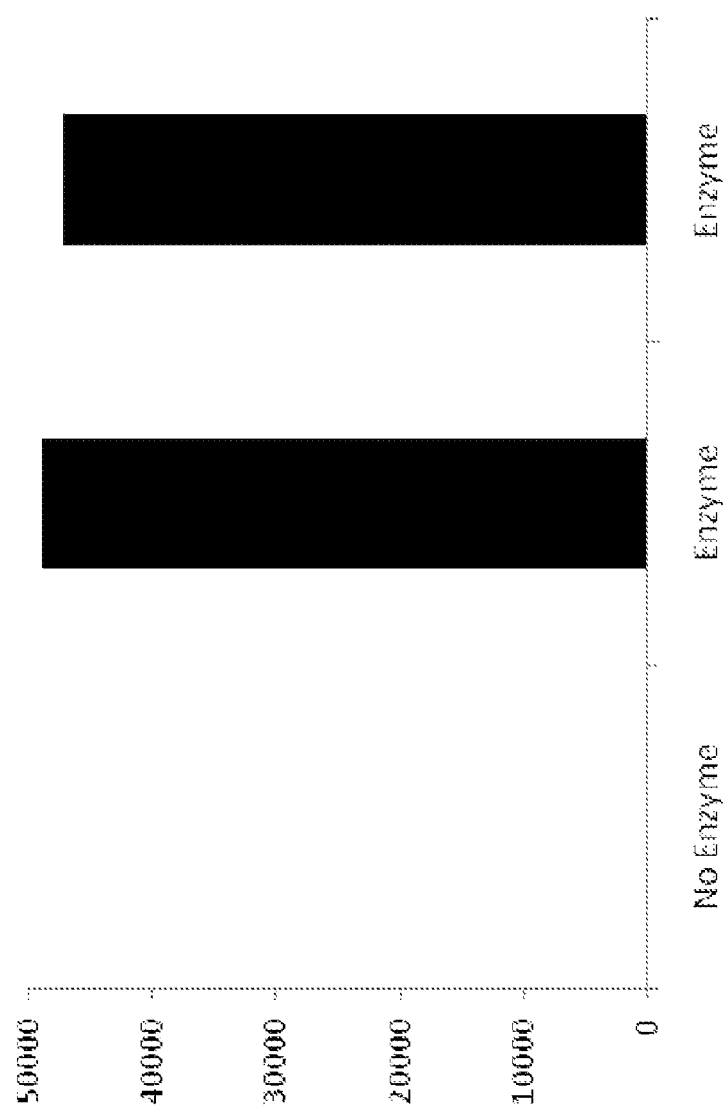
FIG. 21 depicts the relative release rates of covalently attached bimatoprost from the material of Example 25 in the presence and absence of enzymes. In the absence of any enzymes, no released bimatoprost can be detected, in the presence of porcine liver esterase and lysozyme, significant amounts of bimatoprost are released—in vitro study.

FIG. 21 shows the release profile of bimatoprost in both the presence and absence of the enzymes. In the absence of the enzymes, no detectable bimatoprost was observed. In the presence of the enzymes significant amounts of bimatoprost were released.

Conclusion

This example clearly illustrate that bimatoprost is efficiently released from a modified chitosan material of this invention under the action of esterase and lysozyme, which cleave the covalently bound bimatoprost.

The modified chitosan, bimatoprost compositions described herein can be used to successfully treat ocular conditions, such as glaucoma and to provide neuroprotection to retinal cells. Therapeutically effective modified chitosan formulations can also be prepared with other prostaglandins and prostamides such as (without limitation) PGD2, PGE2, PGF2, latanoprost and travoprost and unoprostone isopropyl.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for treating glaucoma, the method comprising the step of: administering to an eye of a patient a pharmaceutical composition comprising a modified chitosan and a therapeutic agent selected from the group consisting of a prostaglandin and a prostamide, thereby treating the glaucoma, wherein the modified chitosan is a chitosan that is covalently modified with an alkyl sulfonic acid, and wherein the therapeutic agent is covalently bonded to sites on the covalently modified chitosan via a linker.

2. The method of claim 1, wherein the alkyl sulfonic acid is octane sulfonic acid.

3. The method of claim 2, wherein the therapeutic agent is bimatoprost and the linker is succinic anhydride.

* * * * *